US012780886B2

(12) United States Patent
Borkan et al.

(10) Patent No.: US 12,780,886 B2
(45) Date of Patent: Nov. 3, 2026

(54) POLYPEPTIDE BAX/NPM INHIBITORS

(71) Applicants: TRUSTEES OF BOSTON UNIVERSITY, Boston, MA (US); BOSTON MEDICAL CENTER CORPORATION, Boston, MA (US)

(72) Inventors: Steven C. Borkan, Medfield, MA (US); Aaron B. Beeler, Boston, MA (US); Zhiyong Wang, Cambridge, MA (US); Jac Lorenzo, Dorchester, MA (US); Karen N. Allen, Weston, MA (US)

(73) Assignees: TRUSTEES OF BOSTON UNIVERSITY; BOSTON MEDICAL CENTER CORPORATION

( * ) Notice: Subject to any disclaimer, the term of this patent is extended or adjusted under 35 U.S.C. 154(b) by 0 days.

(21) Appl. No.: 18/606,396

(22) Filed: Mar. 15, 2024

(65) Prior Publication Data

US 2024/0309060 A1 Sep. 19, 2024

Related U.S. Application Data

(60) Provisional application No. 63/472,634, filed on Jun. 13, 2023, provisional application No. 63/452,773, filed on Mar. 17, 2023.

(51) Int. Cl.

| | |
|---|---|
| ***C07K 14/47*** | (2006.01) |
| ***A61K 38/00*** | (2006.01) |
| ***A61K 38/03*** | (2006.01) |
| ***A61K 38/10*** | (2006.01) |
| ***A61K 38/16*** | (2006.01) |
| ***A61P 13/12*** | (2006.01) |

(52) U.S. Cl.

CPC .......... *C07K 14/4747* (2013.01); *A61K 38/03* (2013.01); *A61K 38/10* (2013.01); *A61K 38/16* (2013.01); *A61P 13/12* (2018.01); *A61K 38/00* (2013.01)

(58) Field of Classification Search

None

See application file for complete search history.

(56) References Cited

U.S. PATENT DOCUMENTS

| | | | | |
|---|---|---|---|---|
| 4,966,848 A * | 10/1990 | Smith | C12N 9/1029 435/942 |
| 5,223,421 A * | 6/1993 | Smith | C12N 9/1029 435/255.2 |
| 5,837,218 A * | 11/1998 | Peers | A61K 51/088 424/1.65 |
| 2004/0053836 A1 | 3/2004 | Mayer-Kuckuk et al. | |
| 2004/0214272 A1 * | 10/2004 | La Rosa | C12N 15/8242 800/278 |
| 2005/0208558 A1 * | 9/2005 | Venter | C12Q 1/6888 435/6.16 |
| 2007/0254845 A1 | 11/2007 | Yung | |
| 2011/0105515 A1 | 5/2011 | Myers et al. | |

FOREIGN PATENT DOCUMENTS

WO WO-2016172722 A1 * 10/2016 ............. A61K 35/17

OTHER PUBLICATIONS

GenBank Accession No. MBR4308979.1, 2 pages (2021) (Year: 2021).*
Adessi et al., Curr. Medicinal Chem. 9:963-978 (2002) (Year: 2002).*
Yamazaki et al., Vet. Microbiol. 101:1-8 (2004) (Year: 2004).*
Boohaker et al., Mol. Pharm. 9:2080-2093 (2012) (Year: 2012).*
Lorenzo et al. "Peptides as therapeutics against acute kidney injury" Poster presented at the Boston Symposium on Organic and Bioorganic Chemistry on Oct. 13, 2022.
Wang et al. "Nucleophosmin Phosphorylation as a Diagnostic and Therapeutic Target for Ischemic AKI" Journal of the American Society of Nephrology. 30:50-62 (2019).
Wang et al. "T95 Nucleophosmin Threonine 95 Phosphorylation as a Novel Mediator and Marker of Cell Death." American Journal of Physiology 319:F522-561 (2020).

* cited by examiner

*Primary Examiner* — Thea D'Ambrosio
(74) *Attorney, Agent, or Firm* — NIXON PEABODY LLP; Ronald I. Eisenstein; Nicole D. Kling

(57) ABSTRACT

Described herein are polypeptides comprising at least one nucleophosmin-binding domain, including engineered polypeptides, and methods of using such polypeptides to treat or prevent acute kidney injury and/or kidney ischemia.

24 Claims, 23 Drawing Sheets

Specification includes a Sequence Listing.

| pp Number | Ave | SD |
|---|---|---|
| Control No stress | 100.0 | 6.3 |
| Negative Control | 47.2 | 5.2 |
| | | |
| NPM B1 AS2 | 86.6 | 7.3 |
| NPM B1 AS5 | 85.7 | 4.9 |
| NPM B1 AS7 | 85.5 | 8.1 |
| NPM B1 AS14 | 83.4 | 5.8 |

B: Baseline (without stress); N: Non-specific peptide;

Effective peptide modifications

Peptide #2: valine replaced by alanine

Peptide #5: phenylalanine replaced by alanine

Peptide #7: glycine replaced with alanine

Peptide #12: isoleucine was replaced with alanine

1. NPMB1-X-013: Ac-NLS-V173A-I175L-OMe
   Ac-PKKKRKV-Bala-TATLFVAGVLTASLTIWKKMG-OMe
2. NPMB1-X-008: Ac-NLS-F176A-G179A-OMe
   Ac-PKKKRKV-Bala-TVTIAVAAVLTASLTIWKKMG-OMe
3. NPMB1-X-009: Ac-NLS-T172Q-F176A-OMe
   Ac-PKKKRKV-Bala-QVTIAVAGVLTASLTIWKKMG-OMe
4. NPMB1-X-002: Ac-NLS-I175L-I187A-OMe
   Ac-PKKKRKV-Bala-TVTLFVAGVLTASLTAWKKMG -OMe
5. NPMB1-X-001: Ac-NLS-T172Q-I187A-OMe
   Ac-PKKKRKV-Bala-QVTIFVAGVLTASLTAWKKMG-OMe
6. NPMB1-X-012: Ac-NLS-V173A-F176A-OMe
   Ac-PKKKRKV-Bala-TATIAVAGVLTASLTIWKKMG-OMe

Fig. 13B

| # | Peptide | Association rate constant, $k_{on}$ ($\frac{1}{M\cdot s}$) | Dissociation rate constant, $k_{off}$ ($\frac{1}{s}$) | Equilibrium dissociation constant, $K_D$ ($\frac{k_{off}}{k_{on}}$, nM) | Normalized % Cell survival (MTT assay)# |
|---|---|---|---|---|---|
| a | NPMB1-I-010 | $7.32 \cdot 10^4$ | $6.16 \cdot 10^{-2}$ | 842 | ~55 |
| b | NPMB1-I-011 | $8.85 \cdot 10^4$ | $2.99 \cdot 10^{-2}$ | 337 | ~61 |
| c | NPMB1-V-001 | $1.26 \cdot 10^4$ | $7.25 \cdot 10^{-2}$ | 649 | **~85** |
| d | NPMB1-V-002 | $6.49 \cdot 10^4$ | $4.21 \cdot 10^{-2}$ | 5770 | ~31 |
| e | NPMB1-V-003 | $1.93 \cdot 10^4$ | $6.70 \cdot 10^{-2}$ | 3480 | ~64 |
| f | NPMB1-X-001 | $2.07 \cdot 10^4$ | $4.50 \cdot 10^{-2}$ | 3170 | ~54 |
| g | NPMB1-X-002 | $7.69 \cdot 10^4$ | $4.01 \cdot 10^{-2}$ | 522 | ~37 |
| h | NPMB1-X-008 | $7.79 \cdot 10^4$ | $3.98 \cdot 10^{-2}$ | 511 | ~42 |
| i | NPMB1-X-012 | $8.07 \cdot 10^4$ | $3.72 \cdot 10^{-2}$ | 462 | **~88** |
| j | NPMB1-X-013 | $7.59 \cdot 10^4$ | $3.76 \cdot 10^{-2}$ | 495 | **~71** |

Fig. 14

SEQUENCE LISTING

```
Sequence total quantity: 142
SEQ ID NO: 1            moltype = AA  length = 21
FEATURE                 Location/Qualifiers
source                  1..21
                        mol_type = protein
                        organism = synthetic construct
SEQUENCE: 1
TVTIFVAGVL TASLTIWKKM G                                    21

SEQ ID NO: 2            moltype = AA  length = 21
FEATURE                 Location/Qualifiers
source                  1..21
                        mol_type = protein
                        organism = synthetic construct
VARIANT                 1
                        note = Any amino acid
VARIANT                 2
                        note = Any amino acid
VARIANT                 4
                        note = Any amino acid
VARIANT                 5
                        note = Any amino acid
VARIANT                 7
                        note = Any amino acid
VARIANT                 8
                        note = Any amino acid
VARIANT                 9
                        note = Any amino acid
VARIANT                 12
                        note = Any amino acid
VARIANT                 14
                        note = Any amino acid
VARIANT                 15
                        note = Any amino acid
VARIANT                 16
                        note = Any amino acid
VARIANT                 20
                        note = Any amino acid
```

```
SEQUENCE: 2
XXTXXVXXXL TXSXXXWKKX G                                        21

SEQ ID NO: 3              moltype = AA  length = 21
FEATURE                   Location/Qualifiers
source                    1..21
                          mol_type = protein
                          organism = synthetic construct
VARIANT                   1
                          note = Any amino acid
VARIANT                   2
                          note = Any amino acid
VARIANT                   4
                          note = Any amino acid
VARIANT                   5
                          note = Any amino acid
VARIANT                   6
                          note = Any amino acid
VARIANT                   7
                          note = Any amino acid
VARIANT                   8
                          note = Any amino acid
VARIANT                   9
                          note = Any amino acid
VARIANT                   10
                          note = Any amino acid
VARIANT                   12
                          note = Any amino acid
VARIANT                   14
                          note = Any amino acid
VARIANT                   15
                          note = Any amino acid
VARIANT                   16
                          note = Any amino acid
VARIANT                   20
                          note = Any amino acid
SEQUENCE: 3
XXTXXXXXXX TXSXXXWKKX G                                        21

SEQ ID NO: 4              moltype = AA  length = 19
FEATURE                   Location/Qualifiers
source                    1..19
                          mol_type = protein
                          organism = synthetic construct
VARIANT                   2
                          note = Any amino acid
VARIANT                   3
                          note = Any amino acid
VARIANT                   5
                          note = Any amino acid
VARIANT                   6
                          note = Any amino acid
VARIANT                   7
                          note = Any amino acid
VARIANT                   10
                          note = Any amino acid
VARIANT                   12
                          note = Any amino acid
VARIANT                   13
                          note = Any amino acid
VARIANT                   14
                          note = Any amino acid
VARIANT                   18
                          note = Any amino acid
SEQUENCE: 4
TXXVXXXLTX SXXXWKKXG                                           19

SEQ ID NO: 5              moltype = AA  length = 19
FEATURE                   Location/Qualifiers
source                    1..19
                          mol_type = protein
                          organism = synthetic construct
VARIANT                   2
                          note = Any amino acid
VARIANT                   3
                          note = Any amino acid
VARIANT                   4
```

```
                        note = Any amino acid
VARIANT                 5
                        note = Any amino acid
VARIANT                 6
                        note = Any amino acid
VARIANT                 7
                        note = Any amino acid
VARIANT                 8
                        note = Any amino acid
VARIANT                 10
                        note = Any amino acid
VARIANT                 12
                        note = Any amino acid
VARIANT                 13
                        note = Any amino acid
VARIANT                 14
                        note = Any amino acid
VARIANT                 18
                        note = Any amino acid
SEQUENCE: 5
TXXXXXXXTX SXXXWKKXG                                             19

SEQ ID NO: 6            moltype = AA  length = 9
FEATURE                 Location/Qualifiers
source                  1..9
                        mol_type = protein
                        organism = synthetic construct
VARIANT                 2
                        note = Any amino acid
VARIANT                 4
                        note = Any amino acid
VARIANT                 5
                        note = Any amino acid
VARIANT                 6
                        note = Any amino acid
SEQUENCE: 6
TXSXXXWKK                                                        9

SEQ ID NO: 7            moltype = AA  length = 21
FEATURE                 Location/Qualifiers
source                  1..21
                        mol_type = protein
                        organism = synthetic construct
VARIANT                 2
                        note = Any amino acid
VARIANT                 5
                        note = Any amino acid
VARIANT                 7
                        note = Any amino acid
VARIANT                 8
                        note = Any amino acid
VARIANT                 12
                        note = Any amino acid
VARIANT                 16
                        note = Any amino acid
SEQUENCE: 7
TXTIXVXXVL TXSLTXWKKM G                                          21

SEQ ID NO: 8            moltype = AA  length = 17
FEATURE                 Location/Qualifiers
source                  1..17
                        mol_type = protein
                        organism = synthetic construct
VARIANT                 1
                        note = Any amino acid
VARIANT                 3
                        note = Any amino acid
VARIANT                 5
                        note = Any amino acid
VARIANT                 6
                        note = Any amino acid
VARIANT                 7
                        note = Any amino acid
VARIANT                 10
                        note = Any amino acid
VARIANT                 12
                        note = Any amino acid
VARIANT                 15
                        note = Any amino acid
```

```
SEQUENCE: 8
XIXVXXXLTX SXTIXKK                                                  17

SEQ ID NO: 9           moltype = AA  length = 21
FEATURE                Location/Qualifiers
source                 1..21
                       mol_type = protein
                       organism = synthetic construct
VARIANT                3
                       note = Any amino acid
VARIANT                5
                       note = Any amino acid
VARIANT                7
                       note = Any amino acid
VARIANT                8
                       note = Any amino acid
VARIANT                9
                       note = Any amino acid
VARIANT                12
                       note = Any amino acid
VARIANT                14
                       note = Any amino acid
VARIANT                17
                       note = Any amino acid
VARIANT                21
                       note = Any amino acid
SEQUENCE: 9
TVXIXVXXXL TXSXTIXKKM X                                             21

SEQ ID NO: 10          moltype = AA  length = 7
FEATURE                Location/Qualifiers
source                 1..7
                       mol_type = protein
                       organism = synthetic construct
SEQUENCE: 10
PKKKRKV                                                             7

SEQ ID NO: 11          moltype = AA  length = 21
FEATURE                Location/Qualifiers
source                 1..21
                       mol_type = protein
                       organism = synthetic construct
SEQUENCE: 11
TATIFVAGVL TASLTIWKKM G                                             21

SEQ ID NO: 12          moltype = AA  length = 21
FEATURE                Location/Qualifiers
source                 1..21
                       mol_type = protein
                       organism = synthetic construct
SEQUENCE: 12
TVTIFVAGVL TASLTAWKKM G                                             21

SEQ ID NO: 13          moltype = AA  length = 21
FEATURE                Location/Qualifiers
source                 1..21
                       mol_type = protein
                       organism = synthetic construct
SEQUENCE: 13
TVTIFVAAVL TASLTIWKKM G                                             21

SEQ ID NO: 14          moltype = AA  length = 21
FEATURE                Location/Qualifiers
source                 1..21
                       mol_type = protein
                       organism = synthetic construct
SEQUENCE: 14
TVTIAVAGVL TASLTIWKKM G                                             21

SEQ ID NO: 15          moltype = AA  length = 8
FEATURE                Location/Qualifiers
source                 1..8
                       mol_type = protein
                       organism = synthetic construct
SITE                   1
                       note = Acetylated residue
VARIANT                8
                       note = Beta-alanine or alanine
```

-continued

```
SEQUENCE: 15
PKKKRKVX                                                          8

SEQ ID NO: 16           moltype = AA  length = 7
FEATURE                 Location/Qualifiers
source                  1..7
                        mol_type = protein
                        organism = synthetic construct
SEQUENCE: 16
PKKKRKV                                                           7

SEQ ID NO: 17           moltype = AA  length = 16
FEATURE                 Location/Qualifiers
source                  1..16
                        mol_type = protein
                        organism = synthetic construct
SEQUENCE: 17
RREEERREEE RREEEK                                                 16

SEQ ID NO: 18           moltype = AA  length = 28
FEATURE                 Location/Qualifiers
source                  1..28
                        mol_type = protein
                        organism = synthetic construct
SITE                    1
                        note = Acetylated residue
VARIANT                 8
                        note = Beta-alanine or alanine
SITE                    28
                        note = Carboxylated residue
SEQUENCE: 18
PKKKRKVXVT TFSYGVQCFS RYPDHMKQ                                    28

SEQ ID NO: 19           moltype = AA  length = 29
FEATURE                 Location/Qualifiers
source                  1..29
                        mol_type = protein
                        organism = synthetic construct
SITE                    1
                        note = Acetylated residue
VARIANT                 8
                        note = Beta-alanine or alanine
SEQUENCE: 19
PKKKRKVXTV TIFVAGVLTA SLTIWKKMG                                   29

SEQ ID NO: 20           moltype = AA  length = 28
FEATURE                 Location/Qualifiers
source                  1..28
                        mol_type = protein
                        organism = synthetic construct
SITE                    1
                        note = Acetylated residue
VARIANT                 7
                        note = Beta-alanine or alanine
SITE                    28
                        note = Methyl ester modified residue
SEQUENCE: 20
KKKRKVXAVT IFVAGVLTAS LTIWKKMG                                    28

SEQ ID NO: 21           moltype = AA  length = 28
FEATURE                 Location/Qualifiers
source                  1..28
                        mol_type = protein
                        organism = synthetic construct
SITE                    1
                        note = Acetylated residue
VARIANT                 7
                        note = Beta-alanine or alanine
SITE                    28
                        note = Methyl ester modified residue
SEQUENCE: 21
KKKRKVXTAT IFVAGVLTAS LTIWKKMG                                    28

SEQ ID NO: 22           moltype = AA  length = 28
FEATURE                 Location/Qualifiers
source                  1..28
                        mol_type = protein
                        organism = synthetic construct
```

```
SITE                   1
                       note = Acetylated residue
VARIANT                7
                       note = Beta-alanine or alanine
SITE                   28
                       note = Methyl ester modified residue
SEQUENCE: 22
KKKRKVXTVA IFVAGVLTAS LTIWKKMG                                     28

SEQ ID NO: 23          moltype = AA  length = 28
FEATURE                Location/Qualifiers
source                 1..28
                       mol_type = protein
                       organism = synthetic construct
SITE                   1
                       note = Acetylated residue
VARIANT                7
                       note = Beta-alanine or alanine
SITE                   28
                       note = Methyl ester modified residue
SEQUENCE: 23
KKKRKVXTVT AFVAGVLTAS LTIWKKMG                                     28

SEQ ID NO: 24          moltype = AA  length = 28
FEATURE                Location/Qualifiers
source                 1..28
                       mol_type = protein
                       organism = synthetic construct
SITE                   1
                       note = Acetylated residue
VARIANT                7
                       note = Beta-alanine or alanine
SITE                   28
                       note = Methyl ester modified residue
SEQUENCE: 24
KKKRKVXTVT IAVAGVLTAS LTIWKKMG                                     28

SEQ ID NO: 25          moltype = AA  length = 28
FEATURE                Location/Qualifiers
source                 1..28
                       mol_type = protein
                       organism = synthetic construct
SITE                   1
                       note = Acetylated residue
VARIANT                7
                       note = Beta-alanine or alanine
SITE                   28
                       note = Methyl ester modified residue
SEQUENCE: 25
KKKRKVXTVT IFAAGVLTAS LTIWKKMG                                     28

SEQ ID NO: 26          moltype = AA  length = 28
FEATURE                Location/Qualifiers
source                 1..28
                       mol_type = protein
                       organism = synthetic construct
SITE                   1
                       note = Acetylated residue
VARIANT                7
                       note = Beta-alanine or alanine
SITE                   28
                       note = Methyl ester modified residue
SEQUENCE: 26
KKKRKVXTVT IFVAAVLTAS LTIWKKMG                                     28

SEQ ID NO: 27          moltype = AA  length = 28
FEATURE                Location/Qualifiers
source                 1..28
                       mol_type = protein
                       organism = synthetic construct
SITE                   1
                       note = Acetylated residue
VARIANT                7
                       note = Beta-alanine or alanine
SITE                   28
                       note = Methyl ester modified residue
SEQUENCE: 27
KKKRKVXTVT IFVAGALTAS LTIWKKMG                                     28
```

```
SEQ ID NO: 28          moltype = AA  length = 28
FEATURE                Location/Qualifiers
source                 1..28
                       mol_type = protein
                       organism = synthetic construct
SITE                   1
                       note = Acetylated residue
VARIANT                7
                       note = Beta-alanine or alanine
SITE                   28
                       note = Methyl ester modified residue
SEQUENCE: 28
KKKRKVXTVT IFVAGVATAS LTIWKKMG                                        28

SEQ ID NO: 29          moltype = AA  length = 28
FEATURE                Location/Qualifiers
source                 1..28
                       mol_type = protein
                       organism = synthetic construct
SITE                   1
                       note = Acetylated residue
VARIANT                7
                       note = Beta-alanine or alanine
SITE                   28
                       note = Methyl ester modified residue
SEQUENCE: 29
KKKRKVXTVT IFVAGVLAAS LTIWKKMG                                        28

SEQ ID NO: 30          moltype = AA  length = 28
FEATURE                Location/Qualifiers
source                 1..28
                       mol_type = protein
                       organism = synthetic construct
SITE                   1
                       note = Acetylated residue
VARIANT                7
                       note = Beta-alanine or alanine
SITE                   28
                       note = Methyl ester modified residue
SEQUENCE: 30
KKKRKVXTVT IFVAGVLTAA LTIWKKMG                                        28

SEQ ID NO: 31          moltype = AA  length = 28
FEATURE                Location/Qualifiers
source                 1..28
                       mol_type = protein
                       organism = synthetic construct
SITE                   1
                       note = Acetylated residue
VARIANT                7
                       note = Beta-alanine or alanine
SITE                   28
                       note = Methyl ester modified residue
SEQUENCE: 31
KKKRKVXTVT IFVAGVLTAS ATIWKKMG                                        28

SEQ ID NO: 32          moltype = AA  length = 28
FEATURE                Location/Qualifiers
source                 1..28
                       mol_type = protein
                       organism = synthetic construct
SITE                   1
                       note = Acetylated residue
VARIANT                7
                       note = Beta-alanine or alanine
SITE                   28
                       note = Methyl ester modified residue
SEQUENCE: 32
KKKRKVXTVT IFVAGVLTAS LAIWKKMG                                        28

SEQ ID NO: 33          moltype = AA  length = 28
FEATURE                Location/Qualifiers
source                 1..28
                       mol_type = protein
                       organism = synthetic construct
SITE                   1
                       note = Acetylated residue
VARIANT                7
                       note = Beta-alanine or alanine
```

```
SITE                    28
                        note = Methyl ester modified residue
SEQUENCE: 33
KKKRKVXTVT IFVAGVLTAS LTAWKKMG                                      28

SEQ ID NO: 34           moltype = AA  length = 28
FEATURE                 Location/Qualifiers
source                  1..28
                        mol_type = protein
                        organism = synthetic construct
SITE                    1
                        note = Acetylated residue
VARIANT                 7
                        note = Beta-alanine or alanine
SITE                    28
                        note = Methyl ester modified residue
SEQUENCE: 34
KKKRKVXTVT IFVAGVLTAS LTIAKKMG                                      28

SEQ ID NO: 35           moltype = AA  length = 28
FEATURE                 Location/Qualifiers
source                  1..28
                        mol_type = protein
                        organism = synthetic construct
SITE                    1
                        note = Acetylated residue
VARIANT                 7
                        note = Beta-alanine or alanine
SITE                    28
                        note = Methyl ester modified residue
SEQUENCE: 35
KKKRKVXTVT IFVAGVLTAS LTIWAKMG                                      28

SEQ ID NO: 36           moltype = AA  length = 28
FEATURE                 Location/Qualifiers
source                  1..28
                        mol_type = protein
                        organism = synthetic construct
SITE                    1
                        note = Acetylated residue
VARIANT                 7
                        note = Beta-alanine or alanine
SITE                    28
                        note = Methyl ester modified residue
SEQUENCE: 36
KKKRKVXTVT IFVAGVLTAS LTIWKAMG                                      28

SEQ ID NO: 37           moltype = AA  length = 28
FEATURE                 Location/Qualifiers
source                  1..28
                        mol_type = protein
                        organism = synthetic construct
SITE                    1
                        note = Acetylated residue
VARIANT                 7
                        note = Beta-alanine or alanine
SITE                    28
                        note = Methyl ester modified residue
SEQUENCE: 37
KKKRKVXTVT IFVAGVLTAS LTIWKKAG                                      28

SEQ ID NO: 38           moltype = AA  length = 28
FEATURE                 Location/Qualifiers
source                  1..28
                        mol_type = protein
                        organism = synthetic construct
SITE                    1
                        note = Acetylated residue
VARIANT                 7
                        note = Beta-alanine or alanine
SITE                    28
                        note = Methyl ester modified residue
SEQUENCE: 38
KKKRKVXTVT IFVAGVLTAS LTIWKKMA                                      28

SEQ ID NO: 39           moltype = AA  length = 28
FEATURE                 Location/Qualifiers
```

```
source                  1..28
                        mol_type = protein
                        organism = synthetic construct
SITE                    1
                        note = Acetylated residue
VARIANT                 8
                        note = Beta-alanine or alanine
SITE                    28
                        note = Carboxylated residue
SEQUENCE: 39
PKKKRKVXVT TFSYGVQCFS RYPDHMKQ                                    28

SEQ ID NO: 40           moltype = AA  length = 29
FEATURE                 Location/Qualifiers
source                  1..29
                        mol_type = protein
                        organism = synthetic construct
SITE                    1
                        note = Acetylated residue
VARIANT                 8
                        note = Beta-alanine or alanine
SEQUENCE: 40
PKKKRKVXTV TIFVAGVLTA SLTIWKKMG                                   29

SEQ ID NO: 41           moltype = AA  length = 38
FEATURE                 Location/Qualifiers
source                  1..38
                        mol_type = protein
                        organism = synthetic construct
SITE                    1
                        note = Acetylated residue
VARIANT                 17
                        note = Beta-alanine or alanine
SEQUENCE: 41
KKEEEKKEEE KKEEEKXTVT IFVAGVLTAS LTIWKKMG                         38

SEQ ID NO: 42           moltype = AA  length = 21
FEATURE                 Location/Qualifiers
source                  1..21
                        mol_type = protein
                        organism = synthetic construct
SITE                    21
                        note = Amidated residue
SEQUENCE: 42
TVTIFVAGVL TASLTIWKKM G                                           21

SEQ ID NO: 43           moltype = AA  length = 28
FEATURE                 Location/Qualifiers
source                  1..28
                        mol_type = protein
                        organism = synthetic construct
SITE                    1
                        note = Acetylated residue
VARIANT                 7
                        note = Beta-alanine or alanine
SITE                    28
                        note = Carboxylated residue
SEQUENCE: 43
KKKRKVXTVT IFVAGVLTAS LTIWKKMG                                    28

SEQ ID NO: 44           moltype = AA  length = 21
FEATURE                 Location/Qualifiers
source                  1..21
                        mol_type = protein
                        organism = synthetic construct
SITE                    21
                        note = Carboxylated residue
SEQUENCE: 44
TVTIFVAGVL TASLTIWKKM G                                           21

SEQ ID NO: 45           moltype = AA  length = 28
FEATURE                 Location/Qualifiers
source                  1..28
                        mol_type = protein
                        organism = synthetic construct
SITE                    1
                        note = Acetylated residue
VARIANT                 7
                        note = Beta-alanine or alanine
```

```
SITE                    28
                        note = Amidated residue
SEQUENCE: 45
KKKRKVXTVT IFVAGVLTAS LTIWKKMG                                      28

SEQ ID NO: 46           moltype = AA  length = 21
FEATURE                 Location/Qualifiers
source                  1..21
                        mol_type = protein
                        organism = synthetic construct
SITE                    21
                        note = Methyl ester modified residue
SEQUENCE: 46
TVTIFVAGVL TASLTIWKKM G                                             21

SEQ ID NO: 47           moltype = AA  length = 21
FEATURE                 Location/Qualifiers
source                  1..21
                        mol_type = protein
                        organism = synthetic construct
SITE                    1
                        note = Acetylated residue
SITE                    21
                        note = Carboxylated residue
SEQUENCE: 47
TVTIFVAGVL TASLTIWKKM G                                             21

SEQ ID NO: 48           moltype = AA  length = 21
FEATURE                 Location/Qualifiers
source                  1..21
                        mol_type = protein
                        organism = synthetic construct
SITE                    1
                        note = Acetylated residue
SITE                    21
                        note = Methyl ester modified residue
SEQUENCE: 48
TVTIFVAGVL TASLTIWKKM G                                             21

SEQ ID NO: 49           moltype = AA  length = 28
FEATURE                 Location/Qualifiers
source                  1..28
                        mol_type = protein
                        organism = synthetic construct
SITE                    1
                        note = Acetylated residue
VARIANT                 7
                        note = Beta-alanine or alanine
SITE                    28
                        note = Methyl ester modified residue
SEQUENCE: 49
KKKRKVXTVT IFVAGVLTAS LTIWKKMG                                      28

SEQ ID NO: 50           moltype = AA  length = 21
FEATURE                 Location/Qualifiers
source                  1..21
                        mol_type = protein
                        organism = synthetic construct
SITE                    1
                        note = Acetylated residue
SITE                    21
                        note = Amidated residue
SEQUENCE: 50
TVTIFVAGVL TASLTIWKKM G                                             21

SEQ ID NO: 51           moltype = AA  length = 29
FEATURE                 Location/Qualifiers
source                  1..29
                        mol_type = protein
                        organism = synthetic construct
VARIANT                 8
                        note = Beta-alanine or alanine
SEQUENCE: 51
PKKKRKVXTV TIFVAGVLTA SLTIWKKMG                                     29

SEQ ID NO: 52           moltype = AA  length = 28
FEATURE                 Location/Qualifiers
```

```
source                  1..28
                        mol_type = protein
                        organism = synthetic construct
SITE                    1
                        note = Acetylated residue
VARIANT                 7
                        note = Beta-alanine or alanine
VARIANT                 9
                        note = Any amino acid
VARIANT                 11
                        note = Any amino acid
VARIANT                 12
                        note = Any amino acid
VARIANT                 15
                        note = Any amino acid
VARIANT                 16
                        note = Any amino acid
VARIANT                 21
                        note = Any amino acid
VARIANT                 22
                        note = Any amino acid
VARIANT                 23
                        note = Any amino acid
VARIANT                 27
                        note = Any amino acid
SITE                    28
                        note = Methyl ester modified residue
SEQUENCE: 52
KKKRKVXTXT XXVAXXLTAS XXXWKKXG                                28

SEQ ID NO: 53           moltype = AA  length = 16
FEATURE                 Location/Qualifiers
source                  1..16
                        mol_type = protein
                        organism = synthetic construct
SEQUENCE: 53
KKRRRKKRRR KKRRRK                                             16

SEQ ID NO: 54           moltype = AA  length = 21
FEATURE                 Location/Qualifiers
source                  1..21
                        mol_type = protein
                        organism = synthetic construct
VARIANT                 2
                        note = Any amino acid
VARIANT                 4
                        note = Any amino acid
VARIANT                 5
                        note = Any amino acid
SEQUENCE: 54
TXTXXVAGVL TASLTIWKKM G                                       21

SEQ ID NO: 55           moltype = AA  length = 21
FEATURE                 Location/Qualifiers
source                  1..21
                        mol_type = protein
                        organism = synthetic construct
VARIANT                 2
                        note = V or A
VARIANT                 4
                        note = L or I
VARIANT                 5
                        note = F or A
SEQUENCE: 55
TXTXXVAGVL TASLTIWKKM G                                       21

SEQ ID NO: 56           moltype = AA  length = 21
FEATURE                 Location/Qualifiers
source                  1..21
                        mol_type = protein
                        organism = synthetic construct
SEQUENCE: 56
TVTLFVAGVL TASLTIWKKM G                                       21

SEQ ID NO: 57           moltype = AA  length = 21
FEATURE                 Location/Qualifiers
source                  1..21
                        mol_type = protein
                        organism = synthetic construct
```

```
SEQUENCE: 57
TATIAVAGVL TASLTIWKKM G                                           21

SEQ ID NO: 58          moltype = AA  length = 21
FEATURE                Location/Qualifiers
source                 1..21
                       mol_type = protein
                       organism = synthetic construct
SEQUENCE: 58
TATLFVAGVL TASLTIWKKM G                                           21

SEQ ID NO: 59          moltype = AA  length = 21
FEATURE                Location/Qualifiers
source                 1..21
                       mol_type = protein
                       organism = synthetic construct
VARIANT                1
                       note = Any amino acid
VARIANT                2
                       note = Any amino acid
VARIANT                4
                       note = Any amino acid
VARIANT                5
                       note = Any amino acid
VARIANT                8
                       note = Any amino acid
VARIANT                9
                       note = Any amino acid
VARIANT                15
                       note = Any amino acid
VARIANT                16
                       note = Any amino acid
SEQUENCE: 59
XXTXXVAXXL TASLXXWKKM G                                           21

SEQ ID NO: 60          moltype = AA  length = 21
FEATURE                Location/Qualifiers
source                 1..21
                       mol_type = protein
                       organism = synthetic construct
VARIANT                1
                       note = T or Q
VARIANT                2
                       note = V or A
VARIANT                4
                       note = L or I
VARIANT                5
                       note = F or A
VARIANT                8
                       note = G or A
VARIANT                9
                       note = V or L
VARIANT                15
                       note = T or Q
VARIANT                16
                       note = I or A
SEQUENCE: 60
XXTXXVAXXL TASLXXWKKM G                                           21

SEQ ID NO: 61          moltype = AA  length = 21
FEATURE                Location/Qualifiers
source                 1..21
                       mol_type = protein
                       organism = synthetic construct
SEQUENCE: 61
TVTLFVAGVL TASLTAWKKM G                                           21

SEQ ID NO: 62          moltype = AA  length = 21
FEATURE                Location/Qualifiers
source                 1..21
                       mol_type = protein
                       organism = synthetic construct
SEQUENCE: 62
QVTLFVAGLL TASLQIWKKM G                                           21

SEQ ID NO: 63          moltype = AA  length = 21
FEATURE                Location/Qualifiers
```

```
source                1..21
                      mol_type = protein
                      organism = synthetic construct
SEQUENCE: 63
QVTIFVAGVL TASLTIWKKM G                                           21

SEQ ID NO: 64         moltype = AA  length = 21
FEATURE               Location/Qualifiers
source                1..21
                      mol_type = protein
                      organism = synthetic construct
SEQUENCE: 64
TVTIAVAAVL TASLTIWKKM G                                           21

SEQ ID NO: 65         moltype = AA  length = 17
FEATURE               Location/Qualifiers
source                1..17
                      mol_type = protein
                      organism = synthetic construct
VARIANT               1
                      note = Any amino acid
VARIANT               2
                      note = Any amino acid
VARIANT               3
                      note = Any amino acid
VARIANT               5
                      note = Any amino acid
VARIANT               6
                      note = Any amino acid
VARIANT               7
                      note = Any amino acid
VARIANT               10
                      note = Any amino acid
VARIANT               12
                      note = Any amino acid
VARIANT               13
                      note = Any amino acid
VARIANT               14
                      note = Any amino acid
VARIANT               15
                      note = Any amino acid
SEQUENCE: 65
XXXVXXXLTX SXXXXKK                                                17

SEQ ID NO: 66         moltype = AA  length = 21
FEATURE               Location/Qualifiers
source                1..21
                      mol_type = protein
                      organism = synthetic construct
SITE                  21
                      note = Amidated residue
SEQUENCE: 66
TVTIFVAGVL TASLTIWKKM G                                           21

SEQ ID NO: 67         moltype = AA  length = 29
FEATURE               Location/Qualifiers
source                1..29
                      mol_type = protein
                      organism = synthetic construct
SITE                  1
                      note = Acetylated residue
VARIANT               8
                      note = Beta-alanine or alanine
SITE                  29
                      note = Carboxylated residue
SEQUENCE: 67
PKKKRKVXTV TIFVAGVLTA SLTIWKKMG                                   29

SEQ ID NO: 68         moltype = AA  length = 21
FEATURE               Location/Qualifiers
source                1..21
                      mol_type = protein
                      organism = synthetic construct
SITE                  21
                      note = Carboxylated residue
SEQUENCE: 68
TVTIFVAGVL TASLTIWKKM G                                           21

SEQ ID NO: 69         moltype = AA  length = 29
```

```
FEATURE                 Location/Qualifiers
source                  1..29
                        mol_type = protein
                        organism = synthetic construct
SITE                    1
                        note = Acetylated residue
VARIANT                 8
                        note = Beta-alanine or alanine
SITE                    29
                        note = Amidated residue
SEQUENCE: 69
PKKKRKVXTV TIFVAGVLTA SLTIWKKMG                                     29

SEQ ID NO: 70           moltype = AA  length = 21
FEATURE                 Location/Qualifiers
source                  1..21
                        mol_type = protein
                        organism = synthetic construct
SITE                    21
                        note = Methyl ester modified residue
SEQUENCE: 70
TVTIFVAGVL TASLTIWKKM G                                             21

SEQ ID NO: 71           moltype = AA  length = 21
FEATURE                 Location/Qualifiers
source                  1..21
                        mol_type = protein
                        organism = synthetic construct
SITE                    1
                        note = Acetylated residue
SITE                    21
                        note = Carboxylated residue
SEQUENCE: 71
TVTIFVAGVL TASLTIWKKM G                                             21

SEQ ID NO: 72           moltype = AA  length = 21
FEATURE                 Location/Qualifiers
source                  1..21
                        mol_type = protein
                        organism = synthetic construct
SITE                    1
                        note = Acetylated residue
SITE                    21
                        note = Methyl ester modified residue
SEQUENCE: 72
TVTIFVAGVL TASLTIWKKM G                                             21

SEQ ID NO: 73           moltype = AA  length = 29
FEATURE                 Location/Qualifiers
source                  1..29
                        mol_type = protein
                        organism = synthetic construct
SITE                    1
                        note = Acetylated residue
VARIANT                 8
                        note = Beta-alanine or alanine
SITE                    29
                        note = Methyl ester modified residue
SEQUENCE: 73
PKKKRKVXTV TIFVAGVLTA SLTIWKKMG                                     29

SEQ ID NO: 74           moltype = AA  length = 21
FEATURE                 Location/Qualifiers
source                  1..21
                        mol_type = protein
                        organism = synthetic construct
SITE                    1
                        note = Acetylated residue
SITE                    21
                        note = Amidated residue
SEQUENCE: 74
TVTIFVAGVL TASLTIWKKM G                                             21

SEQ ID NO: 75           moltype = AA  length = 38
FEATURE                 Location/Qualifiers
source                  1..38
                        mol_type = protein
                        organism = synthetic construct
```

```
SITE                    1
                        note = Acetylated residue
VARIANT                 17
                        note = Beta-alanine or alanine
SITE                    38
                        note = Carboxylated residue
SEQUENCE: 75
KKRRRKKRRR KKRRRKXTVT IFVAGVLTAS LTIWKKMG                               38

SEQ ID NO: 76           moltype = AA  length = 38
FEATURE                 Location/Qualifiers
source                  1..38
                        mol_type = protein
                        organism = synthetic construct
SITE                    1
                        note = Acetylated residue
VARIANT                 17
                        note = Beta-alanine or alanine
SITE                    38
                        note = Carboxylated residue
SEQUENCE: 76
RREEERREEE RREEEKXTVT IFVAGVLTAS LTIWKKMG                               38

SEQ ID NO: 77           moltype = AA  length = 27
FEATURE                 Location/Qualifiers
source                  1..27
                        mol_type = protein
                        organism = synthetic construct
SITE                    1
                        note = Acetylated residue
VARIANT                 8
                        note = Beta-alanine or alanine
SITE                    27
                        note = Methyl ester modified residue
SEQUENCE: 77
PKKKRKVXVT IFVAGVLTAS LTIWKKM                                           27

SEQ ID NO: 78           moltype = AA  length = 25
FEATURE                 Location/Qualifiers
source                  1..25
                        mol_type = protein
                        organism = synthetic construct
SITE                    1
                        note = Acetylated residue
VARIANT                 8
                        note = Beta-alanine or alanine
SITE                    25
                        note = Methyl ester modified residue
SEQUENCE: 78
PKKKRKVXTI FVAGVLTASL TIWKK                                             25

SEQ ID NO: 79           moltype = AA  length = 23
FEATURE                 Location/Qualifiers
source                  1..23
                        mol_type = protein
                        organism = synthetic construct
SITE                    1
                        note = Acetylated residue
VARIANT                 8
                        note = Beta-alanine or alanine
SITE                    23
                        note = Methyl ester modified residue
SEQUENCE: 79
PKKKRKVXIF VAGVLTASLT IWK                                               23

SEQ ID NO: 80           moltype = AA  length = 21
FEATURE                 Location/Qualifiers
source                  1..21
                        mol_type = protein
                        organism = synthetic construct
SITE                    1
                        note = Acetylated residue
VARIANT                 8
                        note = Beta-alanine or alanine
SITE                    21
                        note = Methyl ester modified residue
SEQUENCE: 80
PKKKRKVXFV AGVLTASLTI W                                                 21
```

-continued

```
SEQ ID NO: 81           moltype = AA  length = 19
FEATURE                 Location/Qualifiers
source                  1..19
                        mol_type = protein
                        organism = synthetic construct
SITE                    1
                        note = Acetylated residue
VARIANT                 8
                        note = Beta-alanine or alanine
SITE                    19
                        note = Methyl ester modified residue
SEQUENCE: 81
PKKKRKVXVA GVLTASLTI                                               19

SEQ ID NO: 82           moltype = AA  length = 29
FEATURE                 Location/Qualifiers
source                  1..29
                        mol_type = protein
                        organism = synthetic construct
SITE                    1
                        note = Acetylated residue
VARIANT                 8
                        note = Beta-alanine or alanine
SITE                    29
                        note = Methyl ester modified residue
SEQUENCE: 82
PKKKRKVXAV TIFVAGVLTA SLTIWKKMG                                    29

SEQ ID NO: 83           moltype = AA  length = 29
FEATURE                 Location/Qualifiers
source                  1..29
                        mol_type = protein
                        organism = synthetic construct
SITE                    1
                        note = Acetylated residue
VARIANT                 8
                        note = Beta-alanine or alanine
SITE                    29
                        note = Methyl ester modified residue
SEQUENCE: 83
PKKKRKVXTA TIFVAGVLTA SLTIWKKMG                                    29

SEQ ID NO: 84           moltype = AA  length = 29
FEATURE                 Location/Qualifiers
source                  1..29
                        mol_type = protein
                        organism = synthetic construct
SITE                    1
                        note = Acetylated residue
VARIANT                 8
                        note = Beta-alanine or alanine
SITE                    29
                        note = Methyl ester modified residue
SEQUENCE: 84
PKKKRKVXTV AIFVAGVLTA SLTIWKKMG                                    29

SEQ ID NO: 85           moltype = AA  length = 29
FEATURE                 Location/Qualifiers
source                  1..29
                        mol_type = protein
                        organism = synthetic construct
SITE                    1
                        note = Acetylated residue
VARIANT                 8
                        note = Beta-alanine or alanine
SITE                    29
                        note = Methyl ester modified residue
SEQUENCE: 85
PKKKRKVXTV TAFVAGVLTA SLTIWKKMG                                    29

SEQ ID NO: 86           moltype = AA  length = 29
FEATURE                 Location/Qualifiers
source                  1..29
                        mol_type = protein
                        organism = synthetic construct
SITE                    1
                        note = Acetylated residue
VARIANT                 8
                        note = Beta-alanine or alanine
```

```
SITE                   29
                       note = Methyl ester modified residue
SEQUENCE: 86
PKKKRKVXTV TIAVAGVLTA SLTIWKKMG                                    29

SEQ ID NO: 87          moltype = AA  length = 29
FEATURE                Location/Qualifiers
source                 1..29
                       mol_type = protein
                       organism = synthetic construct
SITE                   1
                       note = Acetylated residue
VARIANT                8
                       note = Beta-alanine or alanine
SITE                   29
                       note = Methyl ester modified residue
SEQUENCE: 87
PKKKRKVXTV TIFAAGVLTA SLTIWKKMG                                    29

SEQ ID NO: 88          moltype = AA  length = 29
FEATURE                Location/Qualifiers
source                 1..29
                       mol_type = protein
                       organism = synthetic construct
SITE                   1
                       note = Acetylated residue
VARIANT                8
                       note = Beta-alanine or alanine
SITE                   29
                       note = Methyl ester modified residue
SEQUENCE: 88
PKKKRKVXTV TIFVAAVLTA SLTIWKKMG                                    29

SEQ ID NO: 89          moltype = AA  length = 29
FEATURE                Location/Qualifiers
source                 1..29
                       mol_type = protein
                       organism = synthetic construct
SITE                   1
                       note = Acetylated residue
VARIANT                8
                       note = Beta-alanine or alanine
SITE                   29
                       note = Methyl ester modified residue
SEQUENCE: 89
PKKKRKVXTV TIFVAGALTA SLTIWKKMG                                    29

SEQ ID NO: 90          moltype = AA  length = 29
FEATURE                Location/Qualifiers
source                 1..29
                       mol_type = protein
                       organism = synthetic construct
SITE                   1
                       note = Acetylated residue
VARIANT                8
                       note = Beta-alanine or alanine
SITE                   29
                       note = Methyl ester modified residue
SEQUENCE: 90
PKKKRKVXTV TIFVAGVATA SLTIWKKMG                                    29

SEQ ID NO: 91          moltype = AA  length = 29
FEATURE                Location/Qualifiers
source                 1..29
                       mol_type = protein
                       organism = synthetic construct
SITE                   1
                       note = Acetylated residue
VARIANT                8
                       note = Beta-alanine or alanine
SITE                   29
                       note = Methyl ester modified residue
SEQUENCE: 91
PKKKRKVXTV TIFVAGVLAA SLTIWKKMG                                    29

SEQ ID NO: 92          moltype = AA  length = 29
FEATURE                Location/Qualifiers
```

```
source                1..29
                      mol_type = protein
                      organism = synthetic construct
SITE                  1
                      note = Acetylated residue
VARIANT               8
                      note = Beta-alanine or alanine
SITE                  29
                      note = Methyl ester modified residue
SEQUENCE: 92
PKKKRKVXTV TIFVAGVLTA ALTIWKKMG                                   29

SEQ ID NO: 93         moltype = AA  length = 29
FEATURE               Location/Qualifiers
source                1..29
                      mol_type = protein
                      organism = synthetic construct
SITE                  1
                      note = Acetylated residue
VARIANT               8
                      note = Beta-alanine or alanine
SITE                  29
                      note = Methyl ester modified residue
SEQUENCE: 93
PKKKRKVXTV TIFVAGVLTA SATIWKKMG                                   29

SEQ ID NO: 94         moltype = AA  length = 29
FEATURE               Location/Qualifiers
source                1..29
                      mol_type = protein
                      organism = synthetic construct
SITE                  1
                      note = Acetylated residue
VARIANT               8
                      note = Beta-alanine or alanine
SITE                  29
                      note = Methyl ester modified residue
SEQUENCE: 94
PKKKRKVXTV TIFVAGVLTA SLAIWKKMG                                   29

SEQ ID NO: 95         moltype = AA  length = 29
FEATURE               Location/Qualifiers
source                1..29
                      mol_type = protein
                      organism = synthetic construct
SITE                  1
                      note = Acetylated residue
VARIANT               8
                      note = Beta-alanine or alanine
SITE                  29
                      note = Methyl ester modified residue
SEQUENCE: 95
PKKKRKVXTV TIFVAGVLTA SLTAWKKMG                                   29

SEQ ID NO: 96         moltype = AA  length = 29
FEATURE               Location/Qualifiers
source                1..29
                      mol_type = protein
                      organism = synthetic construct
SITE                  1
                      note = Acetylated residue
VARIANT               8
                      note = Beta-alanine or alanine
SITE                  29
                      note = Methyl ester modified residue
SEQUENCE: 96
PKKKRKVXTV TIFVAGVLTA SLTIAKKMG                                   29

SEQ ID NO: 97         moltype = AA  length = 29
FEATURE               Location/Qualifiers
source                1..29
                      mol_type = protein
                      organism = synthetic construct
SITE                  1
                      note = Acetylated residue
VARIANT               8
                      note = Beta-alanine or alanine
SITE                  29
                      note = Methyl ester modified residue
```

```
SEQUENCE: 97
PKKKRKVXTV TIFVAGVLTA SLTIWAKMG                                    29

SEQ ID NO: 98           moltype = AA  length = 29
FEATURE                 Location/Qualifiers
source                  1..29
                        mol_type = protein
                        organism = synthetic construct
SITE                    1
                        note = Acetylated residue
VARIANT                 8
                        note = Beta-alanine or alanine
SITE                    29
                        note = Methyl ester modified residue
SEQUENCE: 98
PKKKRKVXTV TIFVAGVLTA SLTIWKAMG                                    29

SEQ ID NO: 99           moltype = AA  length = 29
FEATURE                 Location/Qualifiers
source                  1..29
                        mol_type = protein
                        organism = synthetic construct
SITE                    1
                        note = Acetylated residue
VARIANT                 8
                        note = Beta-alanine or alanine
SITE                    29
                        note = Methyl ester modified residue
SEQUENCE: 99
PKKKRKVXTV TIFVAGVLTA SLTIWKKAG                                    29

SEQ ID NO: 100          moltype = AA  length = 29
FEATURE                 Location/Qualifiers
source                  1..29
                        mol_type = protein
                        organism = synthetic construct
SITE                    1
                        note = Acetylated residue
VARIANT                 8
                        note = Beta-alanine or alanine
SITE                    29
                        note = Methyl ester modified residue
SEQUENCE: 100
PKKKRKVXTV TIFVAGVLTA SLTIWKKMA                                    29

SEQ ID NO: 101          moltype = AA  length = 29
FEATURE                 Location/Qualifiers
source                  1..29
                        mol_type = protein
                        organism = synthetic construct
SITE                    1
                        note = Acetylated residue
VARIANT                 8
                        note = Beta-alanine or alanine
SITE                    29
                        note = Methyl ester modified residue
SEQUENCE: 101
PKKKRKVXSV TIFVAGVLTA SLTIWKKMG                                    29

SEQ ID NO: 102          moltype = AA  length = 29
FEATURE                 Location/Qualifiers
source                  1..29
                        mol_type = protein
                        organism = synthetic construct
SITE                    1
                        note = Acetylated residue
VARIANT                 8
                        note = Beta-alanine or alanine
SITE                    29
                        note = Methyl ester modified residue
SEQUENCE: 102
PKKKRKVXTV TVFVAGVLTA SLTIWKKMG                                    29

SEQ ID NO: 103          moltype = AA  length = 29
FEATURE                 Location/Qualifiers
source                  1..29
                        mol_type = protein
                        organism = synthetic construct
```

```
SITE                   1
                       note = Acetylated residue
VARIANT                8
                       note = Beta-alanine or alanine
SITE                   29
                       note = Methyl ester modified residue
SEQUENCE: 103
PKKKRKVXTV TIFVAGLLTA SLTIWKKMG                              29

SEQ ID NO: 104         moltype = AA  length = 29
FEATURE                Location/Qualifiers
source                 1..29
                       mol_type = protein
                       organism = synthetic construct
SITE                   1
                       note = Acetylated residue
VARIANT                8
                       note = Beta-alanine or alanine
SITE                   29
                       note = Methyl ester modified residue
SEQUENCE: 104
PKKKRKVXTV TIFVAGVLTA SVTIWKKMG                              29

SEQ ID NO: 105         moltype = AA  length = 29
FEATURE                Location/Qualifiers
source                 1..29
                       mol_type = protein
                       organism = synthetic construct
SITE                   1
                       note = Acetylated residue
VARIANT                8
                       note = Beta-alanine or alanine
SITE                   29
                       note = Methyl ester modified residue
SEQUENCE: 105
PKKKRKVXTV TIFVAGVLTA SLSIWKKMG                              29

SEQ ID NO: 106         moltype = AA  length = 29
FEATURE                Location/Qualifiers
source                 1..29
                       mol_type = protein
                       organism = synthetic construct
SITE                   1
                       note = Acetylated residue
VARIANT                8
                       note = Beta-alanine or alanine
SITE                   29
                       note = Methyl ester modified residue
SEQUENCE: 106
PKKKRKVXTA TIAVAAVLTA SLTAWKKMG                              29

SEQ ID NO: 107         moltype = AA  length = 21
FEATURE                Location/Qualifiers
source                 1..21
                       mol_type = protein
                       organism = synthetic construct
SITE                   21
                       note = Amidated residue
SEQUENCE: 107
TVTIFVAGVL TASLTIWKKM G                                      21

SEQ ID NO: 108         moltype = AA  length = 29
FEATURE                Location/Qualifiers
source                 1..29
                       mol_type = protein
                       organism = synthetic construct
SITE                   1
                       note = Acetylated residue
VARIANT                8
                       note = Beta-alanine or alanine
SITE                   29
                       note = Carboxylated residue
SEQUENCE: 108
PKKKRKVXTV TIFVAGVLTA SLTIWKKMG                              29

SEQ ID NO: 109         moltype = AA  length = 21
FEATURE                Location/Qualifiers
```

```
source                  1..21
                        mol_type = protein
                        organism = synthetic construct
SITE                    21
                        note = Carboxylated residue
SEQUENCE: 109
TVTIFVAGVL TASLTIWKKM G                                           21

SEQ ID NO: 110          moltype = AA  length = 29
FEATURE                 Location/Qualifiers
source                  1..29
                        mol_type = protein
                        organism = synthetic construct
SITE                    1
                        note = Acetylated residue
VARIANT                 8
                        note = Beta-alanine or alanine
SITE                    29
                        note = Amidated residue
SEQUENCE: 110
PKKKRKVXTV TIFVAGVLTA SLTIWKKMG                                   29

SEQ ID NO: 111          moltype = AA  length = 21
FEATURE                 Location/Qualifiers
source                  1..21
                        mol_type = protein
                        organism = synthetic construct
SITE                    21
                        note = Methyl ester modified residue
SEQUENCE: 111
TVTIFVAGVL TASLTIWKKM G                                           21

SEQ ID NO: 112          moltype = AA  length = 21
FEATURE                 Location/Qualifiers
source                  1..21
                        mol_type = protein
                        organism = synthetic construct
SITE                    1
                        note = Acetylated residue
SITE                    21
                        note = Carboxylated residue
SEQUENCE: 112
TVTIFVAGVL TASLTIWKKM G                                           21

SEQ ID NO: 113          moltype = AA  length = 21
FEATURE                 Location/Qualifiers
source                  1..21
                        mol_type = protein
                        organism = synthetic construct
SITE                    1
                        note = Acetylated residue
SITE                    21
                        note = Methyl ester modified residue
SEQUENCE: 113
TVTIFVAGVL TASLTIWKKM G                                           21

SEQ ID NO: 114          moltype = AA  length = 29
FEATURE                 Location/Qualifiers
source                  1..29
                        mol_type = protein
                        organism = synthetic construct
SITE                    1
                        note = Acetylated residue
VARIANT                 8
                        note = Beta-alanine or alanine
SITE                    29
                        note = Methyl ester modified residue
SEQUENCE: 114
PKKKRKVXTV TIFVAGVLTA SLTIWKKMG                                   29

SEQ ID NO: 115          moltype = AA  length = 21
FEATURE                 Location/Qualifiers
source                  1..21
                        mol_type = protein
                        organism = synthetic construct
SITE                    1
                        note = Acetylated residue
SITE                    21
                        note = Amidated residue
```

```
SEQUENCE: 115
TVTIFVAGVL TASLTIWKKM G                                      21

SEQ ID NO: 116          moltype = AA  length = 38
FEATURE                 Location/Qualifiers
source                  1..38
                        mol_type = protein
                        organism = synthetic construct
SITE                    1
                        note = Acetylated residue
VARIANT                 17
                        note = Beta-alanine or alanine
SITE                    38
                        note = Carboxylated residue
SEQUENCE: 116
KKRRRKKRRR KKRRRKXTVT IFVAGVLTAS LTIWKKMG                    38

SEQ ID NO: 117          moltype = AA  length = 38
FEATURE                 Location/Qualifiers
source                  1..38
                        mol_type = protein
                        organism = synthetic construct
SITE                    1
                        note = Acetylated residue
VARIANT                 17
                        note = Beta-alanine or alanine
SITE                    38
                        note = Carboxylated residue
SEQUENCE: 117
RREEERREEE RREEEKXTVT IFVAGVLTAS LTIWKKMG                    38

SEQ ID NO: 118          moltype = AA  length = 27
FEATURE                 Location/Qualifiers
source                  1..27
                        mol_type = protein
                        organism = synthetic construct
SITE                    1
                        note = Acetylated residue
VARIANT                 8
                        note = Beta-alanine or alanine
SITE                    27
                        note = Methyl ester modified residue
SEQUENCE: 118
PKKKRKVXVT IFVAGVLTAS LTIWKKM                                27

SEQ ID NO: 119          moltype = AA  length = 25
FEATURE                 Location/Qualifiers
source                  1..25
                        mol_type = protein
                        organism = synthetic construct
SITE                    1
                        note = Acetylated residue
VARIANT                 8
                        note = Beta-alanine or alanine
SITE                    25
                        note = Methyl ester modified residue
SEQUENCE: 119
PKKKRKVXTI FVAGVLTASL TIWKK                                  25

SEQ ID NO: 120          moltype = AA  length = 23
FEATURE                 Location/Qualifiers
source                  1..23
                        mol_type = protein
                        organism = synthetic construct
SITE                    1
                        note = Acetylated residue
VARIANT                 8
                        note = Beta-alanine or alanine
SITE                    23
                        note = Methyl ester modified residue
SEQUENCE: 120
PKKKRKVXIF VAGVLTASLT IWK                                    23

SEQ ID NO: 121          moltype = AA  length = 21
FEATURE                 Location/Qualifiers
source                  1..21
                        mol_type = protein
                        organism = synthetic construct
```

-continued

```
SITE                  1
                      note = Acetylated residue
VARIANT               8
                      note = Beta-alanine or alanine
SITE                  21
                      note = Methyl ester modified residue
SEQUENCE: 121
PKKKRKVXFV AGVLTASLTI W                                              21

SEQ ID NO: 122        moltype = AA  length = 19
FEATURE               Location/Qualifiers
source                1..19
                      mol_type = protein
                      organism = synthetic construct
SITE                  1
                      note = Acetylated residue
VARIANT               8
                      note = Beta-alanine or alanine
SITE                  19
                      note = Methyl ester modified residue
SEQUENCE: 122
PKKKRKVXVA GVLTASLTI                                                 19

SEQ ID NO: 123        moltype = AA  length = 29
FEATURE               Location/Qualifiers
source                1..29
                      mol_type = protein
                      organism = synthetic construct
SITE                  1
                      note = Acetylated residue
VARIANT               8
                      note = Beta-alanine or alanine
SITE                  29
                      note = Methyl ester modified residue
SEQUENCE: 123
PKKKRKVXTV TLFVAGVLTA SLTIWKKMG                                      29

SEQ ID NO: 124        moltype = AA  length = 29
FEATURE               Location/Qualifiers
source                1..29
                      mol_type = protein
                      organism = synthetic construct
SITE                  1
                      note = Acetylated residue
VARIANT               8
                      note = Beta-alanine or alanine
SITE                  29
                      note = Methyl ester modified residue
SEQUENCE: 124
PKKKRKVXQV TLFVAGLLTA SLQIWKKMG                                      29

SEQ ID NO: 125        moltype = AA  length = 29
FEATURE               Location/Qualifiers
source                1..29
                      mol_type = protein
                      organism = synthetic construct
SITE                  1
                      note = Acetylated residue
VARIANT               8
                      note = Beta-alanine or alanine
SITE                  29
                      note = Methyl ester modified residue
SEQUENCE: 125
PKKKRKVXTV TIFVAGVLTA SLQIWKKMG                                      29

SEQ ID NO: 126        moltype = AA  length = 29
FEATURE               Location/Qualifiers
source                1..29
                      mol_type = protein
                      organism = synthetic construct
SITE                  1
                      note = Acetylated residue
VARIANT               8
                      note = Beta-alanine or alanine
SITE                  29
                      note = Methyl ester modified residue
SEQUENCE: 126
PKKKRKVXQV TIFVAGVLTA SLTIWKKMG                                      29
```

```
SEQ ID NO: 127          moltype = AA  length = 29
FEATURE                 Location/Qualifiers
source                  1..29
                        mol_type = protein
                        organism = synthetic construct
SITE                    1
                        note = Acetylated residue
VARIANT                 8
                        note = Beta-alanine or alanine
SITE                    29
                        note = Methyl ester modified residue
SEQUENCE: 127
PKKKRKVXQV TIFVAGVLTA SLTAWKKMG                                    29

SEQ ID NO: 128          moltype = AA  length = 29
FEATURE                 Location/Qualifiers
source                  1..29
                        mol_type = protein
                        organism = synthetic construct
SITE                    1
                        note = Acetylated residue
VARIANT                 8
                        note = Beta-alanine or alanine
SITE                    29
                        note = Methyl ester modified residue
SEQUENCE: 128
PKKKRKVXTV TLFVAGVLTA SLTAWKKMG                                    29

SEQ ID NO: 129          moltype = AA  length = 29
FEATURE                 Location/Qualifiers
source                  1..29
                        mol_type = protein
                        organism = synthetic construct
SITE                    1
                        note = Acetylated residue
VARIANT                 8
                        note = Beta-alanine or alanine
SITE                    29
                        note = Methyl ester modified residue
SEQUENCE: 129
PKKKRKVXTV TIAVAGVLTA SLTAWKKMG                                    29

SEQ ID NO: 130          moltype = AA  length = 29
FEATURE                 Location/Qualifiers
source                  1..29
                        mol_type = protein
                        organism = synthetic construct
SITE                    1
                        note = Acetylated residue
VARIANT                 8
                        note = Beta-alanine or alanine
SITE                    29
                        note = Methyl ester modified residue
SEQUENCE: 130
PKKKRKVXTV TIFVAAVLTA SLTAWKKMG                                    29

SEQ ID NO: 131          moltype = AA  length = 29
FEATURE                 Location/Qualifiers
source                  1..29
                        mol_type = protein
                        organism = synthetic construct
SITE                    1
                        note = Acetylated residue
VARIANT                 8
                        note = Beta-alanine or alanine
SITE                    29
                        note = Methyl ester modified residue
SEQUENCE: 131
PKKKRKVXTV TLFVAAVLTA SLTIWKKMG                                    29

SEQ ID NO: 132          moltype = AA  length = 29
FEATURE                 Location/Qualifiers
source                  1..29
                        mol_type = protein
                        organism = synthetic construct
SITE                    1
                        note = Acetylated residue
VARIANT                 8
                        note = Beta-alanine or alanine
```

```
SITE                    29
                        note = Methyl ester modified residue
SEQUENCE: 132
PKKKRKVXQV TIFVAAVLTA SLTIWKKMG                                    29

SEQ ID NO: 133          moltype = AA  length = 29
FEATURE                 Location/Qualifiers
source                  1..29
                        mol_type = protein
                        organism = synthetic construct
SITE                    1
                        note = Acetylated residue
VARIANT                 8
                        note = Beta-alanine or alanine
SITE                    29
                        note = Methyl ester modified residue
SEQUENCE: 133
PKKKRKVXTA TIFVAAVLTA SLTIWKKMG                                    29

SEQ ID NO: 134          moltype = AA  length = 29
FEATURE                 Location/Qualifiers
source                  1..29
                        mol_type = protein
                        organism = synthetic construct
SITE                    1
                        note = Acetylated residue
VARIANT                 8
                        note = Beta-alanine or alanine
SITE                    29
                        note = Methyl ester modified residue
SEQUENCE: 134
PKKKRKVXTV TIAVAAVLTA SLTIWKKMG                                    29

SEQ ID NO: 135          moltype = AA  length = 29
FEATURE                 Location/Qualifiers
source                  1..29
                        mol_type = protein
                        organism = synthetic construct
SITE                    1
                        note = Acetylated residue
VARIANT                 8
                        note = Beta-alanine or alanine
SITE                    29
                        note = Methyl ester modified residue
SEQUENCE: 135
PKKKRKVXQV TIAVAGVLTA SLTIWKKMG                                    29

SEQ ID NO: 136          moltype = AA  length = 29
FEATURE                 Location/Qualifiers
source                  1..29
                        mol_type = protein
                        organism = synthetic construct
SITE                    1
                        note = Acetylated residue
VARIANT                 8
                        note = Beta-alanine or alanine
SITE                    29
                        note = Methyl ester modified residue
SEQUENCE: 136
PKKKRKVXTV TLAVAGVLTA SLTIWKKMG                                    29

SEQ ID NO: 137          moltype = AA  length = 29
FEATURE                 Location/Qualifiers
source                  1..29
                        mol_type = protein
                        organism = synthetic construct
SITE                    1
                        note = Acetylated residue
VARIANT                 8
                        note = Beta-alanine or alanine
SITE                    29
                        note = Methyl ester modified residue
SEQUENCE: 137
PKKKRKVXQA TIFVAGVLTA SLTIWKKMG                                    29

SEQ ID NO: 138          moltype = AA  length = 29
FEATURE                 Location/Qualifiers
```

-continued

```
source                1..29
                      mol_type = protein
                      organism = synthetic construct
SITE                  1
                      note = Acetylated residue
VARIANT               8
                      note = Beta-alanine or alanine
SITE                  29
                      note = Methyl ester modified residue
SEQUENCE: 138
PKKKRKVXTA TIAVAGVLTA SLTIWKKMG                              29

SEQ ID NO: 139        moltype = AA  length = 29
FEATURE               Location/Qualifiers
source                1..29
                      mol_type = protein
                      organism = synthetic construct
SITE                  1
                      note = Acetylated residue
VARIANT               8
                      note = Beta-alanine or alanine
SITE                  29
                      note = Methyl ester modified residue
SEQUENCE: 139
PKKKRKVXTA TLFVAGVLTA SLTIWKKMG                              29

SEQ ID NO: 140        moltype = AA  length = 29
FEATURE               Location/Qualifiers
source                1..29
                      mol_type = protein
                      organism = synthetic construct
SITE                  1
                      note = Acetylated residue
VARIANT               8
                      note = Beta-alanine or alanine
SITE                  29
                      note = Methyl ester modified residue
SEQUENCE: 140
PKKKRKVXQV TLFVAGVLTA SLTIWKKMG                              29

SEQ ID NO: 141        moltype = AA  length = 29
FEATURE               Location/Qualifiers
source                1..29
                      mol_type = protein
                      organism = synthetic construct
SITE                  1
                      note = Acetylated residue
VARIANT               8
                      note = Beta-alanine or alanine
SITE                  29
                      note = Methyl ester modified residue
SEQUENCE: 141
PKKKRKVXTA TIFVAGVLTA SLTAWKKMG                              29

SEQ ID NO: 142        moltype = AA  length = 38
FEATURE               Location/Qualifiers
source                1..38
                      mol_type = protein
                      organism = synthetic construct
SITE                  1
                      note = Acetylated residue
SEQUENCE: 142
KKEEEKKEEE KKEEEKATVT IFVAGVLTAS LTIWKKMG                    38
```

POLYPEPTIDE BAX/NPM INHIBITORS

CROSS-REFERENCE TO RELATED APPLICATIONS

This application claims benefit under 35 U.S.C. § 119(e) of U.S. Provisional Application No. 63/472,634 filed Jun. 13, 2023 and 63/452,773 filed Mar. 17, 2023, the contents of which are incorporated herein by reference in their entirety.

GOVERNMENT SUPPORT

This invention was made with government support under Grant No DK118267 awarded by the National Institutes of Health. The government has certain rights in the invention.

SEQUENCE LISTING

The instant application contains a Sequence Listing which has been submitted electronically in XML format and is hereby incorporated by reference in its entirety. Said XML copy, created on Mar. 27, 2024, is named 701586-000106USPT_SL.xml and is 284,534 bytes in size.

TECHNICAL FIELD

The technology described herein relates to polypeptides that inhibit renal cell death, e.g., for treatment and prevention of acute kidney injury.

BACKGROUND

Acute Kidney Injury (AKI) lacks an effective therapy and is a growing public health challenge with staggering implications. In the US, 1 in 5 adults and 1 in 3 children admitted to hospital develop AKI and about 30% of these patients die. For example, AKI in cardiac surgery patients caused by ischemia occurs in 10-48% of 1 million annual surgeries and increases post-operative death by 4-fold, clearly showing that new therapeutics are needed. Because patients are at risk for AKI in many clinical situations and there are currently no effective therapies, AKI is an area of especially high unmet need.

SUMMARY

The technology described herein comprises novel, renally-targeted polypeptides, pharmaceutical compositions, and methods for prevention and treatment of AKI. Polypeptides and polypeptide derivatives of the invention bind to the cell protein nucleophosmin (NPM) and inhibit the formation of NPM:Bax complexes which promote the regulated cell death in the kidney that causes acute kidney injury (AKI).

Accordingly, in one embodiment of any of the aspects, described herein is a polypeptide comprising at least one nucleophosmin-binding domain, each nucleophosmin-binding domain comprising the sequence of SEQ ID NO: 6 or 8. In one embodiment of any of the aspects, described herein is a polypeptide comprising at least one nucleophosmin-binding domain, each nucleophosmin-binding domain comprising the sequence of SEQ ID NO: 6, 8, or 65.

In some embodiments of any of the aspects, the poplypeptide does not comprise the sequence of SEQ ID NO: 1. In some embodiments of any of the aspects, the poplypeptide comprises the sequence of SEQ ID NO: 2, 3, 4, 5, 7, 9, 11, 12, 13, or 14. In some embodiments of any of the aspects, an X comprised by one of SEQ ID Nos: 2-9 is a non-natural amino acid. In some embodiments of any of the aspects, an X comprised by one of SEQ ID Nos: 2-9 is a natural amino acid. In some embodiments of any of the aspects, an X comprised by one of SEQ ID Nos: 2-9 is alanine. In some embodiments of any of the aspects, an X comprised by one of SEQ ID Nos: 2-9 is beta-alanine. In some embodiments of any of the aspects, the poplypeptide comprises the sequence of SEQ ID NO: 2, 3, 4, 5, 7, 9, 11, 12, 13, 14, 54, 55, 56, 57, 58, 59, 60, 61, 62, 63, or 64. In some embodiments of any of the aspects, an X comprised by one of SEQ ID NOs: 2-9, 54, 55, or 65 is a non-natural amino acid. In some embodiments of any of the aspects, an X comprised by one of SEQ ID NOs: 2-9, 54, 55, or 65 is a natural amino acid. In some embodiments of any of the aspects, an X comprised by one of SEQ ID NOs: 2-9, 54, 55, or 65 is alanine. In some embodiments of any of the aspects, an X comprised by one of SEQ ID NOs2-9, 54, 55, or 65 is beta-alanine.

In some embodiments of any of the aspects, the polypeptide further comprises at least one N-terminus modification and/or at least one C-terminus modification. In some embodiments of any of the aspects, the at least one N-terminus modification and/or at least one C-terminus modification is selected from acetylation, methyl esterification, amidation, carboxylation, N-ethylamidation, or addition of pyroglutamate. In some embodiments of any of the aspects, the polypeptide comprises at least one C-terminus modification. In some embodiments of any of the aspects, the at least one C-terminus modification is amidation or methyl esterification. In some embodiments of any of the aspects, the at least one C-terminus modification is amidation. In some embodiments of any of the aspects, the at least one C-terminus modification is methyl esterification.

In some embodiments of any of the aspects, the polypeptide further comprises an N-terminal or C-terminal cell penetration motif. In some embodiments of any of the aspects, the polypeptide further comprises an N-terminal cell penetration motif. In some embodiments of any of the aspects, the cell penetration motif is a kidney cell penetration motif. In some embodiments of any of the aspects, the cell penetration motif comprises PKKKRKV (SEQ ID NO: 10) or RREEERREEERREEEK (SEQ ID NO: 17). In some embodiments of any of the aspects, the cell penetration motif comprises PKKKRKV (SEQ ID NO: 10), RREEERREEERREEEK (SEQ ID NO: 17), or KKRRRKKRRRKKRRRK (SEQ ID NO: 53). In some embodiments of any of the aspects, the N-terminal or C-terminal cell penetration motif and the at least one nucleophosmin-binding domain are separated by a linker. In some embodiments of any of the aspects, the linker is an alanine residue. In some embodiments of any of the aspects, the linker is a beta-alanine residue.

In some embodiments of any of the aspects, the polypeptide comprises the sequence of one of SEQ ID NOs: 18-50 and 66-141. In some embodiments of any of the aspects, the polypeptide comprises the sequence of one of SEQ ID NOs: 75, 76, 123, 124, 126, 128, 134, 138, and 139. In some embodiments of any of the aspects, the polypeptide comprises the sequence of one of SEQ ID NOs: 123, 138, and 139.

In one aspect of any of the embodiments, described herein is a method of treating or preventing acute kidney injury in a subject in need thereof, the method comprising administering the polypeptide described herein to the subject. In one aspect of any of the embodiments, described herein is a method of treating ischemia in a subject in need thereof, the method comprising administering the polypeptide described herein to the subject. In some embodiments of any of the aspects, the subject is a pre- or post-operative cardiac surgery patient. In some embodiments of any of the aspects, the treatment is prophylactic. In some embodiments of any of the aspects, the administration occurs before cardiac surgery.

BRIEF DESCRIPTION OF THE DRAWINGS

FIGS. 13A-13B depict the cytoprotective effects of select therapeutic peptides during ischemic stress in vitro. Primary murine proximal tubule epithelial cells (PTEC) were transiently exposed to metabolic inhibitors for 60 min and allowed to recover for 6 hr. to simulate ischemia in vivo; MTT assay estimated cell survival. "Control" (open bars); is a GFP fragment of similar size to the therapeutic peptides was used a negative control; NPMB1 (prototype) serves as a positive control. FIG. 13A is a graph demonsrating that six of 15 novel peptides (100 nM) with double mutations showed substantial cytoprotective effects vs. the negative control; test reagents 1, 3 and 6 showed the most robust protection (key is specific to FIGS. 13A-13B and is shown in FIG. 13B). All peptides contained the nuclear localizing sequence (NLS) to enhance peptide delivery to the kidney, a beta linker and both carboxy- and amino terminal modifications to reduce susceptibility to protease digestion; data are mean+standard error; n=3 separate experiments. Figure discloses SEQ ID NOS 139, 134-135, 128, 127, and 138, respectively, in order of appearance.

FIG. 14 depicts a table of the association rate, dissociation rate and the calculated equilibrium dissociation constant for 10 representative therapeutic peptides as measured by Surface Plasmon Resonance (SPR). Mean rates are derived from at least three different peptide concentrations at levels below saturation with human NPM1. Cell survival data are normalized to the negative control (a GFP fragment of similar size to the therapeutic peptides) and represent the mean of at least 3 separate experiments. Cell survival data in bold represents 3 of the most effective peptides (NPMV1-V-001, NPMB1-X-012, and NPMB1-X-13 in Example 2 nomenclature) with favorable drug-like properties.

DETAILED DESCRIPTION

Figure 1:
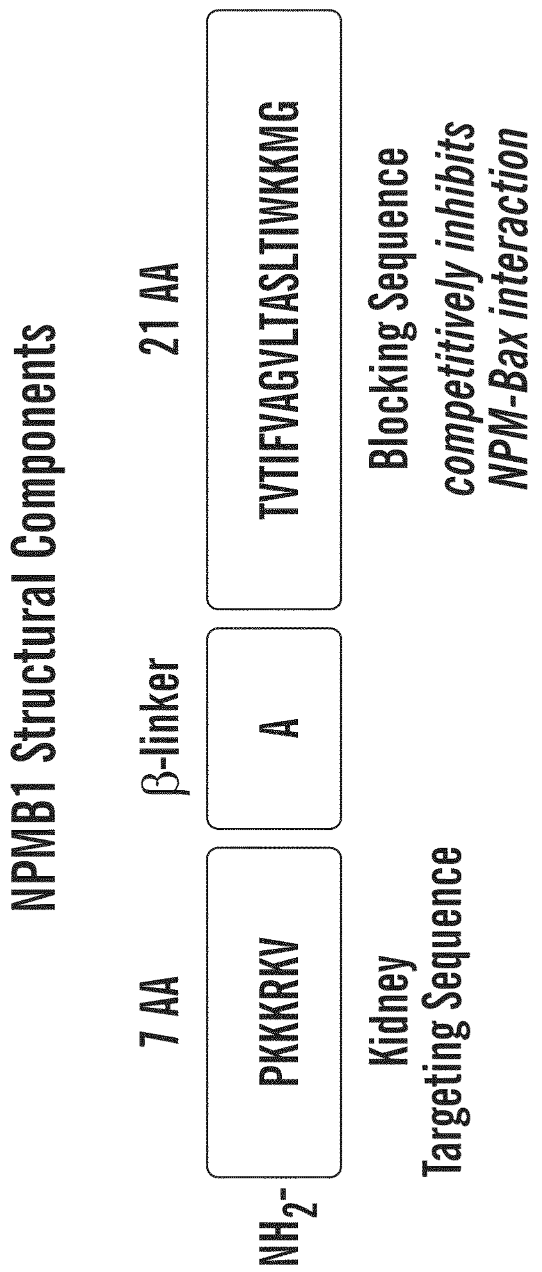
FIG. 1 depicts exemplary NPMB1 structural components: NPMB1 has 3 distinct domains: (1) amino terminal kidney targeting sequence (SEQ ID NO: 16), (2) beta-linker, and (3) carboxy-terminal sequence (SEQ ID NO: 1) that competitively inhibits NPM/Bax protein interaction in vivo (Wang 2019). Figure discloses SEQ ID NO: 51.

The inventors have identified sequences derived from BCL-2 Associated X Protein (BAX) that bind human nucelophosmin 1 (NPM1) and prevent its natural protein interaction and intracellular trafficking, thereby inhibiting cell death induced by ischemia, e.g., in acute kidney injury models. Notably, the inventors have identified a minimal polypeptide sequence that provides a therapeutically-relevant activity and a consensus sequence for that minimal sequence in which non-critical residues can be modified or substituted. The polypeptides described herein exhibit surprisingly improved inhibition of renal cell death in both a cell-based assay and in an in vivo mouse model of severe ischemic AKI Accordingly, in one aspect of any of the embodiments described herein is a polypeptide comprising at least one nucleophosmin-binding domain. As used herein, "nucleophosmin-binding domain" refers to a polypeptide (or portion of larger polypeptide molecule) that binds specifically to nucleophosmin, e.g., human nucleophosmin 1 (NPM1). In some embodiments of any of the aspects, a nucleophosmin-binding domain inhibits the interaction of NPM1 and BAX. Methods of measuring binding or inhibition of binding are well known in the art. For example, see Miura et al., Protein Pept Lett 2018 25:728-733 and Arkin et al. Inhibition of Protein-Protein Interactions: Non-Cellular Assay Formats. 2012 Mar. 18 [Updated 2012 Oct. 1]. In: Markossian S, Grossman A, Brimacombe K, et al., editors. Assay Guidance Manual [Internet]. Bethesda (MD): Eli Lilly & Company and the National Center for Advancing Translational Sciences; 2004-. Available on the world wide web at ncbi.nlm.nih.gov/books/NBK92000/; each of which is incorporated by reference herein in its entirety.

As used herein, "nucleophosmin", "nucleophosmin 1", or "NPM1" refers to a protein typically found in the nucleolus, where it binds nucleic acids. When bound by NPM1, BAX, is translocated to mitochondria and promotes regulated cell death. Sequences for NPM1 are known in the art, e.g., human NPM1 (NCBI Gene ID: 4869) cDNA (NCBI NM_001037738.3, NM_001355006.2, NM_001355007.2, NM_001355009.2, NM_001355010.2, NM_002520.7, and NM_199185.4) and protein sequences (NP_001032827.1, NP_001341935.1, NP_001341936.1, NP_001341938.1, NP_001341939.1, NP_002511.1, and NP_954654.1). The NCBI database provides the sequences of homologs and orthologs for over 300 species.

As used herein, "BCL-2 Associated X Protein" or "BAX" refers to a protein that forms a heterodimer with BCL2 to function as an apoptotic activator. Sequences for BAX are known in the art, e.g., human BAX (NCBI Gene ID: 581) cDNA (NCBI NM_001291428.2, NM_001291429.2, NM_001291430.2, NM_001291431.2, NM_004324.4, NM_138761.4, NM_138763.4, and NM_138764.5) and protein sequences (NP_001278357.1, NP_001278358.1, NP_001278359.1, NP_001278360.1, NP_004315.1, NP_620116.1, NP_620118.1, and NP_620119.2). The NCBI database provides the sequences of homologs and orthologs for over 200 species.

Where reference is made to database entries, e.g., NCBI database entries, reference is made to the information and sequences available as of Jun. 13, 2023 under the indicated ID and/or Acession Number.

In some of the embodiments of any of the aspects, described herein is a polypeptide comprising at least one nucleophosmin-binding domain, each nucleophosmin-binding domain comprising the sequence of SEQ ID NO: 6 or 8. In some of the embodiments of any of the aspects, described herein is a polypeptide comprising at least one nucleophosmin-binding domain, each nucleophosmin-binding domain consisting of the sequence of SEQ ID NO: 6 or 8. In some of the embodiments of any of the aspects, described herein is a polypeptide comprising at least one nucleophosmin-binding domain, each nucleophosmin-binding domain consisting essentially of the sequence of SEQ ID NO: 6 or 8.

In some of the embodiments of any of the aspects, described herein is a polypeptide comprising at least one nucleophosmin-binding domain, each nucleophosmin-binding domain comprising the sequence of SEQ ID NO: 6, 8, or 65. In some of the embodiments of any of the aspects, described herein is a polypeptide comprising at least one nucleophosmin-binding domain, each nucleophosmin-binding domain consisting of the sequence of SEQ ID NO: 6, 8, or 65. In some of the embodiments of any of the aspects, described herein is a polypeptide comprising at least one nucleophosmin-binding domain, each nucleophosmin-binding domain consisting essentially of the sequence of SEQ ID NO: 6, 8, or 65.

In some of the embodiments of any of the aspects, described herein is a polypeptide comprising at least one nucleophosmin-binding domain, each nucleophosmin-binding domain comprising the sequence of SEQ ID NO: 6. In some of the embodiments of any of the aspects, described herein is a polypeptide comprising at least one nucleophosmin-binding domain, each nucleophosmin-binding domain consisting of the sequence of SEQ ID NO: 6. In some of the embodiments of any of the aspects, described herein is a polypeptide comprising at least one nucleophosmin-binding domain, each nucleophosmin-binding domain consisting essentially of the sequence of SEQ ID NO: 6.

In some of the embodiments of any of the aspects, described herein is a polypeptide comprising at least one nucleophosmin-binding domain, each nucleophosmin-binding domain comprising the sequence of SEQ ID NO: 8. In some of the embodiments of any of the aspects, described herein is a polypeptide comprising at least one nucleophosmin-binding domain, each nucleophosmin-binding domain consisting of the sequence of SEQ ID NO: 8. In some of the embodiments of any of the aspects, described herein is a polypeptide comprising at least one nucleophosmin-binding domain, each nucleophosmin-binding domain consisting essentially of the sequence of SEQ ID NO: 8.

In some of the embodiments of any of the aspects, described herein is a polypeptide comprising at least one nucleophosmin-binding domain, each nucleophosmin-binding domain comprising the sequence of SEQ ID NO: 65. In some of the embodiments of any of the aspects, described herein is a polypeptide comprising at least one nucleophosmin-binding domain, each nucleophosmin-binding domain consisting of the sequence of SEQ ID NO: 65. In some of the embodiments of any of the aspects, described herein is a polypeptide comprising at least one nucleophosmin-binding domain, each nucleophosmin-binding domain consisting essentially of the sequence of SEQ ID NO: 65.

In some of the embodiments of any of the aspects, described herein is a polypeptide comprising at least one nucleophosmin-binding domain, each nucleophosmin-binding domain comprising the sequence of SEQ ID NO: 2, 3, 4, 5, 7, 9, 11, 12, 13, or 14. In some of the embodiments of any of the aspects, described herein is a polypeptide comprising at least one nucleophosmin-binding domain, each nucleophosmin-binding domain consisting of the sequence of SEQ ID NO: 2, 3, 4, 5, 7, 9, 11, 12, 13, or 14. In some of the embodiments of any of the aspects, described herein is a polypeptide comprising at least one nucleophosmin-binding domain, each nucleophosmin-binding domain consisting essentially of the sequence of SEQ ID NO: 2, 3, 4, 5, 7, 9, 11, 12, 13, or 14.

In some of the embodiments of any of the aspects, described herein is a polypeptide comprising at least one nucleophosmin-binding domain, each nucleophosmin-binding domain comprising the sequence of SEQ ID NO: 2, 3, 4, 5, 7, 9, 11, 12, 13, 14, 54, 55, 56, 57, 58, 59, 60, 61, 62, 63, or 64. In some of the embodiments of any of the aspects, described herein is a polypeptide comprising at least one nucleophosmin-binding domain, each nucleophosmin-binding domain consisting of the sequence of SEQ ID NO: 2, 3, 4, 5, 7, 9, 11, 12, 13, 14, 54, 55, 56, 57, 58, 59, 60, 61, 62, 63, or 64. In some of the embodiments of any of the aspects, described herein is a polypeptide comprising at least one nucleophosmin-binding domain, each nucleophosmin-binding domain consisting essentially of the sequence of SEQ ID NO: 2, 3, 4, 5, 7, 9, 11, 12, 13, 14, 54, 55, 56, 57, 58, 59, 60, 61, 62, 63, or 64.

In some of the embodiments of any of the aspects, described herein is a polypeptide comprising at least one nucleophosmin-binding domain, each nucleophosmin-binding domain comprising the sequence of SEQ ID NO: 2. In some of the embodiments of any of the aspects, described herein is a polypeptide comprising at least one nucleophosmin-binding domain, each nucleophosmin-binding domain consisting of the sequence of SEQ ID NO: 2. In some of the embodiments of any of the aspects, described herein is a polypeptide comprising at least one nucleophosmin-binding domain, each nucleophosmin-binding domain consisting essentially of the sequence of SEQ ID NO: 2.

In some of the embodiments of any of the aspects, described herein is a polypeptide comprising at least one nucleophosmin-binding domain, each nucleophosmin-binding domain comprising the sequence of SEQ ID NO: 3. In some of the embodiments of any of the aspects, described herein is a polypeptide comprising at least one nucleophosmin-binding domain, each nucleophosmin-binding domain consisting of the sequence of SEQ ID NO: 3. In some of the embodiments of any of the aspects, described herein is a polypeptide comprising at least one nucleophosmin-binding domain, each nucleophosmin-binding domain consisting essentially of the sequence of SEQ ID NO: 3.

In some of the embodiments of any of the aspects, described herein is a polypeptide comprising at least one nucleophosmin-binding domain, each nucleophosmin-binding domain comprising the sequence of SEQ ID NO: 4. In some of the embodiments of any of the aspects, described herein is a polypeptide comprising at least one nucleophosmin-binding domain, each nucleophosmin-binding domain consisting of the sequence of SEQ ID NO: 4. In some of the embodiments of any of the aspects, described herein is a polypeptide comprising at least one nucleophosmin-binding domain, each nucleophosmin-binding domain consisting essentially of the sequence of SEQ ID NO: 4.

In some of the embodiments of any of the aspects, described herein is a polypeptide comprising at least one nucleophosmin-binding domain, each nucleophosmin-binding domain comprising the sequence of SEQ ID NO: 5. In some of the embodiments of any of the aspects, described herein is a polypeptide comprising at least one nucleophosmin-binding domain, each nucleophosmin-binding domain consisting of the sequence of SEQ ID NO: 5. In some of the embodiments of any of the aspects, described herein is a polypeptide comprising at least one nucleophosmin-binding domain, each nucleophosmin-binding domain consisting essentially of the sequence of SEQ ID NO: 5.

In some of the embodiments of any of the aspects, described herein is a polypeptide comprising at least one nucleophosmin-binding domain, each nucleophosmin-binding domain comprising the sequence of SEQ ID NO: 7. In some of the embodiments of any of the aspects, described herein is a polypeptide comprising at least one nucleophosmin-binding domain, each nucleophosmin-binding domain consisting of the sequence of SEQ ID NO: 7. In some of the embodiments of any of the aspects, described herein is a polypeptide comprising at least one nucleophosmin-binding domain, each nucleophosmin-binding domain consisting essentially of the sequence of SEQ ID NO: 7.

In some of the embodiments of any of the aspects, described herein is a polypeptide comprising at least one nucleophosmin-binding domain, each nucleophosmin-binding domain comprising the sequence of SEQ ID NO: 9. In some of the embodiments of any of the aspects, described herein is a polypeptide comprising at least one nucleophosmin-binding domain, each nucleophosmin-binding domain consisting of the sequence of SEQ ID NO: 9. In some of the embodiments of any of the aspects, described herein is a polypeptide comprising at least one nucleophosmin-binding domain, each nucleophosmin-binding domain consisting essentially of the sequence of SEQ ID NO: 9.

In some of the embodiments of any of the aspects, described herein is a polypeptide comprising at least one nucleophosmin-binding domain, each nucleophosmin-binding domain comprising the sequence of SEQ ID NO: 11. In some of the embodiments of any of the aspects, described herein is a polypeptide comprising at least one nucleophosmin-binding domain, each nucleophosmin-binding domain consisting of the sequence of SEQ ID NO: 11. In some of the embodiments of any of the aspects, described herein is a polypeptide comprising at least one nucleophosmin-binding domain, each nucleophosmin-binding domain consisting essentially of the sequence of SEQ ID NO: 11.

In some of the embodiments of any of the aspects, described herein is a polypeptide comprising at least one nucleophosmin-binding domain, each nucleophosmin-binding domain comprising the sequence of SEQ ID NO: 12. In some of the embodiments of any of the aspects, described herein is a polypeptide comprising at least one nucleophosmin-binding domain, each nucleophosmin-binding domain consisting of the sequence of SEQ ID NO: 12. In some of the embodiments of any of the aspects, described herein is a polypeptide comprising at least one nucleophosmin-binding domain, each nucleophosmin-binding domain consisting essentially of the sequence of SEQ ID NO: 12.

In some of the embodiments of any of the aspects, described herein is a polypeptide comprising at least one nucleophosmin-binding domain, each nucleophosmin-binding domain comprising the sequence of SEQ ID NO: 13. In some of the embodiments of any of the aspects, described herein is a polypeptide comprising at least one nucleophosmin-binding domain, each nucleophosmin-binding domain consisting of the sequence of SEQ ID NO: 13. In some of the embodiments of any of the aspects, described herein is a polypeptide comprising at least one nucleophosmin-binding domain, each nucleophosmin-binding domain consisting essentially of the sequence of SEQ ID NO: 13.

In some of the embodiments of any of the aspects, described herein is a polypeptide comprising at least one nucleophosmin-binding domain, each nucleophosmin-binding domain comprising the sequence of SEQ ID NO: 14. In some of the embodiments of any of the aspects, described herein is a polypeptide comprising at least one nucleophosmin-binding domain, each nucleophosmin-binding domain consisting of the sequence of SEQ ID NO: 14. In some of the embodiments of any of the aspects, described herein is a polypeptide comprising at least one nucleophosmin-binding domain, each nucleophosmin-binding domain consisting essentially of the sequence of SEQ ID NO: 14.

In some of the embodiments of any of the aspects, described herein is a polypeptide comprising at least one nucleophosmin-binding domain, each nucleophosmin-binding domain comprising the sequence of SEQ ID NO: 54. In some of the embodiments of any of the aspects, described herein is a polypeptide comprising at least one nucleophosmin-binding domain, each nucleophosmin-binding domain consisting of the sequence of SEQ ID NO: 54. In some of the embodiments of any of the aspects, described herein is a polypeptide comprising at least one nucleophosmin-binding domain, each nucleophosmin-binding domain consisting essentially of the sequence of SEQ ID NO: 54.

In some of the embodiments of any of the aspects, described herein is a polypeptide comprising at least one nucleophosmin-binding domain, each nucleophosmin-binding domain comprising the sequence of SEQ ID NO: 55. In some of the embodiments of any of the aspects, described herein is a polypeptide comprising at least one nucleophosmin-binding domain, each nucleophosmin-binding domain consisting of the sequence of SEQ ID NO: 55. In some of the embodiments of any of the aspects, described herein is a polypeptide comprising at least one nucleophosmin-binding domain, each nucleophosmin-binding domain consisting essentially of the sequence of SEQ ID NO: 55.

In some of the embodiments of any of the aspects, described herein is a polypeptide comprising at least one nucleophosmin-binding domain, each nucleophosmin-binding domain comprising the sequence of SEQ ID NO: 56. In some of the embodiments of any of the aspects, described herein is a polypeptide comprising at least one nucleophosmin-binding domain, each nucleophosmin-binding domain consisting of the sequence of SEQ ID NO: 56. In some of the embodiments of any of the aspects, described herein is a polypeptide comprising at least one nucleophosmin-binding domain, each nucleophosmin-binding domain consisting essentially of the sequence of SEQ ID NO: 56.

In some of the embodiments of any of the aspects, described herein is a polypeptide comprising at least one nucleophosmin-binding domain, each nucleophosmin-binding domain comprising the sequence of SEQ ID NO: 57. In some of the embodiments of any of the aspects, described herein is a polypeptide comprising at least one nucleophosmin-binding domain, each nucleophosmin-binding domain consisting of the sequence of SEQ ID NO: 57. In some of the embodiments of any of the aspects, described herein is a polypeptide comprising at least one nucleophosmin-binding domain, each nucleophosmin-binding domain consisting essentially of the sequence of SEQ ID NO: 57.

In some of the embodiments of any of the aspects, described herein is a polypeptide comprising at least one nucleophosmin-binding domain, each nucleophosmin-binding domain comprising the sequence of SEQ ID NO: 58. In some of the embodiments of any of the aspects, described herein is a polypeptide comprising at least one nucleophosmin-binding domain, each nucleophosmin-binding domain consisting of the sequence of SEQ ID NO: 58. In some of the embodiments of any of the aspects, described herein is a polypeptide comprising at least one nucleophosmin-binding domain, each nucleophosmin-binding domain consisting essentially of the sequence of SEQ ID NO: 58.

In some of the embodiments of any of the aspects, described herein is a polypeptide comprising at least one nucleophosmin-binding domain, each nucleophosmin-binding domain comprising the sequence of SEQ ID NO: 59. In some of the embodiments of any of the aspects, described herein is a polypeptide comprising at least one nucleophosmin-binding domain, each nucleophosmin-binding domain consisting of the sequence of SEQ ID NO: 59. In some of the embodiments of any of the aspects, described herein is a polypeptide comprising at least one nucleophosmin-binding domain, each nucleophosmin-binding domain consisting essentially of the sequence of SEQ ID NO: 59.

In some of the embodiments of any of the aspects, described herein is a polypeptide comprising at least one nucleophosmin-binding domain, each nucleophosmin-binding domain comprising the sequence of SEQ ID NO: 60. In some of the embodiments of any of the aspects, described herein is a polypeptide comprising at least one nucleophosmin-binding domain, each nucleophosmin-binding domain consisting of the sequence of SEQ ID NO: 60. In some of the embodiments of any of the aspects, described herein is a polypeptide comprising at least one nucleophosmin-binding domain, each nucleophosmin-binding domain consisting essentially of the sequence of SEQ ID NO: 60.

In some of the embodiments of any of the aspects, described herein is a polypeptide comprising at least one nucleophosmin-binding domain, each nucleophosmin-binding domain comprising the sequence of SEQ ID NO: 61. In some of the embodiments of any of the aspects, described herein is a polypeptide comprising at least one nucleophosmin-binding domain, each nucleophosmin-binding domain consisting of the sequence of SEQ ID NO: 61. In some of the embodiments of any of the aspects, described herein is a polypeptide comprising at least one nucleophosmin-binding domain, each nucleophosmin-binding domain consisting essentially of the sequence of SEQ ID NO: 61.

In some of the embodiments of any of the aspects, described herein is a polypeptide comprising at least one nucleophosmin-binding domain, each nucleophosmin-binding domain comprising the sequence of SEQ ID NO: 62. In some of the embodiments of any of the aspects, described herein is a polypeptide comprising at least one nucleophosmin-binding domain, each nucleophosmin-binding domain consisting of the sequence of SEQ ID NO: 62. In some of the embodiments of any of the aspects, described herein is a polypeptide comprising at least one nucleophosmin-binding domain, each nucleophosmin-binding domain consisting essentially of the sequence of SEQ ID NO: 62.

In some of the embodiments of any of the aspects, described herein is a polypeptide comprising at least one nucleophosmin-binding domain, each nucleophosmin-binding domain comprising the sequence of SEQ ID NO: 63. In some of the embodiments of any of the aspects, described herein is a polypeptide comprising at least one nucleophosmin-binding domain, each nucleophosmin-binding domain consisting of the sequence of SEQ ID NO: 63. In some of the embodiments of any of the aspects, described herein is a polypeptide comprising at least one nucleophosmin-binding domain, each nucleophosmin-binding domain consisting essentially of the sequence of SEQ ID NO: 63.

In some of the embodiments of any of the aspects, described herein is a polypeptide comprising at least one nucleophosmin-binding domain, each nucleophosmin-binding domain comprising the sequence of SEQ ID NO: 64. In some of the embodiments of any of the aspects, described herein is a polypeptide comprising at least one nucleophosmin-binding domain, each nucleophosmin-binding domain consisting of the sequence of SEQ ID NO: 64. In some of the embodiments of any of the aspects, described herein is a polypeptide comprising at least one nucleophosmin-binding domain, each nucleophosmin-binding domain consisting essentially of the sequence of SEQ ID NO: 64.

TABLE 2

Subscripts designate a numbered position in a polyptide with respect to the reference sequence of SEQ ID NO: 1 and do not indicate a plurality of residues, e.g., "$X_2$" refers to a position corresponding to the $2^{nd}$ amino acid of SEQ ID NO: 1 and does not indicate the present of two Xs.

| SEQ ID NO | Sequence |
|---|---|
| 1 | TVTIFVAGVLTASLTIWKKMG |
| 2 | $X_1X_2TX_4X_5VX_7X_8X_9LTX_{12}SX_{14}X_{15}X_{16}WKKX_{20}G$<br>Where each X is any amino acid |
| 3 | $X_1X_2TX_4X_5X_6X_7X_8X_9X_{10}TX_{12}SX_{14}X_{15}X_{16}WKKX_{20}G$<br>Where each X is any amino acid |
| 4 | $TX_4X_5VX_7X_8X_9LTX_{12}SX_{14}X_{15}X_{16}WKKX_{20}G$<br>Where each X is any amino acid |
| 5 | $TX_4X_5X_6X_7X_8X_9X_{10}TX_{12}SX_{14}X_{15}X_{16}WKKX_{20}G$<br>Where each X is any amino acid |
| 6 | $TX_{12}SX_{14}X_{15}X_{16}WKK$<br>Where each X is any amino acid |
| 7 | $TX_2TIX_5VX_7X_8VLTX_{12}SLTX_{16}WKKMG$<br>Where each X is any amino acid |
| 8 | $X_3IX_5VX_7X_8X_9LTX_{12}SX_{14}TIX_{17}KK$<br>Where X is any amino acid |
| 9 | $TV\ X_{31}X_5VX_7X_8X_9LTX_{12}SX_{14}TIX_{17}KKMX_{21}$<br>Where X is any amino acid |
| 11 | TATIFVAGVLTASLTIWKKMG (Agent 2 comprises this sequence) |
| 12 | TVTIFVAGVLTASLTAWKKMG (Agent 5 comprises this sequence) |
| 13 | TVTIFVAAVLTASLTIWKKMG (Agent 7 comprises this sequence) |
| 14 | TVTIAVAGVLTASLTIWKKMG (Agent 12 comprises this sequence) |
| 54 | $TX_2TX_4X_5VAGVLTASLTIWKKMG$<br>Where each X is any amino acid |
| 55 | $TX_2TX_4X_5VAGVLTASLTIWKKMG$<br>Where $X_2$ is V or A; $X_4$ is L or I; and $X_5$ is F or A. |
| 56 | TVTLFVAGVLTASLTIWKKMG (Agent NPMB1-V-001 comprises this sequence) |
| 57 | TATIAVAGVLTASLTIWKKMG (Agent NPMB1-X-012 comprises this sequence) |
| 58 | TATLFVAGVLTASLTIWKKMG (Agent NPM1-X-013 comprises this sequence) |
| 59 | $X_1X_2TX_4X_5VAX_8X_9LTASLX_{15}X_{16}WKKMG$<br>Where each X is any amino acid |
| 60 | $X_1X_2TX_4X_5VAX_8X_9LTASLX_{15}X_{16}WKKMG$<br>Where $X_1$ is T or Q, $X_2$ is V or A, $X_4$ is L or I, $X_5$ is F or A, $X_8$ is G or A, $X_9$ is V or L, $X_{15}$ is T or Q, and $X_{16}$ is I or A. |
| 61 | TVTLFVAGVLTASLTAWKKMG (Agent $NPMB_1$-X-002 comprises this sequence) |
| 62 | QVTLFVAGLLTASLQIWKKMG (Agent $NPMB_1$-V-002 comprises this sequence) |
| 63 | QVTIFVAGVLTASLTIWKKMG (Agent $NPMB_1$-V-004 comprises this sequence) |
| 64 | TVTIAVAAVLTASLTIWKKMG (Agent $NPMB_1$-X-008 comprises this sequence) |
| 65 | $X_3X_4X_5VX_7X_8X_9LTX_{12}SX_{14}X_{15}X_{16}X_{17}KK$<br>Where X is any amino acid |

In some embodiments of any of the aspects, an X comprised by one of SEQ ID Nos: 2-9 is a non-natural amino acid. In some embodiments of any of the aspects, a non-natural amino acid can be selected from citrulline, diaminobutyric acid, cyclohexyl-alanine, t-leucine, 2-naphthyl-alanine, homophenylalanine, 3-pyridyl-alanine, beta-alanine, D-alanine, selenocysteine, homocysteine, or norleucine. In some embodiments of any of the aspects, an X comprised by one of SEQ ID Nos: 2-9 is a natural amino acid. In some embodiments of any of the aspects, an X comprised by one of SEQ ID Nos: 2-9 is alanine. In some embodiments of any of the aspects, an X comprised by one of SEQ ID Nos: 2-9 is beta-alanine.

In some embodiments of any of the aspects, an $X_1$ comprised by one of SEQ ID NOs:2-9 is serine, asparaginie, or glutamine. In some embodiments of any of the aspects, an $X_1$ comprised by one of SEQ ID NOs:2-9 is valine. In some embodiments of any of the aspects, an $X_1$ comprised by one of SEQ ID NOs:2-9 is citrulline or diaminobutyric acid. In some embodiments of any of the aspects, an $X_1$ comprised by one of SEQ ID NOs:2-9 is serine, asparaginie, glutamine, valine, citrulline, or diaminobutyric acid.

In some embodiments of any of the aspects, an $X_2$ comprised by one of SEQ ID NOs:2-9 is alanine, glycine, leucine, or isoleucine. In some embodiments of any of the aspects, an $X_2$ comprised by one of SEQ ID NOs:2-9 is threoinine or methionine. In some embodiments of any of the aspects, an $X_2$ comprised by one of SEQ ID NOs:2-9 is cyclohexyl-alanine or t-leucine. In some embodiments of any of the aspects, an $X_2$ comprised by one of SEQ ID NOs:2-9 is alanine, glycine, leucine, isoleucine, threoinine, methionine, cyclohexyl-alanine, or t-leucine. In some embodiments of any of the aspects, an $X_2$ comprised by one of SEQ ID NOs:2-9 is beta-alanine, alanine, glycine, leucine, isoleucine, threoinine, methionine, cyclohexyl-alanine, or t-leucine.

In some embodiments of any of the aspects, an $X_4$ comprised by one of SEQ ID NOs:2-9 is leucine or valine. In some embodiments of any of the aspects, an $X_4$ comprised by one of SEQ ID NOs:2-9 is methionine. In some embodiments of any of the aspects, an $X_4$ comprised by one of SEQ ID NOs:2-9 is cyclohexyl-alanine. In some embodiments of any of the aspects, an $X_4$ comprised by one of SEQ ID NOs:2-9 is leucine, valine, methionine, or cyclohexyl-alanine. In some embodiments of any of the aspects, an $X_4$ comprised by one of SEQ ID NOs:2-9 is beta-alanine, leucine, valine, methionine, or cyclohexyl-alanine.

In some embodiments of any of the aspects, an $X_5$ comprised by one of SEQ ID NOs:2-9 is alanine, tyrosine, or tryptophan. In some embodiments of any of the aspects, an $X_5$ comprised by one of SEQ ID NOs:2-9 is methionine, isoleucine, or leucine. In some embodiments of any of the aspects, an $X_5$ comprised by one of SEQ ID NOs:2-9 is 2-naphthyl-alanine, homophenylalanine, or 3-pyridyl-alanine. In some embodiments of any of the aspects, an $X_5$ comprised by one of SEQ ID NOs:2-9 is alanine, tyrosine, tryptophan, methionine, isoleucine, leucine, 2-naphthyl-alanine, homophenylalanine, or 3-pyridyl-alanine. In some embodiments of any of the aspects, an $X_5$ comprised by one of SEQ ID NOs:2-9 is beta-alanine, alanine, tyrosine, tryptophan, methionine, isoleucine, leucine, 2-naphthyl-alanine, homophenylalanine, or 3-pyridyl-alanine.

In some embodiments of any of the aspects, an $X_8$ comprised by one of SEQ ID NOs:2-9 is alanine. In some embodiments of any of the aspects, an $X_8$ comprised by one of SEQ ID NOs:2-9 is beta-alanine. In some embodiments of any of the aspects, an $X_8$ comprised by one of SEQ ID NOs:2-9 is serine or asparagine. In some embodiments of any of the aspects, an $X_8$ comprised by one of SEQ ID NOs:2-9 is beta-alanine or D-alanine. In some embodiments of any of the aspects, an $X_8$ comprised by one of SEQ ID NOs:2-9 is alanine, serine, asparagine, beta-alanine, or D-alanine.

In some embodiments of any of the aspects, an $X_9$ comprised by one of SEQ ID NOs:2-9 is leucine or isoleucine. In some embodiments of any of the aspects, an $X_9$ comprised by one of SEQ ID NOs:2-9 is threonine or methionine. In some embodiments of any of the aspects, an $X_9$ comprised by one of SEQ ID NOs:2-9 is cyclohexyl-alanine or t-leucine. In some embodiments of any of the aspects, an $X_9$ comprised by one of SEQ ID NOs:2-9 is leucine, isoleucine, threonine, methionine, cyclohexyl-alanine, or t-leucine. In some embodiments of any of the aspects, an $X_9$ comprised by one of SEQ ID NOs:2-9 is beta-alanine, leucine, isoleucine, threonine, methionine, cyclohexyl-alanine, or t-leucine.

In some embodiments of any of the aspects, an $X_{14}$ comprised by one of SEQ ID NOs:2-9 is valine or isoleucine. In some embodiments of any of the aspects, an $X_{14}$ comprised by one of SEQ ID NOs:2-9 is methionine. In some embodiments of any of the aspects, an $X_{14}$ comprised by one of SEQ ID NOs:2-9 is cyclohexyl-alanine. In some embodiments of any of the aspects, an $X_{14}$ comprised by one of SEQ ID NOs:2-9 is valine, isoleucine, methionine, or cyclohexyl-alanine. In some embodiments of any of the aspects, an $X_{14}$ comprised by one of SEQ ID NOs:2-9 is beta-alanine, valine, isoleucine, methionine, or cyclohexyl-alanine.

In some embodiments of any of the aspects, an $X_{15}$ comprised by one of SEQ ID NOs:2-9 is serine, asparagine, or glutamine. In some embodiments of any of the aspects, an $X_{15}$ comprised by one of SEQ ID NOs:2-9 is valine. In some embodiments of any of the aspects, an $X_{15}$ comprised by one of SEQ ID NOs:2-9 is citrulline or diaminobutyric acid. In some embodiments of any of the aspects, an $X_{15}$ comprised by one of SEQ ID NOs:2-9 is serine, asparagine, glutamine, valine, citrulline, or diaminobutyric acid.

In some embodiments of any of the aspects, an $X_{16}$ comprised by one of SEQ ID NOs:2-9 is leucine, valine, or alanine. In some embodiments of any of the aspects, an $X_{16}$ comprised by one of SEQ ID NOs:2-9 is methionine. In some embodiments of any of the aspects, an $X_{16}$ comprised by one of SEQ ID NOs:2-9 is cyclohexyl-alanine. In some embodiments of any of the aspects, an $X_{16}$ comprised by one of SEQ ID NOs:2-9 is leucine, valine, alanine, methionine, or cyclohexyl-alanine. In some embodiments of any of the aspects, an $X_{16}$ comprised by one of SEQ ID NOs:2-9 is beta-alanine, leucine, valine, alanine, methionine, or cyclohexyl-alanine.

In some embodiments of any of the aspects, an $X_{20}$ comprised by one of SEQ ID NOs:2-9 is cysteine, threonine, or serine. In some embodiments of any of the aspects, an $X_{20}$ comprised by one of SEQ ID NOs:2-9 is glutamine, isoleucine, leucine, or valine. In some embodiments of any of the aspects, an $X_{20}$ comprised by one of SEQ ID NOs:2-9 is selenocysteine, homocysteine, or norleucine. In some embodiments of any of the aspects, an $X_{20}$ comprised by one of SEQ ID NOs:2-9 is cysteine, threonine, serine, glutamine, isoleucine, leucine, valine, selenocysteine, homocysteine, or norleucine.

In some embodiments of any of the aspects, an X comprised by one of SEQ ID Nos: 2-9, 54, 55, or 65 is a non-natural amino acid. In some embodiments of any of the aspects, a non-natural amino acid can be selected from citrulline, diaminobutyric acid, cyclohexyl-alanine, t-leucine, 2-naphthyl-alanine, homophenylalanine, 3-pyridyl-alanine, beta-alanine, D-alanine, selenocysteine, homocysteine, or norleucine. In some embodiments of any of the aspects, an X comprised by one of SEQ ID Nos: 2-9, 54, 55, or 65 is a natural amino acid. In some embodiments of any of the aspects, an X comprised by one of SEQ ID Nos: 2-9, 54, 55, or 65 is alanine. In some embodiments of any of the aspects, an X comprised by one of SEQ ID Nos: 2-9, 54, 55, or 65 is beta-alanine.

In some embodiments of any of the aspects, an $X_1$ comprised by one of SEQ ID NOs:2-9, 54, 55, or 65 is serine, asparaginie, or glutamine. In some embodiments of any of the aspects, an $X_1$ comprised by one of SEQ ID NOs:2-9, 54, 55, or 65 is valine. In some embodiments of any of the aspects, an $X_1$ comprised by one of SEQ ID NOs:2-9, 54, 55, or 65 is citrulline or diaminobutyric acid. In some embodiments of any of the aspects, an $X_1$ comprised by one of SEQ ID NOs:2-9, 54, 55, or 65 is serine, asparaginie, glutamine, valine, citrulline, or diaminobutyric acid.

In some embodiments of any of the aspects, an $X_2$ comprised by one of SEQ ID NOs:2-9, 54, 55, or 65 is alanine, glycine, leucine, or isoleucine. In some embodiments of any of the aspects, an $X_2$ comprised by one of SEQ ID NOs:2-9, 54, 55, or 65 is threoinine or methionine. In some embodiments of any of the aspects, an $X_2$ comprised by one of SEQ ID NOs:2-9, 54, 55, or 65 is cyclohexyl-alanine or t-leucine. In some embodiments of any of the aspects, an $X_2$ comprised by one of SEQ ID NOs:2-9, 54, 55, or 65 is alanine, glycine, leucine, isoleucine, threoinine, methionine, cyclohexyl-alanine, or t-leucine. In some embodiments of any of the aspects, an $X_2$ comprised by one of SEQ ID NOs:2-9, 54, 55, or 65 is beta-alanine, alanine, glycine, leucine, isoleucine, threoinine, methionine, cyclohexyl-alanine, or t-leucine.

In some embodiments of any of the aspects, an $X_4$ comprised by one of SEQ ID NOs:2-9, 54, 55, or 65 is leucine or valine. In some embodiments of any of the aspects, an $X_4$ comprised by one of SEQ ID NOs:2-9, 54, 55, or 65 is methionine. In some embodiments of any of the aspects, an $X_4$ comprised by one of SEQ ID NOs:2-9, 54, 55, or 65 is cyclohexyl-alanine. In some embodiments of any of the aspects, an $X_4$ comprised by one of SEQ ID NOs:2-9, 54, 55, or 65 is leucine, valine, methionine, or cyclohexyl-alanine. In some embodiments of any of the aspects, an $X_4$ comprised by one of SEQ ID NOs:2-9, 54, 55, or 65 is beta-alanine, leucine, valine, methionine, or cyclohexyl-alanine.

In some embodiments of any of the aspects, an $X_5$ comprised by one of SEQ ID NOs:2-9, 54, 55, or 65 is alanine, tyrosine, or tryptophan. In some embodiments of any of the aspects, an $X_5$ comprised by one of SEQ ID NOs:2-9, 54, 55, or 65 is methionine, isoleucine, or leucine. In some embodiments of any of the aspects, an $X_5$ comprised by one of SEQ ID NOs:2-9, 54, 55, or 65 is 2-naphthyl-alanine, homophenylalanine, or 3-pyridyl-alanine. In some embodiments of any of the aspects, an $X_5$ comprised by one of SEQ ID NOs:2-9, 54, 55, or 65 is alanine, tyrosine, tryptophan, methionine, isoleucine, leucine, 2-naphthyl-alanine, homophenylalanine, or 3-pyridyl-alanine. In some embodiments of any of the aspects, an $X_5$ comprised by one of SEQ ID NOs:2-9, 54, 55, or 65 is beta-alanine, alanine, tyrosine, tryptophan, methionine, isoleucine, leucine, 2-naphthyl-alanine, homophenylalanine, or 3-pyridyl-alanine.

In some embodiments of any of the aspects, an $X_8$ comprised by one of SEQ ID NOs:2-9, 54, 55, or 65 is alanine. In some embodiments of any of the aspects, an $X_8$ comprised by one of SEQ ID NOs:2-9, 54, 55, or 65 is beta-alanine. In some embodiments of any of the aspects, an $X_8$ comprised by one of SEQ ID NOs:2-9, 54, 55, or 65 is serine or asparagine. In some embodiments of any of the aspects, an $X_8$ comprised by one of SEQ ID NOs:2-9, 54, 55, or 65 is beta-alanine or D-alanine. In some embodiments of any of the aspects, an $X_8$ comprised by one of SEQ ID NOs:2-9, 54, 55, or 65 is alanine, serine, asparagine, beta-alanine, or D-alanine.

In some embodiments of any of the aspects, an $X_9$ comprised by one of SEQ ID NOs:2-9, 54, 55, or 65 is leucine or isoleucine. In some embodiments of any of the aspects, an $X_9$ comprised by one of SEQ ID NOs:2-9, 54, 55, or 65 is threonine or methionine. In some embodiments of any of the aspects, an $X_9$ comprised by one of SEQ ID NOs:2-9, 54, 55, or 65 is cyclohexyl-alanine or t-leucine. In some embodiments of any of the aspects, an $X_9$ comprised by one of SEQ ID NOs:2-9, 54, 55, or 65 is leucine, isoleucine, threonine, methionine, cyclohexyl-alanine, or t-leucine. In some embodiments of any of the aspects, an $X_9$ comprised by one of SEQ ID NOs:2-9, 54, 55, or 65 is beta-alanine, leucine, isoleucine, threonine, methionine, cyclohexyl-alanine, or t-leucine.

In some embodiments of any of the aspects, an $X_{14}$ comprised by one of SEQ ID NOs:2-9, 54, 55, or 65 is valine or isoleucine. In some embodiments of any of the aspects, an $X_{14}$ comprised by one of SEQ ID NOs:2-9, 54, 55, or 65 is methionine. In some embodiments of any of the aspects, an $X_{14}$ comprised by one of SEQ ID NOs:2-9, 54, 55, or 65 is cyclohexyl-alanine. In some embodiments of any of the aspects, an $X_{14}$ comprised by one of SEQ ID NOs:2-9, 54, 55, or 65 is valine, isoleucine, methionine, or cyclohexyl-alanine. In some embodiments of any of the aspects, an $X_{14}$ comprised by one of SEQ ID NOs:2-9, 54, 55, or 65 is beta-alanine, valine, isoleucine, methionine, or cyclohexyl-alanine.

In some embodiments of any of the aspects, an $X_{15}$ comprised by one of SEQ ID NOs:2-9, 54, 55, or 65 is serine, asparagine, or glutamine. In some embodiments of any of the aspects, an $X_{15}$ comprised by one of SEQ ID NOs:2-9, 54, 55, or 65 is valine. In some embodiments of any of the aspects, an $X_{15}$ comprised by one of SEQ ID NOs:2-9, 54, 55, or 65 is citrulline or diaminobutyric acid. In some embodiments of any of the aspects, an $X_{15}$ comprised by one of SEQ ID NOs:2-9, 54, 55, or 65 is serine, asparagine, glutamine, valine, citrulline, or diaminobutyric acid.

In some embodiments of any of the aspects, an $X_{16}$ comprised by one of SEQ ID NOs:2-9, 54, 55, or 65 is leucine, valine, or alanine. In some embodiments of any of the aspects, an $X_{16}$ comprised by one of SEQ ID NOs:2-9, 54, 55, or 65 is methionine. In some embodiments of any of the aspects, an $X_{16}$ comprised by one of SEQ ID NOs:2-9, 54, 55, or 65 is cyclohexyl-alanine. In some embodiments of any of the aspects, an $X_{16}$ comprised by one of SEQ ID NOs:2-9, 54, 55, or 65 is leucine, valine, alanine, methionine, or cyclohexyl-alanine. In some embodiments of any of the aspects, an $X_{16}$ comprised by one of SEQ ID NOs:2-9, 54, 55, or 65 is beta-alanine, leucine, valine, alanine, methionine, or cyclohexyl-alanine.

In some embodiments of any of the aspects, an $X_{20}$ comprised by one of SEQ ID NOs:2-9, 54, 55, or 65 is cysteine, threonine, or serine. In some embodiments of any of the aspects, an $X_{20}$ comprised by one of SEQ ID NOs:2-9, 54, 55, or 65 is glutamine, isoleucine, leucine, or valine. In some embodiments of any of the aspects, an $X_{20}$ comprised by one of SEQ ID NOs:2-9, 54, 55, or 65 is selenocysteine, homocysteine, or norleucine. In some embodiments of any of the aspects, an $X_{20}$ comprised by one of SEQ ID NOs:2-9, 54, 55, or 65 is cysteine, threonine, serine, glutamine, isoleucine, leucine, valine, selenocysteine, homocysteine, or norleucine.

In some embodiments of any of the aspects, the at least one nucleophosmin binding domain comprises, consists of, or consists essentially of a sequence with at least 80%, at least 85%, at least 90%, at least 95%, at least 98%, at least 99%, or greater sequence identity to SEQ ID NO: 11, 12, 13, or 14. In some embodiments of any of the aspects, the at least one nucleophosmin binding domain comprises, consists of, or consists essentially of a sequence with at least 80% sequence identity to SEQ ID NO: 11, 12, 13, or 14. In some embodiments of any of the aspects, the at least one nucleophosmin binding domain comprises, consists of, or consists essentially of a sequence with at least 95% sequence identity to SEQ ID NO: 11, 12, 13, or 14. In some embodiments of any of the aspects, the at least one nucleophosmin binding domain comprises, consists of, or consists essentially of the sequence of one of SEQ ID NO: 11, 12, 13, or 14.

In some embodiments of any of the aspects, the at least one nucleophosmin binding domain comprises, consists of, or consists essentially of a sequence with at least 80%, at least 85%, at least 90%, at least 95%, at least 98%, at least 99%, or greater sequence identity to SEQ ID NO: 11, 12, 13, 14, 56, 57, 58, 61, 62, 63, or 64. In some embodiments of any of the aspects, the at least one nucleophosmin binding domain comprises, consists of, or consists essentially of a sequence with at least 80% sequence identity to SEQ ID NO: 11, 12, 13, 14, 56, 57, 58, 61, 62, 63, or 64. In some embodiments of any of the aspects, the at least one nucleophosmin binding domain comprises, consists of, or consists essentially of a sequence with at least 95% sequence identity to SEQ ID NO: 11, 12, 13, 14, 56, 57, 58, 61, 62, 63, or 64. In some embodiments of any of the aspects, the at least one nucleophosmin binding domain comprises, consists of, or consists essentially of the sequence of one of SEQ ID NO: 11, 12, 13, 14, 56, 57, 58, 61, 62, 63, or 64.

In some embodiments of any of the aspects, the at least one nucleophosmin binding domain comprises, consists of, or consists essentially of a sequence with at least 80%, at least 85%, at least 90%, at least 95%, at least 98%, at least 99%, or greater sequence identity to SEQ ID NO: 56, 57, 58, 61, 62, 63, or 64. In some embodiments of any of the aspects, the at least one nucleophosmin binding domain comprises, consists of, or consists essentially of a sequence with at least 80% sequence identity to SEQ ID NO: 56, 57, 58, 61, 62, 63, or 64. In some embodiments of any of the aspects, the at least one nucleophosmin binding domain comprises, consists of, or consists essentially of a sequence with at least 95% sequence identity to SEQ ID NO: 56, 57, 58, 61, 62, 63, or 64. In some embodiments of any of the aspects, the at least one nucleophosmin binding domain comprises, consists of, or consists essentially of the sequence of one of SEQ ID NO: 56, 57, 58, 61, 62, 63, or 64.

In some embodiments of any of the aspects, the at least one nucleophosmin binding domain comprises, consists of, or consists essentially of a sequence with at least 80%, at least 85%, at least 90%, at least 95%, at least 98%, at least 99%, or greater sequence identity to SEQ ID NO: 56, 57, or 58. In some embodiments of any of the aspects, the at least one nucleophosmin binding domain comprises, consists of, or consists essentially of a sequence with at least 80% sequence identity to SEQ ID NO: 56, 57, or 58. In some embodiments of any of the aspects, the at least one nucleophosmin binding domain comprises, consists of, or consists essentially of a sequence with at least 95% sequence identity to SEQ ID NO: 56, 57, or 58. In some embodiments of any of the aspects, the at least one nucleophosmin binding domain comprises, consists of, or consists essentially of the sequence of one of SEQ ID NO: 56, 57, or 58.

In some embodiments of any of the aspects, the at least one nucleophosmin binding domain comprises, consists of, or consists essentially of a sequence with at least 80%, at least 85%, at least 90%, at least 95%, at least 98%, at least 99%, or greater sequence identity to SEQ ID NO: 56. In some embodiments of any of the aspects, the at least one nucleophosmin binding domain comprises, consists of, or consists essentially of a sequence with at least 80% sequence identity to SEQ ID NO: 56. In some embodiments of any of the aspects, the at least one nucleophosmin binding domain comprises, consists of, or consists essentially of a sequence with at least 95% sequence identity to SEQ ID NO: 56. In some embodiments of any of the aspects, the at least one nucleophosmin binding domain comprises, consists of, or consists essentially of the sequence of SEQ ID NO: 56.

In some embodiments of any of the aspects, the at least one nucleophosmin binding domain comprises, consists of, or consists essentially of a sequence with at least 80%, at least 85%, at least 90%, at least 95%, at least 98%, at least 99%, or greater sequence identity to SEQ ID NO: 57. In some embodiments of any of the aspects, the at least one nucleophosmin binding domain comprises, consists of, or consists essentially of a sequence with at least 80% sequence identity to SEQ ID NO: 57. In some embodiments of any of the aspects, the at least one nucleophosmin binding domain comprises, consists of, or consists essentially of a sequence with at least 95% sequence identity to SEQ ID NO: 57. In some embodiments of any of the aspects, the at least one nucleophosmin binding domain comprises, consists of, or consists essentially of the sequence of SEQ ID NO: 57.

In some embodiments of any of the aspects, the at least one nucleophosmin binding domain comprises, consists of, or consists essentially of a sequence with at least 80%, at least 85%, at least 90%, at least 95%, at least 98%, at least 99%, or greater sequence identity to SEQ ID NO: 58. In some embodiments of any of the aspects, the at least one nucleophosmin binding domain comprises, consists of, or consists essentially of a sequence with at least 80% sequence identity to SEQ ID NO: 58. In some embodiments of any of the aspects, the at least one nucleophosmin binding domain comprises, consists of, or consists essentially of a sequence with at least 95% sequence identity to SEQ ID NO: 58. In some embodiments of any of the aspects, the at least one nucleophosmin binding domain comprises, consists of, or consists essentially of the sequence of SEQ ID NO: 58.

In some embodiments of any of the aspects, a polypeptide described herein comprises one nucleophosmin-binding domain. In some embodiments of any of the aspects, a polypeptide described herein consists of one nucleophosmin-binding domain. In some embodiments of any of the aspects, a polypeptide described herein consists essentially of one nucleophosmin-binding domain.

A polypeptide described herein can comprise multiple nucleophosmin-binding domains, e.g., 2, 3, 4, 5, or more nucleophosmin-binding domains. In some embodiments of any of the aspects, a polypeptide described herein comprises two or more nucleophosmin-binding domains. In some embodiments of any of the aspects, a polypeptide described herein consists of two or more nucleophosmin-binding domains. In some embodiments of any of the aspects, a polypeptide described herein consists essentially of two or more nucleophosmin-binding domains.

In some embodiments of any of the aspects, a polypeptide described herein comprises two nucleophosmin-binding domains. In some embodiments of any of the aspects, a polypeptide described herein consists of two nucleophosmin-binding domains. In some embodiments of any of the aspects, a polypeptide described herein consists essentially of two nucleophosmin-binding domains. In some embodiments of any of the aspects, a polypeptide described herein comprises three nucleophosmin-binding domains. In some embodiments of any of the aspects, a polypeptide described herein consists of three nucleophosmin-binding domains. In some embodiments of any of the aspects, a polypeptide described herein consists essentially of three nucleophosmin-binding domains. In some embodiments of any of the aspects, a polypeptide described herein comprises four nucleophosmin-binding domains. In some embodiments of any of the aspects, a polypeptide described herein consists of four nucleophosmin-binding domains. In some embodiments of any of the aspects, a polypeptide described herein consists essentially of four nucleophosmin-binding domains.

In a polypeptide comprising multiple nucleophosmin-binding domains, the multiple nucleophosmin domains can be copies or repeats of one nucleophosmin-binding domain sequences, or can each be a different nucleophosmin-binding domain sequence.

In some embodiments of any of the aspects, the polypeptide consists of the at least one nucleophosmin-binding domain. In some embodiments of any of the aspects, the polypeptide consists essentially of the at least one nucleophosmin-binding domain.

In some embodiments of any of the aspects, a polypeptide described herein does not comprise the sequence of SEQ ID NO: 1. In some embodiments of any of the aspects, a polypeptide described herein does not comprise a nucleophosmin-binding domain comprising the sequence of SEQ ID NO: 1. In some embodiments of any of the aspects, a polypeptide described herein comprises at least one nucleophosmin-binding domain that does not comprise the sequence of SEQ ID NO: 1.

In some embodiments of any of the aspects, a polypeptide described herein is an engineered polypeptide. In some embodiments of any of the aspects, a polypeptide described herein comprises a non-naturally occuring sequence. In some embodiments of any of the aspects, a polypeptide described does not comprise a wild-type BAX sequence, e.g., human BAX or a homolog thereof.

In some embodiments of any of the aspects, the at least one nucleophosmin-binding domain present in a composition of the disclosure exhibits an increased utility that is not exhibited when said at least one nucleophosmin-binding domain is present in a naturally occurring protein, or at naturally-occuring concentration. In some embodiments of any of the aspects, compositions of the disclosure, comprising at least one nucleophosmin-binding domain and at least one cell penetration motif as taught herein, exhibit a synergistic effect on imparting at least one improved trait in a therapeutic polypeptide, e.g., inhibition of kidney cell death. In some embodiments of any of the aspects, the compositions of the disclosure—comprising at least one nucleophosmin-binding domain as taught herein—exhibit markedly different characteristics/properties compared to their closest naturally occurring counterpart. That is, the compositions of the disclosure exhibit markedly different functional and/or structural characteristics/properties, as compared to their closest naturally occurring counterpart. For instance, the at least one nucleophosmin-binding domain of the disclosure are structurally different from a BAX protein as it naturally exists in nature and exhibit the opposite effect (cell death inhibition) of a BAX protein (cell death induction). The at least one nucleophosmin-binding domain of the disclosure is structurally different from a BAX protein as it naturally exists in nature and exhibit different functional characteristics, for at least the following reasons: said at least one nucleophosmin-binding domain can be isolated and purified, such that it is not found in the milieu of a BAX protein, said at least one nucleophosmin-binding domain can be present at concentrations that do not occur for BAX in a kidney cell, said at least one nucleophosmin-binding domain can be associated with acceptable carriers that do not occur in the kidney cell, said at least one nucleophosmin-binding domain can be formulated to be shelf-stable and exist outside the kidney cell environment, and said at least one nucleophosmin-binding domain can be combined with other domains, motifs, or therapeutics at concentrations that do not exist in the renal cell. Further, the at least one nucleophosmin-binding domain of the disclosure are functionally different from a BAX protein as it naturally exists in a kidney cell, for at least the following reasons: said at least one nucleophosmin-binding domain when applied in an isolated and purified form can lead to inhibition of cell death, said at least one nucleophosmin-binding domain can be formulated to be shelf-stable and able to exist outside the kidney cell environment, such that the at least one nucleophosmin-binding domain now has a new utility as a supplement capable of administration to a subject, wherein the BAX protein could not have such a utility in it's natural state in the renal cell, as the BAX protein exhibits induction of cell death without the intervention of the hand of man.

The polypeptides described herein can comprise modifications, e.g., chemical moieties added or substituted to the polypeptide structure as defined solely by the sequence. Exemplary, but non-limiting modifications include acetylation, methyl esterification, amidation, carboxylation, N-ethylamidation, or addition of pyroglutamate. In some embodiments of any of the aspects, the polypeptide described herein further comprises a N-terminus modification. In some embodiments of any of the aspects, the polypeptide described herein further comprises at least one N-terminus modification. In some embodiments of any of the aspects, the polypeptide described herein further comprises a C-terminus modification. In some embodiments of any of the aspects, the polypeptide described herein further comprises at least one C-terminus modification.

In some embodiments of any of the aspects, the polypeptide described herein further comprises a C-terminus modification selected from amidation and methyl esterification. In some embodiments of any of the aspects, the polypeptide described herein further comprises a C-terminus amidation. In some embodiments of any of the aspects, the polypeptide described herein further comprises a C-terminus methyl esterification.

The polypeptides described herein can further comprise a cell penetration motif. As used herein "cell penetration motif" refers to a polypeptide or polypeptide sequence capable of crossing the lipid bilayer of a cell. Numerous cell penetrating motifs are known in the art, including but not limited to TAT, penetration, transportant, PEP-1, Pept 1; Pept 2; IVV-14, transportan; pVEc; HSRV; and the like. Cell penetration motifs, e.g., cell-penetrating peptides, are described further in the art. For example, in Derakhshankhah H et al. (December 2018). "Cell penetrating peptides: A concise review with emphasis on biomedical applications". Biomedicine & Pharmacotherapy. 108: 1090-1096; Milletti F (August 2012). "Cell-penetrating peptides: classes, origin, and current landscape". Drug Discovery Today. 17 (15-16): 850-60; each of which is incorporated by reference herein in its entirety.

The cell penetration motif can be N-terminal or C-terminal, e.g., with respect to the overall structure of the polypeptide. In some embodiments of any of the aspects, the cell penetration motif can be N-terminal or C-terminal with respect to the at least one nucleophosmin-binding domain, e.g., to the nuclephosmin-binding domain. In some embodiments of any of the aspects, the polypeptide further comprises an N-terminal cell penetration motif.

In some embodiments of any of the aspects, the cell penetration motif is a kidney cell penetration motif. Kidney cell penetration motifs are cell penetration motifs effective in crossing the lipid bilayer of kidney cells. In some embodiments of any of the aspects, a kidney cell penetration motif can be a kidney cell-specific penetration motif, e.g., it preferentially or exclusively crosses the lipid bilayer of kidney cells. Exemplary kidney cell penetration motifs include PKKKRKV (SEQ ID NO: 10), RREEERREEERREEEK (SEQ ID NO: 17), and KKRRRKKRRRKKRRRK (SEQ ID NO: 53). In some embodiments of any of the aspects, the cell penetration motif comprises, consists of, or consists essentially of PKKKRKV (SEQ ID NO: 10). In some embodiments of any of the aspects, the cell penetration motif comprises, consists of, or consists essentially of RREEERREEERREEEK (SEQ ID NO: 17). In some embodiments of any of the aspects, the cell penetration motif comprises, consists of, or consists essentially of KKRRRKKRRRKKRRRK (SEQ ID NO: 53).

In some embodiments of any of the aspects, the N-terminal or C-terminal cell penetration motif and the at least one nucleophosmin-binding domain are contiguous. In some embodiments of any of the aspects, the N-terminal or C-terminal cell penetration motif and the at least one nucleophosmin-binding domain are separated by a linker. In some embodiments of any of the aspects, the linker is an alanine residue. In some embodiments of any of the aspects, the linker is a poly-alanine sequence. In some embodiments of any of the aspects, the linker is a beta-alanine residue. In some embodiments of any of the aspects, the linker is a poly-beta-alanine sequence. In some embodiments of any of the aspects, the linker comprises one or more glycine and/or serine residues. In some embodiments of any of the aspects, the linker comprises one or more glycine, proline, and/or serine residues. In some embodiments of any of the aspects, the linker comprises one or more glycine and/or proline residues. In some embodiments of any of the aspects, the linker is a flexible linker. In some embodiments of any of the aspects, the linker has the structure of a beta turn.

In some embodiments of any of the aspects, the cell penetration motif and the at least one nucleophosmin-binding domain are not found in a singular naturally-occuring protein. In some embodiments of any of the aspects, the cell penetration motif comprises a sequence not found in a naturally-occurring BAX protein.

In some embodiments of any of the aspects, the polypeptide comprises, consists of, or consists essentially of a sequence with at least 80%, at least 85%, at least 90%, at least 95%, at least 98%, at least 99%, or greater sequence identity to one of SEQ ID NOs: 18-50 and 66-141. In some embodiments of any of the aspects, the polypeptide comprises, consists of, or consists essentially of a sequence with at least 80% sequence identity to one of SEQ ID NOs: 18-50 and 66-141. In some embodiments of any of the aspects, the polypeptide comprises, consists of, or consists essentially of a sequence with at least 95% sequence identity to one of SEQ ID NOs: 18-50 and 66-141. In some embodiments of any of the aspects, the polypeptide comprises, consists of, or consists essentially of one of SEQ ID NOs: 18-50 and 66-141. In some embodiments of any of the aspects, the polypeptide comprises one of SEQ ID NOs: 18-50 and 66-141.

In some embodiments of any of the aspects, the polypeptide comprises, consists of, or consists essentially of a sequence with at least 80%, at least 85%, at least 90%, at least 95%, at least 98%, at least 99%, or greater sequence identity to one of SEQ ID NOs: 75, 76, 123, 124, 126, 128, 134, 138, and 139. In some embodiments of any of the aspects, the polypeptide comprises, consists of, or consists essentially of a sequence with at least 80% sequence identity to one of SEQ ID NOs: 75, 76, 123, 124, 126, 128, 134, 138, and 139. In some embodiments of any of the aspects, the polypeptide comprises, consists of, or consists essentially of a sequence with at least 95% sequence identity to one of SEQ ID NOs: 75, 76, 123, 124, 126, 128, 134, 138, and 139. In some embodiments of any of the aspects, the polypeptide comprises, consists of, or consists essentially of one of SEQ ID NOs: 75, 76, 123, 124, 126, 128, 134, 138, and 139. In some embodiments of any of the aspects, the polypeptide comprises one of SEQ ID NOs: 75, 76, 123, 124, 126, 128, 134, 138, and 139.

In some embodiments of any of the aspects, the polypeptide comprises, consists of, or consists essentially of a sequence with at least 80%, at least 85%, at least 90%, at least 95%, at least 98%, at least 99%, or greater sequence identity to one of SEQ ID NOs: 123, 138, and 139. In some embodiments of any of the aspects, the polypeptide comprises, consists of, or consists essentially of a sequence with at least 80% sequence identity to one of SEQ ID NOs: 123, 138, and 139. In some embodiments of any of the aspects, the polypeptide comprises, consists of, or consists essentially of a sequence with at least 95% sequence identity to one of SEQ ID NOs: 123, 138, and 139. In some embodiments of any of the aspects, the polypeptide comprises, consists of, or consists essentially of one of SEQ ID NOs: 123, 138, and 139. In some embodiments of any of the aspects, the polypeptide comprises one of SEQ ID NOs: 123, 138, and 139.

In some embodiments of any of the aspects, the polypeptide comprises, consists of, or consists essentially of a sequence with at least 80%, at least 85%, at least 90%, at least 95%, at least 98%, at least 99%, or greater sequence identity to SEQ ID NO: 123. In some embodiments of any of the aspects, the polypeptide comprises, consists of, or consists essentially of a sequence with at least 80% sequence identity to SEQ ID NO: 123. In some embodiments of any of the aspects, the polypeptide comprises, consists of, or consists essentially of a sequence with at least 95% sequence identity to SEQ ID NO: 123. In some embodiments of any of the aspects, the polypeptide comprises, consists of, or consists essentially of SEQ ID NO: 123. In some embodiments of any of the aspects, the polypeptide comprises SEQ ID NO: 123.

In some embodiments of any of the aspects, the polypeptide comprises, consists of, or consists essentially of a sequence with at least 80%, at least 85%, at least 90%, at least 95%, at least 98%, at least 99%, or greater sequence identity to SEQ ID NO: 138. In some embodiments of any of the aspects, the polypeptide comprises, consists of, or consists essentially of a sequence with at least 80% sequence identity to SEQ ID NO: 138. In some embodiments of any of the aspects, the polypeptide comprises, consists of, or consists essentially of a sequence with at least 95% sequence identity to SEQ ID NO: 138. In some embodiments of any of the aspects, the polypeptide comprises, consists of, or consists essentially of SEQ ID NO: 138. In some embodiments of any of the aspects, the polypeptide comprises SEQ ID NO: 138.

In some embodiments of any of the aspects, the polypeptide comprises, consists of, or consists essentially of a sequence with at least 80%, at least 85%, at least 90%, at least 95%, at least 98%, at least 99%, or greater sequence identity to SEQ ID NO: 139. In some embodiments of any of the aspects, the polypeptide comprises, consists of, or consists essentially of a sequence with at least 80% sequence identity to SEQ ID NO: 139. In some embodiments of any of the aspects, the polypeptide comprises, consists of, or consists essentially of a sequence with at least 95% sequence identity to SEQ ID NO: 139. In some embodiments of any of the aspects, the polypeptide comprises, consists of, or consists essentially of SEQ ID NO: 139. In some embodiments of any of the aspects, the polypeptide comprises SEQ ID NO: 139.

As described herein, the instant polypeptides inhibit kidney cell death, e.g., regulated or "programmed" kidney cell death. The polypeptides are therefore contemplated for use in treating acute kidney injury, including acute kidney injury caused by ischemic injury.

In one aspect of any of the embodiments, described herein is a method of treating acute kidney injury in a subject in need thereof, the method comprising administering a polypeptide described herein to the subject. As used herein "acute kidney injury" refers to a sudden failure in kidney function. Methods of diagnosing acute kidney injury are known in the art, e.g., Ostermann et al. Crit Care 2016 20:299; which is incorporated by reference herein in its entirety. Acute kidney injury can be diagnosed by measuring urine output, serum creatinine, BUN, and/or glomular filtration rate.

Acute kidney injury often arises as a consequence of a primary illness, e.g., chronic kidney disease, heart failure, liver disease, diabetes, infection/sepsis, or urinary tract blockage. In some embodiments of any of the aspects, the subject in need of treatment for acute kidney injury is a subject with chronic kidney disease, heart failure, liver disease, diabetes, infection/sepsis, or urinary tract blockage. In some embodiments of any of the aspects, the subject in need of treatment for acute kidney injury is a subject with chronic kidney disease, heart failure, liver disease, diabetes, infection/sepsis, or urinary tract blockage that increases the risk of AKI.

In some embodiments of any of the aspects, the treatment is prophylactic, e.g., with respect to kidney cell death, serum creatinine increases, serum potassium increases, and/or a need for dialysis. In some embodiments of any of the aspects, the treatment is prophylactic, e.g., with respect to progression to stage II or stage III acute kidney injury. In some embodiments of any of the aspects, the treatment is prophylactic, e.g., with respect to a fall in urine utput and/or an increase in serum creatinine. In some embodiments of any of the aspects, the treatment is prophylactic, e.g., with respect to an increase in serum creatinine of 1.5× or more in a 7-day period. In some embodiments of any of the aspects, the treatment is prophylactic, e.g., with respect to an increase in serum creatinine of 2.0× or more in a 7-day period. In some embodiments of any of the aspects, the treatment is prophylactic, e.g., with respect to an increase in serum creatinine of 0.3 mg/dL or more in a 48-hour period. In some embodiments of any of the aspects, the subject is at risk for developing acute kidney injury and has not yet exhibited kidney cell death, serum creatinine increases, serum potassium increases, and/or a need for dialysis.

In some embodiments of any of the aspects, the subject has a serum creatinine level of no more than 1.3 mg/dL (114.9 μmol/L) for male subject, and no more than 1.1 mg/dL (97.2 μmol/L) for female subject when administration begins. In some embodiments of any of the aspects, the subject has a serum creatinine level of less than 4.0 mg/dL (354 μmol/L) when administration begins. In some embodiments of any of the aspects, the subject has a blood urea nitrogen (BUN) level of no more than 20 when administration begins.

In one aspect of any of the embodiments, described herein is a method of treating ischemia in subject in need thereof, the method comprising administering a polypeptide described herein to the subject. In some embodiments of any of the aspects, the subject is a post-operative cardiac surgery patient. In some embodiments of any of the aspects, the subject is a pre-cardiac surgery patient. In some embodiments of any of the aspects, the subject is a cardiac surgery patient.

The compositions and methods described herein can be administered to a subject having or diagnosed as having acute kidney injury, ischemia, and/or ischemic injury. In some embodiments, the methods described herein comprise administering an effective amount of compositions described herein, e.g., a polypeptide described herein to a subject in order to alleviate a symptom of acute kidney injury. As used herein, "alleviating a symptom" of a condition is ameliorating any condition or symptom associated with the condition. As compared with an equivalent untreated control, such reduction is by at least 5%, 10%, 20%, 40%, 50%, 60%, 80%, 90%, 95%, 99% or more as measured by any standard technique. A variety of means for administering the compositions described herein to subjects are known to those of skill in the art. Such methods can include, but are not limited to oral, parenteral, intravenous, intramuscular, subcutaneous, transdermal, airway (aerosol), pulmonary, cutaneous, topical or injection administration. Administration can be local or systemic.

The term "effective amount" as used herein refers to the amount of the polypeptide described herein needed to alleviate at least one or more symptom of the disease or disorder, and relates to a sufficient amount of pharmacological composition to provide the desired effect. The term "therapeutically effective amount" therefore refers to an amount of the polypeptide described herein that is sufficient to provide a particular anti-cell death effect when administered to a typical subject. An effective amount as used herein, in various contexts, would also include an amount sufficient to delay the development of a symptom of the disease, alter the course of a symptom disease (for example but not limited to, slowing the progression of a symptom of the disease), or reverse a symptom of the disease. Thus, it is not generally practicable to specify an exact "effective amount". However, for any given case, an appropriate "effective amount" can be determined by one of ordinary skill in the art using only routine experimentation.

Effective amounts, toxicity, and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dosage can vary depending upon the dosage form employed and the route of administration utilized. The dose ratio between toxic and therapeutic effects is the therapeutic index and can be expressed as the ratio LD50/

ED50. Compositions and methods that exhibit large therapeutic indices are preferred. A therapeutically effective dose can be estimated initially from cell culture assays. Also, a dose can be formulated in animal models to achieve a circulating plasma concentration range that includes the IC50 (i.e., the concentration of the polypeptide described herein, which achieves a half-maximal inhibition of symptoms) as determined in cell culture, or in an appropriate animal model. Levels in plasma can be measured, for example, by high performance liquid chromatography. The effects of any particular dosage can be monitored by a suitable bioassay, e.g., serum creatinine or a MTT cell survival assay, among others. The dosage can be determined by a physician and adjusted, as necessary, to suit observed effects of the treatment.

In some embodiments, the technology described herein relates to a pharmaceutical composition comprising a polypeptide as described herein, and optionally a pharmaceutically acceptable carrier. In some embodiments, the active ingredients of the pharmaceutical composition comprise a polypeptide as described herein. In some embodiments, the active ingredients of the pharmaceutical composition consist essentially of a polypeptide as described herein. In some embodiments, the active ingredients of the pharmaceutical composition consists of a polypeptide as described herein. Pharmaceutically acceptable carriers and diluents include saline, aqueous buffer solutions, solvents and/or dispersion media. The use of such carriers and diluents is well known in the art. Some non-limiting examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein. In some embodiments, the carrier inhibits the degradation of the active agent, e.g., a polypeptide as described herein.

In some embodiments, the pharmaceutical composition comprising a polypeptide as described herein can be a parenteral dose form. Since administration of parenteral dosage forms typically bypasses the patient's natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions. In addition, controlled-release parenteral dosage forms can be prepared for administration of a patient, including, but not limited to, DUROS®-type dosage forms and dose-dumping.

Suitable vehicles that can be used to provide parenteral dosage forms of a polypeptide as disclosed within are well known to those skilled in the art. Examples include, without limitation: sterile water; water for injection USP; saline solution; glucose solution; aqueous vehicles such as but not limited to, sodium chloride injection, Ringer's injection, dextrose injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate. Compounds that alter or modify the solubility of a pharmaceutically acceptable salt of a polypeptide as disclosed herein can also be incorporated into the parenteral dosage forms of the disclosure, including conventional and controlled-release parenteral dosage forms.

Pharmaceutical compositions comprising a polypeptide as described herein can also be formulated to be suitable for oral administration, for example as discrete dosage forms, such as, but not limited to, tablets (including without limitation scored or coated tablets), pills, caplets, capsules, chewable tablets, powder packets, cachets, troches, wafers, aerosol sprays, or liquids, such as but not limited to, syrups, elixirs, solutions or suspensions in an aqueous liquid, a non-aqueous liquid, an oil-in-water emulsion, or a water-in-oil emulsion. Such compositions contain a predetermined amount of the pharmaceutically acceptable salt of the disclosed compounds, and may be prepared by methods of pharmacy well known to those skilled in the art. See generally, Remington: The Science and Practice of Pharmacy, 21st Ed., Lippincott, Williams, and Wilkins, Philadelphia PA. (2005).

Conventional dosage forms generally provide rapid or immediate drug release from the formulation. Depending on the pharmacology and pharmacokinetics of the drug, use of conventional dosage forms can lead to wide fluctuations in the concentrations of the drug in a patient's blood and other tissues. These fluctuations can impact a number of parameters, such as dose frequency, onset of action, duration of efficacy, maintenance of therapeutic blood levels, toxicity, side effects, and the like. Advantageously, controlled-release formulations can be used to control a drug's onset of action, duration of action, plasma levels within the therapeutic window, and peak blood levels. In particular, controlled- or extended-release dosage forms or formulations can be used to ensure that the maximum effectiveness of a drug is achieved while minimizing potential adverse effects and safety concerns, which can occur both from under-dosing a drug (i.e., going below the minimum therapeutic levels) as well as exceeding the toxicity level for the drug. In some embodiments, the polypeptide as described herein can be administered in a sustained release formulation.

Controlled-release pharmaceutical products have a common goal of improving drug therapy over that achieved by their non-controlled release counterparts. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. Kim, Cherng-ju, Controlled Release Dosage Form Design, 2 (Technomic Publishing, Lancaster, Pa.: 2000).

Most controlled-release formulations are designed to initially release an amount of drug (active ingredient) that promptly produces the desired therapeutic effect, and gradually and continually release other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, ionic strength, osmotic pressure, temperature, enzymes, water, and other physiological conditions or compounds.

A variety of known controlled- or extended-release dosage forms, formulations, and devices can be adapted for use with the salts and compositions of the disclosure. Examples include, but are not limited to, those described in U.S. Pat. Nos. 3,845,770; 3,916,899; 3,536,809; 3,598,123; 4,008,719; 5674,533; 5,059,595; 5,591,767; 5,120,548; 5,073,543; 5,639,476; 5,354,556; 5,733,566; and 6,365,185 B1; each of which is incorporated herein by reference. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), or a combination thereof to provide the desired release profile in varying proportions.

Im some embodiments of any of the aspects, the polypeptide as described herein described herein is administered as a monotherapy, e.g., another treatment for the acute kidney injury and/or ischemia is not administered to the subject.

In some embodiments of any of the aspects, the methods described herein can further comprise administering a second agent and/or treatment to the subject, e.g., as part of a combinatorial therapy. Non-limiting examples of a second agent and/or treatment can include dialysis.

In certain embodiments, an effective dose of a composition comprising a polypeptide as described herein as described herein can be administered to a patient once. In certain embodiments, an effective dose of a composition comprising a polypeptide as described herein can be repeatedly administered to a patient. For systemic administration, subjects can be administered a therapeutic amount of a composition comprising a polypeptide as described herein, such as, e.g., 0.001 mg/kg, 0.01 mg/kg, 0.1 mg/kg, 0.5 mg/kg, 1.0 mg/kg, 2.0 mg/kg, 2.5 mg/kg, 5 mg/kg, 10 mg/kg, 15 mg/kg, 20 mg/kg, 25 mg/kg, 30 mg/kg, 40 mg/kg, 50 mg/kg, or more.

In some embodiments, after an initial treatment regimen, the treatments can be administered on a less frequent basis. For example, after treatment weekly for three months, treatment can be repeated once per month, for six months or a year or longer. Treatment according to the methods described herein can reduce levels of a marker or symptom of a condition, e.g., serum creatinine, GFR, or BUN by at least 10%, at least 15%, at least 20%, at least 25%, at least 30%, at least 40%, at least 50%, at least 60%, at least 70%, at least 80% or at least 90% or more. In some embodiments of any of the aspects, the marker or a condition can be one or more AKI biomarkers. Such biomarkers are known in the art, e.g., NGAL, KIM1, IL-18, L-FABP, alanine aminopeptidase, calprotectin, CMCL14, Chitinase 3-like protein 1, cystatin C, Dickkopf-3, alpha GST, pi GST, HGF, hepcidin, insulin-like growth factor binding protein 7, tissue metalloproteinase 2, monocyte chemoattractnt peptide 1, n-acetyl-beta-D-glucosaminidase, netrin 1, osteopontin, proenkephalin A, retinol binding protein, and TNF. Such biomarkers are discussed further in Alge et al. Clinical Jouirnal of the American Society of Nephrology 10:147-155 (2015); Bhosale et al. Indian J Crit Care Med 24:S90-93 (2020), and Ostermann et al. JAMA Netw Open 3:e2019209 (2020); each of which is incorporated by reference herein in its entirety. Commerical AKI biomarker assays are available, e.g., NephroCheck™ (BioMerieux; Cambridge, MA).

The dosage of a composition as described herein can be determined by a physician and adjusted, as necessary, to suit observed effects of the treatment. With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment, or make other alterations to the treatment regimen. The dosing schedule can vary from once a week to daily depending on a number of clinical factors, such as the subject's sensitivity to the polypeptide as described herein. The desired dose or amount of activation can be administered at one time or divided into subdoses, e.g., 2-4 subdoses and administered over a period of time, e.g., at appropriate intervals through the day or other appropriate schedule. In some embodiments, administration can be chronic, e.g., one or more doses and/or treatments daily over a period of weeks or months. Examples of dosing and/or treatment schedules are administration daily, twice daily, three times daily or four or more times daily over a period of 1 week, 2 weeks, 3 weeks, 4 weeks, 1 month, 2 months, 3 months, 4 months, 5 months, or 6 months, or more. A composition comprising a polypeptide as described herein can be administered over a period of time, such as over a 5 minute, 10 minute, 15 minute, 20 minute, or 25 minute period.

The dosage ranges for the administration of a polypeptide as described herein, according to the methods described herein depend upon, for example, the form of the polypeptide as described herein, its potency, and the extent to which symptoms, markers, or indicators of a condition described herein are desired to be reduced, for example the percentage reduction desired for a reduction in serum creatinine, GFR, or BUN or the extent to which, for example, urine production is desired to be induced. The dosage should not be so large as to cause adverse side effects. Generally, the dosage will vary with the age, condition, and sex of the patient and can be determined by one of skill in the art. The dosage can also be adjusted by the individual physician in the event of any complication.

The efficacy of a polypeptide as described herein in, e.g., the treatment of a condition described herein, or to induce a response as described herein (e.g., inhibition of cell death) can be determined by the skilled clinician. However, a treatment is considered "effective treatment," as the term is used herein, if one or more of the signs or symptoms of a condition described herein are altered in a beneficial manner, other clinically accepted symptoms are improved, or even ameliorated, or a desired response is induced e.g., by at least 10% following treatment according to the methods described herein. Efficacy can be assessed, for example, by measuring a marker, indicator, symptom, and/or the incidence of a condition treated according to the methods described herein or any other measurable parameter appropriate, e.g., serum creatinine, GFR, BUN, or renal cell survival/cell death (e.g., by MTT cell survival assay). Efficacy can also be measured by a failure of an individual to worsen as assessed by hospitalization, or need for medical interventions (i.e., progression of the disease is halted). Methods of measuring these indicators are known to those of skill in the art and/or are described herein. Treatment includes any treatment of a disease in an individual or an animal (some non-limiting examples include a human or an animal) and includes: (1) inhibiting the disease, e.g., preventing a worsening of symptoms (e.g., serum creatinine, GFR, BUN, or renal cell survival/cell death (e.g., by MTT cell survival assay); or (2) relieving the severity of the disease, e.g., causing regression of symptoms. An effective amount for the treatment of a disease means that amount which, when administered to a subject in need thereof, is sufficient to result in effective treatment as that term is defined herein, for that disease. Efficacy of an agent can be determined by assessing physical indicators of a condition or desired response, (e.g., serum creatinine, GFR, BUN, or primary kidney cell survival/cell death (e.g., by MTT cell survival assay). It is well within the ability of one skilled in the art to monitor efficacy of administration and/or treatment by measuring any one of such parameters, or any combination of parameters. Efficacy can be assessed in animal models of a condition described herein, for example treatment of acute kidney injury or ischemia. When using an experimental animal model, efficacy of treatment is evidenced when a statistically significant change in a marker is observed, e.g., serum creatinine, GFR, BUN, or an AKI biomarker (e.g, NephroCheck™).

In vitro and animal model assays are provided herein which allow the assessment of a given dose of a polypeptide as described herein. By way of non-limiting example, the effects of a dose of a polypeptide as described herein can be assessed by serum creatinine, GFR, BUN, or kidney cell survival/cell death (e.g., by MTT cell survival assay).

As described herein, a subject treated in accordance with the methods described herein can be a subject with an increased level of NPM1. In some embodiments of any of the aspects, a subject treated in accordance with the methods described herein can be a subject with an increased level of urinary NPM1 (total) and/or one of its toxic, phosphorylated metabolites detected by mass spectrometry including p-$S^{86}$, p-$S^{88}$ and p-$T^{95}$ NPM1 (ref: Wang, Z et. al. JASN, 2019; Wang, Z et al. 2020 AJP (renal), which is incorporated by reference herein in its entirety). Accordingly, in one aspect of any of the embodiments, described herein is a method of treating actue kidney injury and/or ischemia in a subject in need thereof, the method comprising administering a polypeptide as described herein to a subject determined to have a level of NPM1 that is increased relative to a reference. In one aspect of any of the embodiments, described herein is a method of treating acute kidney injury and/or ischemia in a subject in need thereof, the method comprising: a) determining the level of NPM1 (e.g., urinary NPM1 and/or its phosphorylated metabolites) in a sample obtained from a subject; and b) administering a polypeptide as described herein to the subject if the level of NPM1 (e.g., urinary NPM1 and/or its phosphorylated metabolites) is increased relative to a reference. In some embodiments of any of the aspects, the method comprises administering a polypeptide as described herein to a subject previously determined to have a level of of NPM1 (e.g., urinary NPM1 and/or its phosphorylated metabolites) that is increased relative to a reference. In some embodiments of any of the aspects, described herein is a method of treating actue kidney injury and/or ischemia in a subject in need thereof, the method comprising: a) first determining the level of of NPM1 (e.g., urinary NPM1 and/or its phosphorylated metabolites) in a sample obtained from a subject; and b) then administering a polypeptide as described herein to the subject if the level of NPM1 is increased relative to a reference.

In some embodiments of any of the aspects, the step of determining if the subject has an increased level of of NPM1 (e.g., urinary NPM1 and/or its phosphorylated metabolites) can comprise i) obtaining or having obtained a sample from the subject and ii) performing or having performed an assay on the sample obtained from the subject to determine/measure the level of NPM1 (e.g., urinary NPM1 and/or its phosphorylated metabolites) in the subject. In some embodiments of any of the aspects, the step of determining if the subject has an incresaed level of of NPM1 (e.g., urinary NPM1 and/or its phosphorylated metabolites) can comprise performing or having performed an assay on a sample obtained from the subject to determine/measure the level of of NPM1 (e.g., urinary NPM1 and/or its phosphorylated metabolites) in the subject. In some embodiments of any of the aspects, the step of determining if the subject has an increased level of of NPM1 (e.g., urinary NPM1 and/or its phosphorylated metabolites) can comprise ordering or requesting an assay on a sample obtained from the subject to determine/measure the level of of NPM1 (e.g., urinary NPM1 and/or its phosphorylated metabolites) in the subject. In some embodiments of any of the aspects, the step of determining if the subject has an increased level of of NPM1 (e.g., urinary NPM1 and/or its phosphorylated metabolites) can comprise receiving the results of an assay on a sample obtained from the subject to determine/measure the level of of NPM1 (e.g., urinary NPM1 and/or its phosphorylated metabolites) in the subject. In some embodiments of any of the aspects, the step of determining if the subject has an increased level of of NPM1 (e.g., urinary NPM1 and/or its phosphorylated metabolites) can comprise receiving a report, results, or other means of identifying the subject as a subject with an increased level of NPM1. In some embodiments of any of the aspects, the step of instructing or directing that the subject be administered a particular treatment can comprise providing a report of the assay results. In some embodiments of any of the aspects, the step of instructing or directing that the subject be administered a particular treatment can comprise providing a report of the assay results and/or treatment recommendations in view of the assay results.

In some embodiments of any of the aspects, the level of NPM1 is the level of urinary NPM1 and/or its phosphorylated metabolites. In some embodiments of any of the aspects, the level of NPM1 is the level of urinary NPM1.

In some embodiments of any of the aspects, measurement of the level of a target and/or detection of the level or presence of a target, e.g., of an expression product (nucleic acid or polypeptide of one of the genes described herein) or a mutation can comprise a transformation. As used herein, the term "transforming" or "transformation" refers to changing an object or a substance, e.g., biological sample, nucleic acid or protein, into another substance. The transformation can be physical, biological or chemical. Exemplary physical transformation includes, but is not limited to, pre-treatment of a biological sample, e.g., from whole blood to blood serum by differential centrifugation. A biological/chemical transformation can involve the action of at least one enzyme and/or a chemical reagent in a reaction. For example, a DNA sample can be digested into fragments by one or more restriction enzymes, or an exogenous molecule can be attached to a fragmented DNA sample with a ligase. In some embodiments of any of the aspects, a DNA sample can undergo enzymatic replication, e.g., by polymerase chain reaction (PCR).

Transformation, measurement, and/or detection of a target molecule, e.g., an NPM1 mRNA or polypeptide can comprise contacting a sample obtained from a subject with a reagent (e.g., a detection reagent) which is specific for the target, e.g., a target-specific reagent. In some embodiments of any of the aspects, the target-specific reagent is detectably labeled. In some embodiments of any of the aspects, the target-specific reagent is capable of generating a detectable signal. In some embodiments of any of the aspects, the target-specific reagent generates a detectable signal when the target molecule is present.

Methods to measure gene expression products are known to a skilled artisan. Such methods to measure gene expression products, e.g., protein level, include ELISA (enzyme linked immunosorbent assay), western blot, immunoprecipitation, and immunofluorescence using detection reagents such as an antibody or protein binding agents. Alternatively, a polypeptide can be detected in a subject by introducing into a subject a labeled anti-peptide antibody and other types of detection agent. For example, the antibody can be labeled with a detectable marker whose presence and location in the subject is detected by standard imaging techniques. Polypeptide levels can be detected by, e.g., immunohistochemistry ("IHC"), immunocytochemistry ("ICC") Western blot analysis, two-dimensional gel electrophoresis systems, radioimmunoassay (RIA), ELISA (enzyme linked immunosorbent assay), "sandwich" immunoassays, immunoprecipitation assays, immunodiffusion assays, agglutination assays, e.g., latex agglutination, complement-fixation assays, immunoradiometric assays, fluorescent immunoassays, e.g. FIA (fluorescence-linked immunoassay), chemiluminescence immunoassays (CLIA), electrochemiluminescence immunoassay (ECLIA, counting immunoassay (CIA), lateral flow tests or immunoassay (LFIA), magnetic immunoassay (MIA), and protein A immunoassays. Methods for performing such assays are known in the art.

In certain embodiments, the gene expression products as described herein can be instead determined by determining the level of messenger RNA (mRNA) expression of the genes described herein. Such molecules can be isolated, derived, or amplified from a biological sample, such as a blood sample. Techniques for the detection of mRNA expression is known by persons skilled in the art, and can include but not limited to, PCR procedures, RT-PCR, quantitative RT-PCR Northern blot analysis, differential gene expression, RNAse protection assay, microarray based analysis, next-generation sequencing; hybridization methods, quantitative sequencing technology, or a quantitative next-generation sequence technology. In some next-generation technologies, an adaptor (double or single-stranded) is ligated to nucleic acid molecules in the sample and synthesis proceeds from the adaptor or adaptor compatible primers. In some third-generation technologies, the sequence can be determined, e.g., by determining the location and pattern of the hybridization of probes, or measuring one or more characteristics of a single molecule as it passes through a sensor (e.g., the modulation of an electrical field as a nucleic acid molecule passes through a nanopore). Exemplary methods of sequencing include, but are not limited to, Sanger sequencing, dideoxy chain termination, high-throughput sequencing, next generation sequencing, 454 sequencing, SOLiD sequencing, polony sequencing, Illumina sequencing, Ion Torrent sequencing, sequencing by hybridization, nanopore sequencing, Helioscope sequencing, single molecule real time sequencing, RNAP sequencing, and the like. Methods and protocols for performing these sequencing methods are known in the art, see, e.g. "Next Generation Genome Sequencing" Ed. Michal Janitz, Wiley-VCH; "High-Throughput Next Generation Sequencing" Eds. Kwon and Ricke, Humanna Press, 2011; and Sambrook et al., Molecular Cloning: A Laboratory Manual (4 ed.), Cold Spring Harbor Laboratory Press, Cold Spring Harbor, N.Y., USA (2012); which are incorporated by reference herein in their entireties.

In some embodiments of any of the aspects, one or more of the reagents (e.g., an antibody reagent and/or nucleic acid probe) described herein can comprise a detectable label and/or comprise the ability to generate a detectable signal (e.g., by catalyzing reaction converting a compound to a detectable product). Detectable labels can comprise, for example, a light-absorbing dye, a fluorescent dye, or a radioactive label. Detectable labels, methods of detecting them, and methods of incorporating them into reagents (e.g., antibodies and nucleic acid probes) are well known in the art.

A level which is more than a reference level can be a level which is greater by at least about 10%, at least about 20%, at least about 50%, at least about 60%, at least about 80%, at least about 90%, at least about 100%, at least about 200%, at least about 300%, at least about 500% or more than the reference level. In some embodiments of any of the aspects, a level which is more than a reference level can be a level which is statistically significantly greater than the reference level.

In some embodiments of any of the aspects, the reference can be a level of the target molecule in a population of subjects who do not have or are not diagnosed as having, and/or do not exhibit signs or symptoms of actue kidney injury and/or ischemia. In some embodiments of any of the aspects, the reference can also be a level of expression of the target molecule in a control sample, a pooled sample of control individuals or a numeric value or range of values based on the same. In some embodiments of any of the aspects, the reference can be the level of a target molecule in a sample obtained from the same subject at an earlier point in time, e.g., the methods described herein can be used to determine if a subject's sensitivity or response to a given therapy is changing over time.

In some embodiments of any of the aspects, the level of expression products of no more than 200 other genes is determined. In some embodiments of any of the aspects, the level of expression products of no more than 100 other genes is determined. In some embodiments of any of the aspects, the level of expression products of no more than 20 other genes is determined. In some embodiments of any of the aspects, the level of expression products of no more than 10 other genes is determined.

In some embodiments of the foregoing aspects, the expression level of a given gene can be normalized relative to the expression level of one or more reference genes or reference proteins.

In some embodiments, the reference level can be the level in a sample of similar cell type, sample type, sample processing, and/or obtained from a subject of similar age, sex and other demographic parameters as the sample/subject for which the level of NPM1 is to be determined. In some embodiments, the test sample and control reference sample are of the same type, that is, obtained from the same biological source, and comprising the same composition, e.g., the same number and type of cells.

The term "sample" or "test sample" as used herein denotes a sample taken or isolated from a biological organism, e.g., a blood or plasma sample from a subject. In some embodiments of any of the aspects, the present invention encompasses several examples of a biological sample. In some embodiments of any of the aspects, the biological sample is cells, or tissue, or peripheral blood, or bodily fluid. Exemplary biological samples include, but are not limited to, a biopsy, a tumor sample, biofluid sample; blood; serum; plasma; urine; sperm; mucus; tissue biopsy; organ biopsy; synovial fluid; bile fluid; cerebrospinal fluid; mucosal secretion; effusion; sweat; saliva; and/or tissue sample etc. The term also includes a mixture of the above-mentioned samples. The term "test sample" also includes untreated or pretreated (or pre-processed) biological samples. In some embodiments of any of the aspects, a test sample can comprise cells from a subject.

The test sample can be obtained by removing a sample from a subject, but can also be accomplished by using a previously isolated sample (e.g., isolated at a prior timepoint and isolated by the same or another person).

In some embodiments of any of the aspects, the test sample can be an untreated test sample. As used herein, the phrase "untreated test sample" refers to a test sample that has not had any prior sample pre-treatment except for dilution and/or suspension in a solution. Exemplary methods for treating a test sample include, but are not limited to, centrifugation, filtration, sonication, homogenization, heating, freezing and thawing, and combinations thereof. In some embodiments of any of the aspects, the test sample can be a frozen test sample, e.g., a frozen tissue. The frozen sample can be thawed before employing methods, assays and systems described herein. After thawing, a frozen sample can be centrifuged before being subjected to methods, assays and systems described herein. In some embodiments of any of the aspects, the test sample is a clarified test sample, for example, by centrifugation and collection of a supernatant comprising the clarified test sample. In some embodiments of any of the aspects, a test sample can be a pre-processed test sample, for example, supernatant or filtrate resulting from a treatment selected from the group consisting of centrifugation, filtration, thawing, purification, and any combinations thereof. In some embodiments of any of the aspects, the test sample can be treated with a chemical and/or biological reagent. Chemical and/or biological reagents can be employed to protect and/or maintain the stability of the sample, including biomolecules (e.g., nucleic acid and protein) therein, during processing. One exemplary reagent is a protease inhibitor, which is generally used to protect or maintain the stability of protein during processing. The skilled artisan is well aware of methods and processes appropriate for pre-processing of biological samples required for determination of the level of an expression product as described herein.

In some embodiments of any of the aspects, the methods, assays, and systems described herein can further comprise a step of obtaining or having obtained a test sample from a subject. In some embodiments of any of the aspects, the subject can be a human subject. In some embodiments of any of the aspects, the subject can be a subject in need of treatment for (e.g., having or diagnosed as having) actue kidney injury and/or ischemia or a subject at risk of or at increased risk of developing actue kidney injury and/or ischemia as described elsewhere herein.

In some embodiments, the technology described herein relates to a nucleic acid encoding a polypeptide as described herein, e.g., a polypeptide comprising at least one nucleophosmin-binding binding domain as described herein. In some embodiments, the nucleic acid is a cDNA.

In some embodiments, a nucleic acid encoding a polypeptide as described herein is comprised by a vector. In some of the aspects described herein, a nucleic acid sequence encoding a polypeptide, is operably linked to a vector.

A nucleic acid molecule, such as DNA, is said to be "capable of expressing" a polypeptide if it contains nucleotide sequences which contain transcriptional and translational regulatory information and such sequences are "operably linked" to nucleotide sequences which encode the polypeptide. An operable linkage is a linkage in which the regulatory DNA sequences and the DNA sequence sought to be expressed are connected in such a way as to permit gene expression as polypeptides in recoverable amounts. The precise nature of the regulatory regions needed for gene expression may vary from organism to organism, as is well known in the analogous art.

In one aspect of any of the embodiments, described herein is a cell comprising an a polypeptide as described herein, or a nucleic acid encoding such a polypeptide. The cell can be either a prokaryotic or eukaryotic cell. In some embodiments, the nucleotide sequence is incorporated into a plasmid or viral vector capable of autonomous replication in the recipient cell. Any of a wide variety of vectors can be employed for this purpose and are known and available to those or ordinary skill in the art. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species.

In some embodiments, the composition a polypeptide as described herein or a nucleic acid encoding polypeptide as described herein can be a lyophilisate.

In some embodiments, the technology described herein relates to a syringe or catheter, including an organ-specific catheter (e.g., renal arterial, venous, or bladder catheter etc.), comprising a therapeutically effective amount of a composition described herein.

In one aspect, described herein is a kit comprising a composition as described herein, e.g., a composition comprising a polypeptide as described herein. A kit is any manufacture (e.g., a package or container) comprising at least one reagent, e.g., a polypeptide, the manufacture being promoted, distributed, or sold as a unit for performing the methods described herein. The exact nature of the components configured in the kit depends on its intended purpose. In some embodiments of any of the aspects, a kit includes instructions for use. "Instructions for use" typically include a tangible expression describing the technique to be employed in using the components of the kit, e.g., to treat a subject with acute kidney injury or at risk of developing AKI. Still in accordance with the present invention, "instructions for use" may include a tangible expression describing the preparation of at least one reagent described herein, such as dilution, mixing, or dosing instructions, and the like, typically for an intended purpose. Optionally, the kit also contains other useful components, such as, measuring tools, diluents, buffers, syringes, pharmaceutically acceptable carriers, or other useful paraphernalia as will be readily recognized by those of skill in the art.

The materials or components assembled in the kit can be provided to the practitioner stored in any convenient and suitable ways that preserve their operability and utility. For example, the components can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as inventive compositions and the like. The packaging material is constructed by well-known methods, preferably to provide a sterile, contaminant-free environment. The packaging may also preferably provide an environment that protects from light, humidity, and oxygen. As used herein, the term "package" refers to a suitable solid matrix or material such as glass, plastic, paper, foil, polyester (such as polyethylene terephthalate, or Mylar) and the like, capable of holding the individual kit components. Thus, for example, a package can be a glass vial used to contain suitable quantities of a composition containing a volume of at least one reagent described herein. The packaging material generally has an external label which indicates the contents and/or purpose of the kit and/or its components.

In one respect, the present invention relates to the herein described compositions, methods, and respective component(s) thereof, as essential to the technology, yet open to the inclusion of unspecified elements, essential or not ("comprising). In some embodiments of any of the aspects, other elements to be included in the description of the composition, method or respective component thereof are limited to those that do not materially affect the basic and novel characteristic(s) of the technology (e.g., the composition, method, or respective component thereof "consists essentially of" the elements described herein). This applies equally to steps within a described method as well as compositions and components therein. In other embodiments of any of the aspects, the compositions, methods, and respective components thereof, described herein are intended to be exclusive of any element not deemed an essential element to the component, composition or method (e.g., the composition, method, or respective component thereof "consists of" the elements described herein). This applies equally to steps within a described method as well as compositions and components therein.

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

For convenience, certain terms employed herein, in the specification, examples and appended claims are collected here.

The terms "decrease", "reduced", "reduction", or "inhibit" are all used herein to mean a decrease by a statistically significant amount. In some embodiments, "reduce," "reduction" or "decrease" or "inhibit" typically means a decrease by at least 10% as compared to a reference level (e.g., the absence of a given treatment or agent) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal for an individual without a given disorder.

The terms "increased", "increase", "enhance", or "activate" are all used herein to mean an increase by a statically significant amount. In some embodiments, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker or symptom, an "increase" is a statistically significant increase in such level.

As used herein, a "subject" means a human or animal. Usually the animal is a vertebrate such as a primate, rodent, domestic animal or game animal. Primates include chimpanzees, cynomologus monkeys, spider monkeys, and macaques, e.g., *Rhesus* species. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In some embodiments, the subject is a mammal, e.g., a primate, e.g., a human. The terms, "individual," "patient" and "subject" are used interchangeably herein.

Preferably, the subject is a mammal. The mammal can be a human, non-human primate, mouse, rat, dog, cat, horse, or cow, but is not limited to these examples. Mammals other than humans can be advantageously used as subjects that represent animal models of acute kidney injury and/or ischemia. A subject can be male or female.

A subject can be one who has been previously diagnosed with or identified as suffering from or having a condition in need of treatment (e.g., acute kidney injury and/or ischemia) or one or more complications related to such a condition, and optionally, have already undergone treatment for the condition or the one or more complications related to the condition. Alternatively, a subject can also be one who has not been previously diagnosed as having the condition or one or more complications related to the condition. For example, a subject can be one who exhibits one or more risk factors for the condition or one or more complications related to the condition or a subject who does not exhibit risk factors.

A "subject in need" of treatment for a particular condition can be a subject having that condition, diagnosed as having that condition, or at risk of developing that condition.

As used herein, the terms "protein" and "polypeptide" are used interchangeably herein to designate a series of amino acid residues, connected to each other by peptide bonds between the alpha-amino and carboxy groups of adjacent residues. The terms "protein", and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing. The terms also refer to fragments or variants of the polypeptide that maintain at least 50% of the activity or effect, e.g., NPM1-binding activity of the reference polypeptide of SEQ ID NO: 1. Conservative substitution variants that maintain the activity of the reference polypeptide of SEQ ID NO: Twill include a conservative substitution as defined herein. The identification of amino acids most likely to be tolerant of conservative substitution while maintaining at least 50% of the activity of the reference polypeptide of SEQ ID NO: 1 is described herein. Amino acids that are specified in the consensus sequences provided herein are less likely to tolerate change, while those indicated by "X" are obviously much more likely to tolerate change, including conservative change, in the context of a variant. Variants, fragments, and/or fusion proteins can be tested for activity, for example, by administering the variant to an appropriate animal model of acute kidney injury as described herein.

In some embodiments, a polypeptide can be a variant of a sequence described herein, e.g., a variant of a polypeptide comprising the amino acid sequence of any one of SEQ ID NOs: 2-9 and 11-14. In some embodiments, the variant is a conservative substitution variant. Variants can be obtained by mutations of native nucleotide sequences, for example. A "variant," as referred to herein, is a polypeptide substantially homologous to a native or reference polypeptide, but which has an amino acid sequence different from that of the native or reference polypeptide because of one or a plurality of deletions, insertions or substitutions. Polypeptide-encoding DNA sequences encompass sequences that comprise one or more additions, deletions, or substitutions of nucleotides when compared to a native or reference DNA sequence, but that encode a variant protein or fragment thereof that retains the relevant biological activity relative to the reference protein, e.g., can bind NPM1 at least 50% as well as the reference polypeptide of SEQ ID NO: 1. As to amino acid sequences, one of skill will recognize that individual substitutions, deletions or additions to a nucleic acid, peptide, polypeptide, or protein sequence which alters a single amino acid or a small percentage, (i.e. 5% or fewer, e.g., 4% or fewer, or 3% or fewer, or 1% or fewer) of amino acids in the encoded sequence is a "conservatively modified variant" where the alteration results in the substitution of an amino acid with a chemically similar amino acid. It is contemplated that some changes can potentially improve the relevant activity, such that a variant, whether conservative or not, has more than 100% of the activity of the reference polypeptide of SEQ ID NO: 1, e.g., 110%, 125%, 150%, 175%, 200%, 500%, 1000% or more.

The variant amino acid or DNA sequence can be at least 90%, at least 95%, at least 96%, at least 97%, at least 98%, at least 99%, or more, identical to a sequence provided herein or a nucleic acid encoding one of those amino acid sequences. The degree of homology (percent identity) between a native and a mutant sequence can be determined, for example, by comparing the two sequences using freely available computer programs commonly employed for this purpose on the world wide web. The variant amino acid or DNA sequence can be at least 90%, at least 91%, at least 92%, at least 93%, at least 94%, at least 95%, at least 96%, at least 97%, at least 98%, at least 99%, or more, similar to the sequence from which it is derived (referred to herein as an "original" sequence). The degree of similarity (percent similarity) between an original and a mutant sequence can be determined, for example, by using a similarity matrix. Similarity matrices are well known in the art and a number of tools for comparing two sequences using similarity matrices are freely available online, e.g., BLASTp or BLASTn (available on the world wide web at blast.ncbi.nlm.nih.gov), with default parameters set.

In the various embodiments described herein, it is further contemplated that variants (naturally occurring or otherwise), alleles, homologs, conservatively modified variants, and/or conservative substitution variants of any of the particular polypeptides described are encompassed. As to amino acid sequences, one of skill will recognize that individual substitutions, deletions or additions to a nucleic acid, peptide, polypeptide, or protein sequence which alters a single amino acid or a small percentage of amino acids in the encoded sequence is a "conservatively modified variant" where the alteration results in the substitution of an amino acid with a chemically similar amino acid and retains the desired activity of the polypeptide. Such conservatively modified variants are in addition to and do not exclude polymorphic variants, interspecies homologs, and alleles consistent with the disclosure.

A given amino acid can be replaced by a residue having similar physiochemical characteristics, e.g., substituting one aliphatic residue for another (such as Ile, Val, Leu, or Ala for one another), or substitution of one polar residue for another (such as between Lys and Arg; Glu and Asp; or Gln and Asn). Other such conservative substitutions, e.g., substitutions of entire regions having similar hydrophobicity characteristics, are well known. Polypeptides comprising conservative amino acid substitutions can be tested in any one of the assays described herein to confirm that a desired activity, e.g., NPM1-binding activity and specificity of a native or reference polypeptide is retained.

A given amino acid can be replaced by a residue having similar physiochemical characteristics, e.g., substituting one aliphatic residue for another (such as Ile, Val, Leu, or Ala for one another), or substitution of one polar residue for another (such as between Lys and Arg; Glu and Asp; or Gln and Asn). Other such conservative substitutions, e.g., substitutions of entire regions having similar hydrophobicity characteristics, are well known. Polypeptides comprising conservative amino acid substitutions can be tested in any one of the assays described herein to confirm that a desired activity of a native or reference polypeptide is retained. Conservative substitution tables providing functionally similar amino acids are well known in the art. Such conservatively modified variants are in addition to and do not exclude polymorphic variants, interspecies homologs, and alleles consistent with the disclosure.

Amino acids can be grouped according to similarities in the properties of their side chains (in A. L. Lehninger, in Biochemistry, second ed., pp. 73-75, Worth Publishers, New York (1975)): (1) non-polar: Ala (A), Val (V), Leu (L), Ile (I), Pro (P), Phe (F), Trp (W), Met (M); (2) uncharged polar: Gly (G), Ser (S), Thr (T), Cys (C), Tyr (Y), Asn (N), Gln (Q); (3) acidic: Asp (D), Glu (E); (4) basic: Lys (K), Arg (R), His (H). Alternatively, naturally occurring residues can be divided into groups based on common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: His, Lys, Arg; (5) residues that influence chain orientation: Gly, Pro; (6) aromatic: Trp, Tyr, Phe. Non-conservative substitutions will entail exchanging a member of one of these classes for another class. Particular conservative substitutions include, for example; Ala into Gly or into Ser; Arg into Lys; Asn into Gln or into His; Asp into Glu; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr; Tyr into Trp; and/or Phe into Val, into Ile or into Leu. Typically conservative substitutions for one another also include: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

In some embodiments, the polypeptide described herein (or a nucleic acid encoding such a polypeptide) can be a functional fragment of one of the amino acid sequences described herein. As used herein, a "functional fragment" is a fragment or segment of a polypeptide which retains at least 50% of the wildtype reference polypeptide's activity according to the assays described below herein. A functional fragment can comprise conservative substitutions of the sequences disclosed herein.

In some embodiments, the polypeptide described herein can be a variant of a sequence described herein. In some embodiments, the variant is a conservatively modified variant. Conservative substitution variants can be obtained by mutations of native nucleotide sequences, for example. A "variant," as referred to herein, is a polypeptide substantially homologous to a native or reference polypeptide, but which has an amino acid sequence different from that of the native or reference polypeptide because of one or a plurality of deletions, insertions or substitutions. Variant polypeptide-encoding DNA sequences encompass sequences that comprise one or more additions, deletions, or substitutions of nucleotides when compared to a native or reference DNA sequence, but that encode a variant protein or fragment thereof that retains activity. A wide variety of PCR-based site-specific mutagenesis approaches are known in the art and can be applied by the ordinarily skilled artisan.

In some embodiments, a polypeptide can comprise one or more amino acid substitutions or modifications. In some embodiments, the substitutions and/or modifications can, e.g., prevent or reduce proteolytic degradation in a subject. In some embodiments, a polypeptide can be modified by conjugating or fusing it to other polypeptide or polypeptide domains such as, by way of non-limiting example, transferrin (WO06096515A2), albumin (Yeh et al., 1992), growth hormone (US 2003104578AA); cellulose (Levy and Shoseyov, 2002); and/or Fc fragments (Ashkenazi and Chamow, 1997). The references in the foregoing paragraph are incorporated by reference herein in their entireties.

In some embodiments, a polypeptide as described herein can comprise at least one peptide bond replacement. A polypeptide as described herein can comprise one type of peptide bond replacement or multiple types of peptide bond replacements, e.g., 2 types, 3 types, 4 types, 5 types, or more types of peptide bond replacements. Non-limiting examples of peptide bond replacements include urea, thiourea, carbamate, sulfonyl urea, trifluoroethylamine, ortho-(aminoalkyl)-phenylacetic acid, para-(aminoalkyl)-phenylacetic acid, meta-(aminoalkyl)-phenylacetic acid, thioamide, tetrazole, boronic ester, olefinic group, and derivatives thereof.

In some embodiments, a polypeptide as described herein can comprise naturally occurring amino acids commonly found in polypeptides and/or proteins produced by living organisms, e.g., Ala (A), Val (V), Leu (L), Ile (I), Pro (P), Phe (F), Trp (IV), Met (M), Gly (G), Ser (S), Thr (T), Cys (C), Tyr (Y), Asn (N), Gln (Q), Asp (D), Glu (E), Lys (K), Arg (R), and His (H). In some embodiments, a polypeptide as described herein can comprise alternative amino acids. Non-limiting examples of alternative amino acids include, D-amino acids; beta-amino acids; homocysteine, phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine (3-mercapto-D-valine), ornithine, citruline, alpha-methyl-alanine, para-benzoylphenylalanine, para-amino phenylalanine, p-fluorophenylalanine, phenylglycine, propargylglycine, sarcosine, and tert-butylglycine), diaminobutyric acid, 7-hydroxy-tetrahydroisoquinoline carboxylic acid, naphthylalanine, biphenylalanine, cyclohexylalanine, amino-isobutyric acid, norvaline, norleucine, tert-leucine, tetrahydroisoquinoline carboxylic acid, pipecolic acid, phenylglycine, homophenylalanine, cyclohexylglycine, dehydroleucine, 2,2-diethylglycine, 1-amino-1-cyclopentanecarboxylic acid, 1-amino-1-cyclohexanecarboxylic acid, amino-benzoic acid, amino-naphthoic acid, gamma-aminobutyric acid, difluorophenylalanine, nipecotic acid, alpha-amino butyric acid, thienyl-alanine, t-butylglycine, trifluorovaline; hexafluoroleucine; fluorinated analogs; azide-modified amino acids; alkyne-modified amino acids; cyano-modified amino acids; and derivatives thereof.

In some embodiments, a polypeptide can be modified, e.g., by addition of a moiety to one or more of the amino acids that together comprise the polypeptide. In some embodiments, a polypeptide as described herein can comprise one or more moiety molecules, e.g., 1 or more moiety molecules per polypeptide, 2 or more moiety molecules per polypeptide, 5 or more moiety molecules per polypeptide, 10 or more moiety molecules per polypeptide or more moiety molecules per polypeptide. In some embodiments, a polypeptide as described herein can comprise one more types of modifications and/or moieties, e.g., 1 type of modification, 2 types of modifications, 3 types of modifications or more types of modifications. Non-limiting examples of modifications and/or moieties include PEGylation; glycosylation; HESylation; ELPylation; lipidation; acetylation; amidation; end-capping modifications; cyano groups; phosphorylation; albumin, and cyclization. In some embodiments, an end-capping modification can comprise acetylation at the N-terminus, N-terminal acylation, and N-terminal formylation. In some embodiments, an end-capping modification can comprise amidation at the C-terminus, introduction of C-terminal alcohol, aldehyde, ester, and thioester moieties. The half-life of a polypeptide can be increased by the addition of moieties, e.g., PEG, albumin, or other fusion partners (e.g., Fc fragment of an immunoglobin).

Any cysteine residue not involved in maintaining the proper conformation of the polypeptide also can be substituted, generally with serine, to improve the oxidative stability of the molecule and prevent aberrant crosslinking. Conversely, cysteine bond(s) can be added to the polypeptide to improve its stability or facilitate oligomerization.

Alterations of the native amino acid sequence can be accomplished by any of a number of techniques known to one of skill in the art. Mutations can be introduced, for example, at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion. Alternatively, oligonucleotide-directed site-specific mutagenesis procedures can be employed to provide an altered nucleotide sequence having particular codons altered according to the substitution, deletion, or insertion required. Techniques for making such alterations are very well established. Alterations of the original amino acid sequence can be accomplished by any of a number of techniques known to one of skill in the art. Mutations can be introduced, for example, at particular loci by synthesizing oligonucleotides containing a mutant sequence, flanked by restriction sites permitting ligation to fragments of the native sequence. Following ligation, the resulting reconstructed sequence encodes an analog having the desired amino acid insertion, substitution, or deletion. Alternatively, oligonucleotide-directed site-specific mutagenesis procedures can be employed to provide an altered nucleotide sequence having particular codons altered according to the substitution, deletion, or insertion required. Techniques for making such alterations include those disclosed by Khudyakov et al. "Artificial DNA: Methods and Applications" CRC Press, 2002; Braman "In Vitro Mutagenesis Protocols" Springer, 2004; and Rapley "The Nucleic Acid Protocols Handbook" Springer 2000; which are herein incorporated by reference in their entireties.

In some embodiments, a polypeptide as described herein can be chemically synthesized and mutations can be incorporated as part of the chemical synthesis process. Chemical synthesis of a polypeptide as described herein can be performed using any method known in the art. Such methods include but are not limited to solid phase peptide synthesis (SPSS), liquid phase synthesis, and microwave-assisted peptide synthesis. In SPSS, the type of resin used can determine the C-terminal moiety, e.g., the Wang resit can be used to synthesize polypeptides with C-terminal carboxylic acids, and RINK, Seiber Amide, or PAL resins can be used to synthesize polypeptides with C-terminal amides. Unnatural amino acids are readily incorporated during protein synthesis. Techniques for such synthesis include those disclosed by Benoiton "Chemistry of Peptide Synthesis" CRC Press 2016; Hussein "Peptide Synthesis: Methods and Protocols" Spring 2020; and Chase "Peptides: Synthesis and Applications" Callisto Reference 2018; which are herein incorporated by reference in their entireties.

Polypeptide binding affinity and/or relative polypeptide bonding affinity for human NPM can be determined by any method known in the art. Such methods include but are not limited to surface plasmon resonance (SPR), isothermal titration calorimetry, microscale thermophoresis, bio-layer interferometry (BLI), biofilm interference technology, and the like.

As used herein, the term "nucleic acid" or "nucleic acid sequence" refers to any molecule, preferably a polymeric molecule, incorporating units of ribonucleic acid, deoxyribonucleic acid or an analog thereof. The nucleic acid can be either single-stranded or double-stranded. A single-stranded nucleic acid can be one nucleic acid strand of a denatured double-stranded DNA. Alternatively, it can be a single-stranded nucleic acid not derived from any double-stranded DNA. In one aspect, the nucleic acid can be DNA. In another aspect, the nucleic acid can be RNA. Suitable DNA can include, e.g., genomic DNA or cDNA. Suitable RNA can include, e.g., mRNA.

The term "expression" refers to the cellular processes involved in producing RNA and proteins and as appropriate, secreting proteins, including where applicable, but not limited to, for example, transcription, transcript processing, translation and protein folding, modification and processing. Expression can refer to the transcription and stable accumulation of sense (mRNA) or antisense RNA derived from a nucleic acid fragment or fragments of the invention and/or to the translation of mRNA into a polypeptide.

"Expression products" include RNA transcribed from a gene, and polypeptides obtained by translation of mRNA transcribed from a gene. The term "gene" means the nucleic acid sequence which is transcribed (DNA) to RNA in vitro or in vivo when operably linked to appropriate regulatory sequences. The gene may or may not include regions preceding and following the coding region, e.g., 5' untranslated (5' UTR) or "leader" sequences and 3' UTR or "trailer" sequences, as well as intervening sequences (introns) between individual coding segments (exons).

"Operably linked" refers to an arrangement of elements wherein the components so described are configured so as to perform their usual function. Thus, control elements operably linked to a coding sequence are capable of effecting the expression of the coding sequence. The control elements need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

In some embodiments of any of the aspects, a polypeptide, nucleic acid, or cell as described herein can be engineered. As used herein, "engineered" refers to the aspect of having been manipulated by the hand of man. For example, a polypeptide is considered to be "engineered" when at least one aspect of the polypeptide, e.g., its sequence, has been manipulated by the hand of man to differ from the aspect as it exists in nature. As is common practice and is understood by those in the art, progeny of an engineered cell are typically still referred to as "engineered" even though the actual manipulation was performed on a prior entity.

In some embodiments of any of the aspects, the polypeptide described herein is exogenous to a subject. In some embodiments of any of the aspects, the polypeptide described herein is ectopic to a subject. In some embodiments of any of the aspects, the polypeptide described herein is not endogenous to a subject.

The term "exogenous" refers to a substance present in a cell other than its native source. The term "exogenous" when used herein can refer to a nucleic acid (e.g., a nucleic acid encoding a polypeptide) or a polypeptide that has been introduced by a process involving the hand of man into a biological system such as a cell or organism in which it is not normally found and one wishes to introduce the nucleic acid or polypeptide into such a cell or organism. Alternatively, "exogenous" can refer to a nucleic acid or a polypeptide that has been introduced by a process involving the hand of man into a biological system such as a cell or organism in which it is found in relatively low amounts and one wishes to increase the amount of the nucleic acid or polypeptide in the cell or organism, e.g., to create ectopic expression or levels. In contrast, the term "endogenous" refers to a substance that is native to the biological system or cell. As used herein, "ectopic" refers to a substance that is found in an unusual location and/or amount. An ectopic substance can be one that is normally found in a given cell, but at a much lower amount and/or at a different time. Ectopic also includes substance, such as a polypeptide or nucleic acid that is not naturally found or expressed in a given cell in its natural environment.

In some embodiments, a nucleic acid encoding a polypeptide as described herein is comprised by a vector. In some of the aspects described herein, a nucleic acid sequence encoding a given polypeptide as described herein, or any module thereof, is operably linked to a vector. The term "vector", as used herein, refers to a nucleic acid construct designed for delivery to a host cell or for transfer between different host cells. As used herein, a vector can be viral or non-viral. The term "vector" encompasses any genetic element that is capable of replication when associated with the proper control elements and that can transfer gene sequences to cells. A vector can include, but is not limited to, a cloning vector, an expression vector, a plasmid, phage, transposon, cosmid, chromosome, virus, virion, etc.

In some embodiments of any of the aspects, the vector is recombinant, e.g., it comprises sequences originating from at least two different sources. In some embodiments of any of the aspects, the vector comprises sequences originating from at least two different species. In some embodiments of any of the aspects, the vector comprises sequences originating from at least two different genes, e.g., it comprises a fusion protein or a nucleic acid encoding an expression product which is operably linked to at least one non-native (e.g., heterologous) genetic control element (e.g., a promoter, suppressor, activator, enhancer, response element, or the like).

In some embodiments of any of the aspects, the vector or nucleic acid described herein is codon-optomized, e.g., the native or wild-type sequence of the nucleic acid sequence has been altered or engineered to include alternative codons such that altered or engineered nucleic acid encodes the same polypeptide expression product as the native/wild-type sequence, but will be transcribed and/or translated at an improved efficiency in a desired expression system. In some embodiments of any of the aspects, the expression system is an organism other than the source of the native/wild-type sequence (or a cell obtained from such organism). In some embodiments of any of the aspects, the vector and/or nucleic acid sequence described herein is codon-optimized for expression in a mammal or mammalian cell, e.g., a mouse, a murine cell, or a human cell. In some embodiments of any of the aspects, the vector and/or nucleic acid sequence described herein is codon-optimized for expression in a human cell. In some embodiments of any of the aspects, the vector and/or nucleic acid sequence described herein is codon-optimized for expression in a yeast or yeast cell. In some embodiments of any of the aspects, the vector and/or nucleic acid sequence described herein is codon-optimized for expression in a bacterial cell. In some embodiments of any of the aspects, the vector and/or nucleic acid sequence described herein is codon-optimized for expression in an *E. coli* cell.

As used herein, the term "expression vector" refers to a vector that directs expression of an RNA or polypeptide from sequences linked to transcriptional regulatory sequences on the vector. The sequences expressed will often, but not necessarily, be heterologous to the cell. An expression vector may comprise additional elements, for example, the expression vector may have two replication systems, thus allowing it to be maintained in two organisms, for example in human cells for expression and in a prokaryotic host for cloning and amplification.

As used herein, the term "viral vector" refers to a nucleic acid vector construct that includes at least one element of viral origin and has the capacity to be packaged into a viral vector particle. The viral vector can contain the nucleic acid encoding a polypeptide as described herein in place of non-essential viral genes. The vector and/or particle may be utilized for the purpose of transferring any nucleic acids into cells either in vitro or in vivo. Numerous forms of viral vectors are known in the art.

By "recombinant vector" is meant a vector that includes a heterologous nucleic acid sequence, or "transgene" that is capable of expression in vivo. It should be understood that the vectors described herein can, in some embodiments, be combined with other suitable compositions and therapies. In some embodiments, the vector is episomal. The use of a suitable episomal vector provides a means of maintaining the nucleotide of interest in the subject in high copy number extra chromosomal DNA thereby eliminating potential effects of chromosomal integration.

It should be understood that the vectors described herein can, in some embodiments, be combined with other suitable compositions and therapies. In some embodiments, the vector is episomal. The use of a suitable episomal vector provides a means of maintaining the nucleotide of interest in the subject in high copy number extra chromosomal DNA thereby eliminating potential effects of chromosomal integration.

As used herein, the terms "treat," "treatment," "treating," or "amelioration" refer to therapeutic treatments, wherein the object is to reverse, alleviate, ameliorate, inhibit, slow down or stop the progression or severity of a condition associated with a disease or disorder, e.g., acute kidney injury and/or ischemia. The term "treating" includes reducing or alleviating at least one adverse effect or symptom of a condition, disease or disorder associated with, e.g., an acute kidney injury and/or ischemia. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality, whether detectable or undetectable. The term "treatment" of a disease also includes providing relief from the symptoms or side-effects of the disease (including palliative treatment).

In some embodiments of any of the aspect, treatment comprises a reduction in the rate at which serum creatinine is rising over time. In some embodiments of any of the aspect, treatment comprises a reduction in the rate at which serum creatinine is rising over 48 hours. In some embodiments of any of the aspect, treatment comprises a reduction in the rate at which serum creatinine is rising over 7 days.

In some embodiments of any of the aspect, treatment comprises a stabilization of the rate at which serum creatinine is rising over time. In some embodiments of any of the aspect, treatment comprises a stabilization of the rate at which serum creatinine is rising over 48 hours. In some embodiments of any of the aspect, treatment comprises a stabilization of the rate at which serum creatinine is rising over 7 days.

In some embodiments of any of the aspect, treatment comprises a reduction in serum creatinine over time. In some embodiments of any of the aspect, treatment comprises a reduction in serum creatinine is over 48 hours. In some embodiments of any of the aspect, treatment comprises a reduction in the serum creatinine over 7 days.

In some embodiments of any of the aspect, treatment comprises preventing an increase in serum creatinine over time. In some embodiments of any of the aspect, treatment comprises preventing an increase in serum creatinine over 48 hours. In some embodiments of any of the aspect, treatment comprises preventing an increase in serum creatinine over 7 days.

In some embodiments of any of the aspect, treatment comprises preventing an increase in BUN above 100 mg/dL. In some embodiments of any of the aspect, treatment comprises preventing an increase in BUN above 90 mg/dL. In some embodiments of any of the aspect, treatment comprises preventing an increase in BUN above 80 mg/dL. In some embodiments of any of the aspect, treatment comprises preventing an increase in BUN above 70 mg/dL. In some embodiments of any of the aspect, treatment comprises preventing an increase in BUN above 60 mg/dL.

In some embodiments of any of the aspect, treatment comprises reducing BUN below 100 mg/dL. In some embodiments of any of the aspect, treatment comprises reducing BUN below 90 mg/dL. In some embodiments of any of the aspect, treatment comprises reducing BUN below 80 mg/dL. In some embodiments of any of the aspect, treatment comprises reducing BUN below 70 mg/dL. In some embodiments of any of the aspect, treatment comprises reducing BUN below 60 mg/dL.

In some embodiments of any of the aspect, treatment comprises reducing BUN below 100 mg/dL within 48 hours. In some embodiments of any of the aspect, treatment comprises reducing BUN below 90 mg/dL within 48 hours. In some embodiments of any of the aspect, treatment comprises reducing BUN below 80 mg/dL within 48 hours. In some embodiments of any of the aspect, treatment comprises reducing BUN below 70 mg/dL within 48 hours. In some embodiments of any of the aspect, treatment comprises reducing BUN below 60 mg/dL within 48 hours.

In some embodiments of any of the aspects, described herein is a prophylactic method of treatment. As used herein "prophylactic" refers to the timing and intent of a treatment relative to a disease or symptom, that is, the treatment is administered prior to clinical detection or diagnosis of that particular disease or symptom in order to protect the patient from the disease or symptom. Prophylactic treatment can encompass a reduction in the severity or speed of onset of the disease or symptom, or contribute to faster recovery from the disease or symptom. Accordingly, the methods described herein can be prophylactic relative to a need for dialysis. In some embodiments of any of the aspects, prophylactic treatment is not prevention of all symptoms or signs of a disease.

As used herein, the term "pharmaceutical composition" refers to the active agent in combination with a pharmaceutically acceptable carrier e.g., a carrier commonly used in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. In some embodiments of any of the aspects, a pharmaceutically acceptable carrier can be a carrier other than water. In some embodiments of any of the aspects, a pharmaceutically acceptable carrier can be a cream, emulsion, gel, liposome, nanoparticle, and/or ointment. In some embodiments of any of the aspects, a pharmaceutically acceptable carrier can be an artificial or engineered carrier, e.g., a carrier that the active ingredient would not be found to occur in in nature.

As used herein, the term "nanoparticle" refers to particles that are on the order of about 1 to 1,000 nanometers in diameter or width. The term "nanoparticle" includes nanospheres; nanorods; nanoshells; and nanoprisms; these nanoparticles may be part of a nanonetwork. The term "nanoparticles" also encompasses liposomes and lipid particles having the size of a nanoparticle. Exemplary nanoparticles include lipid nanoparticles or ferritin nanoparticles. Lipid nanoparticles can comprise multiple componenents, including, e.g., ionizable lipids (such as MC3, DLin-MC3-DMA, ALC-0315, or SM-102), pegylated lipids (such as PEG2000-C-DMG, PEG2000-DMG, ALC-0159), phospholipids (such as DSPC), and cholesterol.

Exemplary liposomes can comprise, e.g., DSPC, DPPC, DSPG, Cholesterol, hydrogenated soy phosphatidylcholine, soy phosphatidyl choline, methoxypolyethylene glycol (mPEG-DSPE) phosphatidyl choline (PC), phosphatidyl glycerol (PG), distearoylphosphatidylcholine, and combinations thereof.

As used herein, the term "administering," refers to the placement of a compound as disclosed herein into a subject by a method or route which results in at least partial delivery of the agent at a desired site. Pharmaceutical compositions comprising the compounds disclosed herein can be administered by any appropriate route which results in an effective treatment in the subject. In some embodiments, administration comprises physical human activity, e.g., an injection, act of ingestion, an act of application, and/or manipulation of a delivery device or machine. Such activity can be performed, e.g., by a medical professional and/or the subject being treated.

As used herein, "contacting" refers to any suitable means for delivering, or exposing, an agent to at least one cell. Exemplary delivery methods include, but are not limited to, direct delivery to cell culture medium, perfusion, injection, or other delivery method well known to one skilled in the art. In some embodiments, contacting comprises physical human activity, e.g., an injection; an act of dispensing, mixing, and/or decanting; and/or manipulation of a delivery device or machine.

The term "statistically significant" or "significantly" refers to statistical significance and generally means a two standard deviation (2SD) or greater difference.

Other than in the operating examples, or where otherwise indicated, all numbers expressing quantities of ingredients or reaction conditions used herein should be understood as modified in all instances by the term "about." The term "about" when used in connection with percentages can mean ±1%.

As used herein, the term "comprising" means that other elements can also be present in addition to the defined elements presented. The use of "comprising" indicates inclusion rather than limitation.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of additional elements that do not materially affect the basic and novel or functional characteristic(s) of that embodiment of the invention.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example".

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims. Definitions of common terms in immunology and molecular biology can be found in The Merck Manual of Diagnosis and Therapy, 20th Edition, published by Merck Sharp & Dohme Corp., 2018 (ISBN 0911910190, 978-0911910421); Robert S. Porter et al. (eds.), The Encyclopedia of Molecular Cell Biology and Molecular Medicine, published by Blackwell Science Ltd., 1999-2012 (ISBN 9783527600908); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006; Janeway's Immunobiology, Kenneth Murphy, Allan Mowat, Casey Weaver (eds.), W. W. Norton & Company, 2016 (ISBN 0815345054, 978-0815345053); Lewin's Genes XI, published by Jones & Bartlett Publishers, 2014 (ISBN-1449659055); Michael Richard Green and Joseph Sambrook, Molecular Cloning: A Laboratory Manual, 4th ed., Cold Spring Harbor Laboratory Press, Cold Spring Harbor, N.Y., USA (2012) (ISBN 1936113414); Davis et al., Basic Methods in Molecular Biology, Elsevier Science Publishing, Inc., New York, USA (2012) (ISBN 044460149X); Laboratory Methods in Enzymology: DNA, Jon Lorsch (ed.) Elsevier, 2013 (ISBN 0124199542); Current Protocols in Molecular Biology (CPMB), Frederick M. Ausubel (ed.), John Wiley and Sons, 2014 (ISBN 047150338X, 9780471503385), Current Protocols in Protein Science (CPPS), John E. Coligan (ed.), John Wiley and Sons, Inc., 2005; and Current Protocols in Immunology (CPI) (John E. Coligan, ADA M Kruisbeek, David H Margulies, Ethan M Shevach, Warren Strobe, (eds.) John Wiley and Sons, Inc., 2003 (ISBN 0471142735, 9780471142737), the contents of which are all incorporated by reference herein in their entireties.

Other terms are defined herein within the description of the various aspects of the invention.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

In some embodiments, the present technology may be defined in any of the following numbered paragraphs:

1. A polypeptide comprising at least one nucleophosmin-binding domain, each nucleophosmin domain comprising the sequence of SEQ ID NO: 6 or 8.
2. The polypeptide of paragraph 1, not comprising the sequence of SEQ ID NO: 1.
3. The polypeptide of any one of the preceding paragraphs, comprising the sequence of SEQ ID NO: 2, 3, 4, 5, 7, 9, 11, 12, 13, or 14.
4. The polypeptide of any one of the preceding paragraphs, wherein an X comprised by one of SEQ ID Nos: 2-9 is a non-natural amino acid.
5. The polypeptide of any one of the preceding paragraphs, wherein an X comprised by one of SEQ ID Nos: 2-9 is a natural amino acid.
6. The polypeptide of any one of the preceding paragraphs, wherein an X comprised by one of SEQ ID Nos: 2-9 is alanine.
7. The polypeptide of any one of the preceding paragraphs, further comprising at least one N-terminus modification and/or at least one C-terminus modification.
8. The polypeptide of paragraph 7, wherein the at least one N-terminus modification and/or at least one C-terminus modification is selected from acetylation, methyl esterification, amidation, carboxylation, N-ethylamidation, or addition of pyroglutamate.
9. The polypeptide of any one of the preceding paragraphs, comprising at least one C-terminus modification.
10. The polypeptide of any one of the preceding paragraphs, wherein the at least one C-terminus modification is amidation or methyl esterification.
11. The polypeptide of any one of the preceding paragraphs, wherein the at least one C-terminus modification is amidation.
12. The polypeptide of any one of the preceding paragraphs, wherein the at least one C-terminus modification is methyl esterification.
13. The polypeptide of any one of the preceding paragraphs, wherein the polypeptide further comprises an N-terminal or C-terminal cell penetration motif.
14. The polypeptide of any one of the preceding paragraphs, wherein the polypeptide further comprises an N-terminal cell penetration motif.
15. The polypeptide of any one of the preceding paragraphs, wherein the cell penetration motif is a kidney cell penetration motif.
16. The polypeptide of any one of the preceding paragraphs, wherein the cell penetration motif comprises PKKKRKV (SEQ ID NO: 10) or RREEERREEERREEEK (SEQ ID NO: 17).
17. The polypeptide of any one of the preceding paragraphs, wherein the N-terminal or C-terminal cell penetration motif and the at least one nucleophosmin-binding domain are separated by a linker.
18. The polypeptide of paragraph 17, wherein the linker is an alanine residue.
19. A method of treating acute kidney injury in a subject in need thereof, the method comprising administering the polypeptide of any one of the preceding paragraphs to the subject.
20. A method of treating ischemia in subject in need thereof, the method comprising administering the polypeptide of any one of the preceding paragraphs to the subject.
21. The method of paragraph 20, wherein the subject is a post-operative cardiac surgery patient.

In some embodiments, the present technology may be defined in any of the following numbered paragraphs:

1. A polypeptide comprising at least one nucleophosmin-binding domain, each nucleophosmin-binding domain comprising the sequence of SEQ ID NO: 6 or 8.
2. The polypeptide of paragraph 1, not comprising the sequence of SEQ ID NO: 1.
3. The polypeptide of any one of the preceding paragraphs, comprising the sequence of SEQ ID NO: 2, 3, 4, 5, 7, 9, 11, 12, 13, or 14.
4. The polypeptide of any one of the preceding paragraphs, wherein an X comprised by one of SEQ ID Nos: 2-9 is a non-natural amino acid.
5. The polypeptide of any one of the preceding paragraphs, wherein an X comprised by one of SEQ ID Nos: 2-9 is a natural amino acid.
6. The polypeptide of any one of the preceding paragraphs, wherein an X comprised by one of SEQ ID Nos: 2-9 is alanine.
7. The polypeptide of any one of the preceding paragraphs, further comprising at least one N-terminus modification and/or at least one C-terminus modification.
8. The polypeptide of paragraph 7, wherein the at least one N-terminus modification and/or at least one C-terminus modification is selected from acetylation, methyl esterification, amidation, carboxylation, N-ethylamidation, or addition of pyroglutamate.
9. The polypeptide of any one of the preceding paragraphs, comprising at least one C-terminus modification.
10. The polypeptide of any one of the preceding paragraphs, wherein the at least one C-terminus modification is amidation or methyl esterification.
11. The polypeptide of any one of the preceding paragraphs, wherein the at least one C-terminus modification is amidation.
12. The polypeptide of any one of the preceding paragraphs, wherein the at least one C-terminus modification is methyl esterification.
13. The polypeptide of any one of the preceding paragraphs, wherein the polypeptide further comprises an N-terminal or C-terminal cell penetration motif.
14. The polypeptide of any one of the preceding paragraphs, wherein the polypeptide further comprises an N-terminal cell penetration motif.
15. The polypeptide of any one of the preceding paragraphs, wherein the cell penetration motif is a kidney cell penetration motif.
16. The polypeptide of any one of the preceding paragraphs, wherein the cell penetration motif comprises PKKKRKV (SEQ ID NO: 10) or RREEERREEERREEEK (SEQ ID NO: 17).

17. The polypeptide of any one of the preceding paragraphs, wherein the N-terminal or C-terminal cell penetration motif and the at least one nucleophosmin-binding domain are separated by a linker.
18. The polypeptide of paragraph 17, wherein the linker is an alanine residue.
19. A method of treating or preventing acute kidney injury in a subject in need thereof, the method comprising administering the polypeptide of any one of the preceding paragraphs to the subject.
20. A method of treating ischemia in subject in need thereof, the method comprising administering the polypeptide of any one of the preceding paragraphs to the subject.
21. The method of paragraph 20, wherein the subject is a post-operative cardiac surgery patient.
22. The method of any one of paragraphs 19-21, wherein the treatment is prophylactic.
23. The method of any one of paragraphs 19-22, wherein the administration occurs before cardiac surgery.

In some embodiments, the present technology may be defined in any of the following numbered paragraphs:

1. A polypeptide comprising at least one nucleophosmin-binding domain, each nucleophosmin-binding domain comprising the sequence of SEQ ID NO: 6, 8, or 65.
2. The polypeptide of paragraph 1, not comprising the sequence of SEQ ID NO: 1.
3. The polypeptide of any one of the preceding paragraphs, comprising the sequence of SEQ ID NO: 2, 3, 4, 5, 7, 9, 11, 12, 13, 14, 54, 55, 56, 57, 58, 59, 60, 61, 62, 63, or 64.
4. The polypeptide of any one of the preceding paragraphs, wherein an X comprised by one of SEQ ID Nos: 2-9, 54, 55, or 65 is a non-natural amino acid.
5. The polypeptide of any one of the preceding paragraphs, wherein an X comprised by one of SEQ ID Nos: 2-9, 54, 55, or 65 is a natural amino acid.
6. The polypeptide of any one of the preceding paragraphs, wherein an X comprised by one of SEQ ID Nos: 2-9, 54, 55, or 65 is alanine.
7. The polypeptide of any one of the preceding paragraphs, further comprising at least one N-terminus modification and/or at least one C-terminus modification.
8. The polypeptide of paragraph 7, wherein the at least one N-terminus modification and/or at least one C-terminus modification is selected from acetylation, methyl esterification, amidation, carboxylation, N-ethylamidation, or addition of pyroglutamate.
9. The polypeptide of any one of the preceding paragraphs, comprising at least one C-terminus modification.
10. The polypeptide of any one of the preceding paragraphs, wherein the at least one C-terminus modification is amidation or methyl esterification.
11. The polypeptide of any one of the preceding paragraphs, wherein the at least one C-terminus modification is amidation.
12. The polypeptide of any one of the preceding paragraphs, wherein the at least one C-terminus modification is methyl esterification.
13. The polypeptide of any one of the preceding paragraphs, wherein the polypeptide further comprises an N-terminal or C-terminal cell penetration motif.
14. The polypeptide of any one of the preceding paragraphs, wherein the polypeptide further comprises an N-terminal cell penetration motif.
15. The polypeptide of any one of the preceding paragraphs, wherein the cell penetration motif is a kidney cell penetration motif.
16. The polypeptide of any one of the preceding paragraphs, wherein the cell penetration motif comprises PKKKRKV (SEQ ID NO: 10), RREEERREEER-REEEK (SEQ ID NO: 17), KKRRRKKRRRKKRRRK (SEQ ID NO: 53).
17. The polypeptide of any one of the preceding paragraphs, wherein the N-terminal or C-terminal cell penetration motif and the at least one nucleophosmin-binding domain are separated by a linker.
18. The polypeptide of paragraph 17, wherein the linker is an alanine residue.
19. The polypeptide of paragraph 17, wherein the linker is a beta-alanine residue.
20. The polypeptide of any one of the preceding paragraphs, wherein the polypeptide comprises the sequence of one of SEQ ID NOs: 18-50 and 66-141.
21. The polypeptide of any one of the preceding paragraphs, wherein the polypeptide comprises the sequence of one of SEQ ID NOs: 75, 76, 123, 124, 126, 128, 134, 138, and 139.
22. The polypeptide of any one of the preceding paragraphs, wherein the polypeptide comprises the sequence of one of SEQ ID NOs: 123, 138, and 139.
23. A method of treating or preventing acute kidney injury in a subject in need thereof, the method comprising administering the polypeptide of any one of the preceding paragraphs to the subject.
24. A method of treating ischemia in a subject in need thereof, the method comprising administering the polypeptide of any one of the preceding paragraphs to the subject.
25. The method of paragraph 24, wherein the subject is a post-operative cardiac surgery patient.
26. The method of any one of paragraphs 24-25, wherein the treatment is prophylactic.
27. The method of any one of paragraphs 24-26, wherein the administration occurs before cardiac surgery.
28. A polypeptide of any one of paragraphs 1-23, for use in a method of treating or preventing acute kidney injury in a subject.
29. A polypeptide of any one of paragraphs 1-23, for use in a method of treating ischemia in a subject.
30. The polypeptide of paragraph 29, wherein the subject is a post-operative cardiac surgery patient.
31. The polypeptide of any one of paragraphs 28-30, wherein the treatment is prophylactic.
32. The polypeptide of any one of paragraphs 28-31, wherein the administration occurs before cardiac surgery.

The technology described herein is further illustrated by the following examples which in no way should be construed as being further limiting.

EXAMPLES

Example 1

The disclosed polypeptides of the invention comprise non-natural modifications of a linear 21 amino acid polypeptide TVTIFVAGVLTASLTIWKKMG (SEQ ID NO: 1) derived from BCL-2 Associated X Protein (BAX). Our team previously discovered that compound NPMB1, which consists of the 21 amino acid residue polypeptide linked to a kidney cell penetrating sequence Ac-PKKKRKV-βA (SEQ ID NO: 15) binds to human nucleophosmin (NPM1) and effectively inhibits regulated cell death triggered by ischemia in acute kidney injury models (FIG. 1). During ischemic stress, monomeric NPM1 binds to conformationally active BAX and shuttles it to the outer mitochondrial membrane, triggering the cell death cascade, tissue injury, and AKI. NPMB1 prevents this lethal protein-protein interaction and therefore ameliorates regulated cell death of kidney cells during and after ischemia. By using the BAX polypeptide sequence known to bind to NPM1, NPMB1 is specific to the targeted protein:protein interaction and thereby decreases the likelihood of adverse effects from non-specific binding to other cellular proteins and organelles. NPMB1 inhibits kidney cell death in both a cell-based assay and in an in vivo mouse model of ischemic AKI, see e.g., *J Am Soc Nephrol* 30: 50-62, 2019; which is incorporated by reference herein in its entirety.

Figure 2:
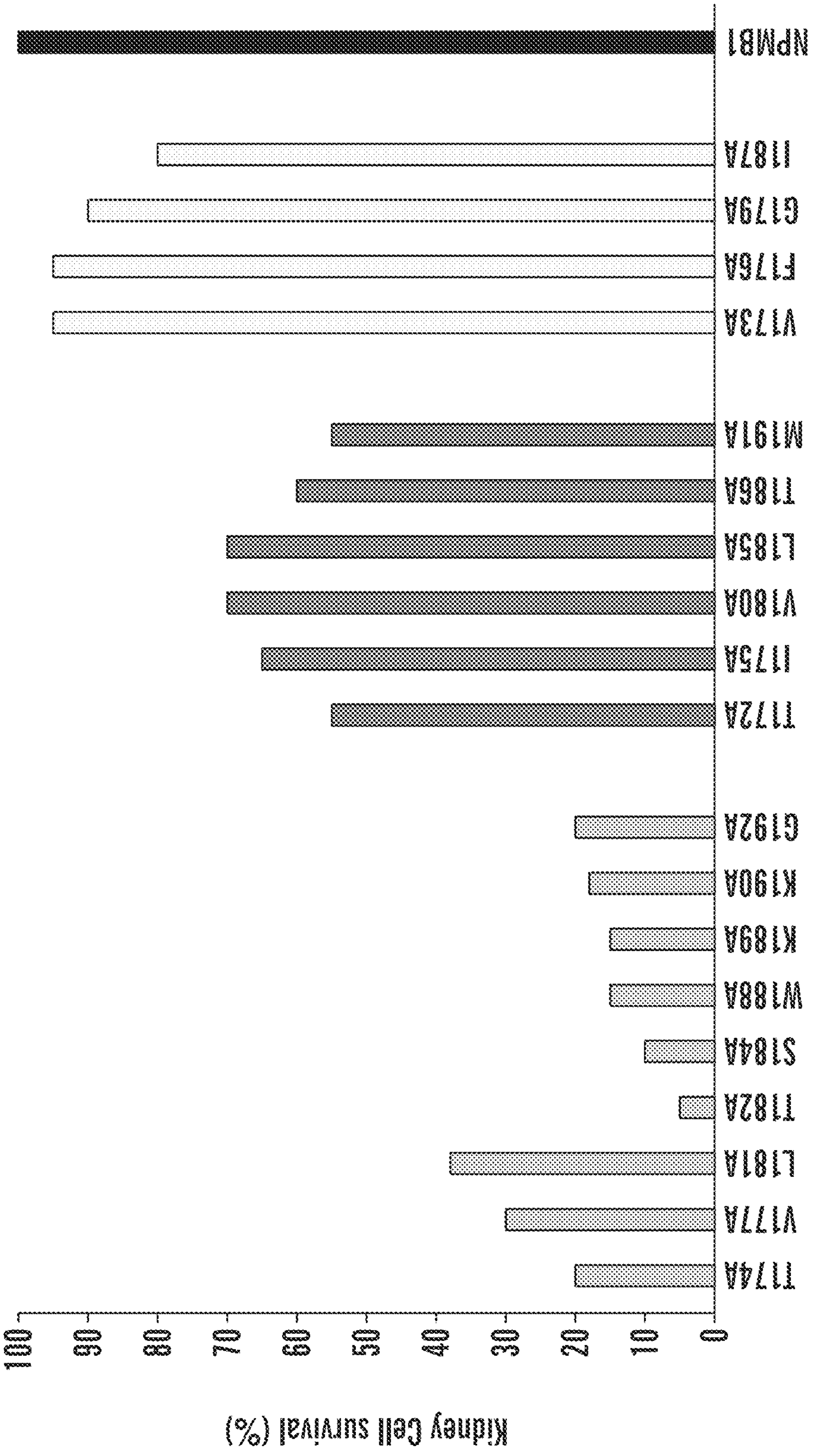
FIG. 2 depicts an NPMB1 Alanine Scan. Relative kidney cell survival rate after 70 min ischemic stress in vitro induced by metabolic inhibitors in the presence of NPMB1 (control) vs. 19 different NPMBx polypeptides with single alanine substitutions (2 additional NPMB1 alanine residues were not substituted). Residue numbers (x axis) reflect Bax sequence that binds human NPM1; Survival data are normalized to NPMB1; post-ischemic kidney cell survival is shown in tertiles: (left-most group: 5-40% survival; middle-group: 55-70% and third group: 80-95%); n=3 separate experiments.
Figure 3:
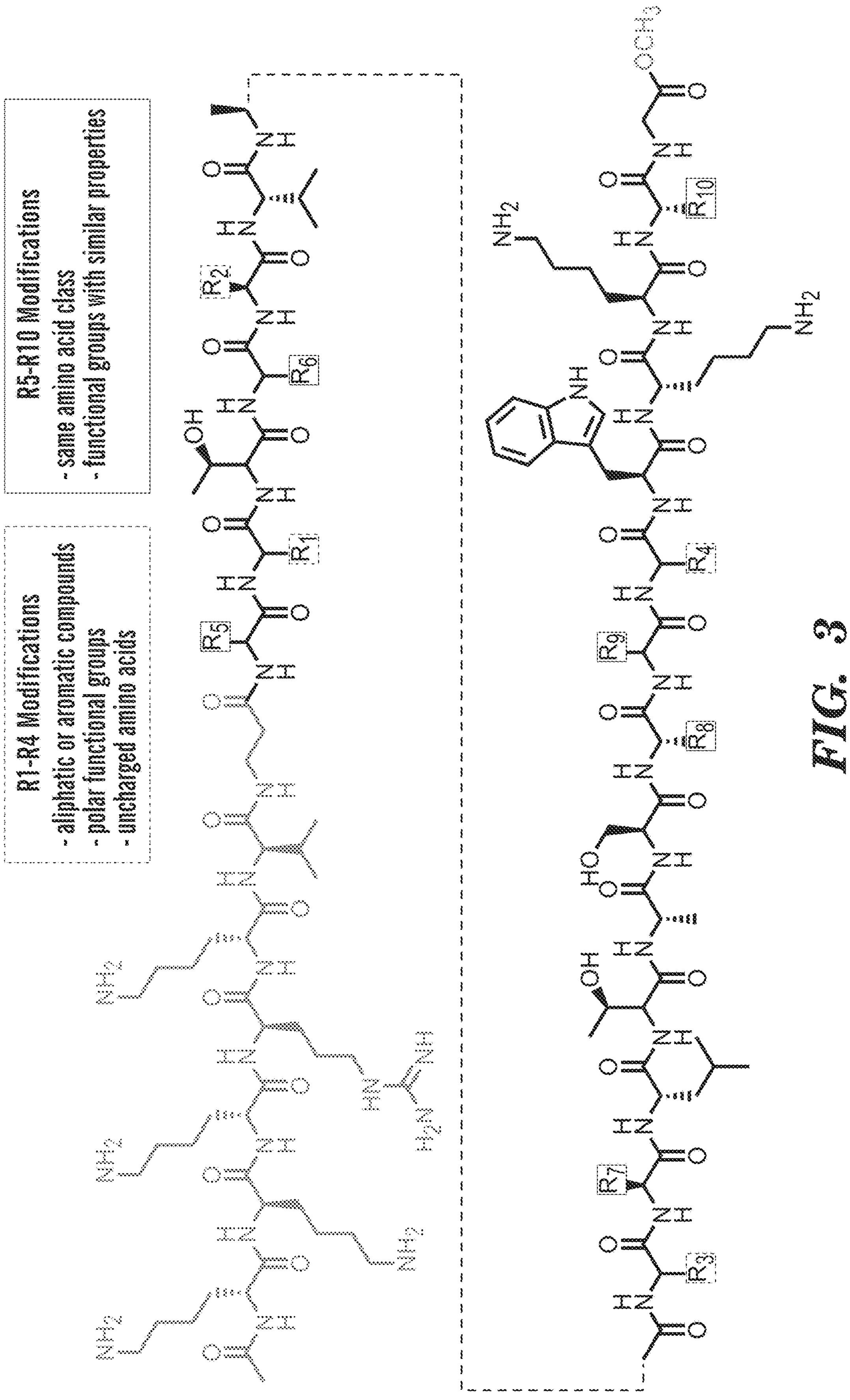
FIG. 3 depicts a strategic polypeptide modification improves drug efficacy. Modifications of 4 amino acids in distinct functional groups (marked R1-R4) or changes to 6 amino acids (marked R5-R10) that localize to functional groups with similar properties activity, stability, and efficacy of the polypeptide inhibitor (see Example 1). Figure discloses SEQ ID NO: 52.
Figure 4:
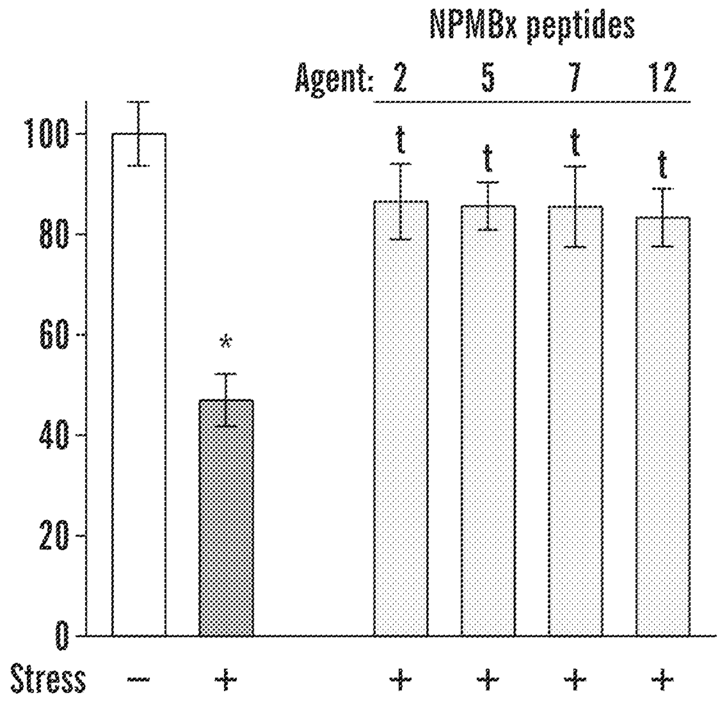
FIG. 4 demonstrates that novel NPMBx polypeptides protect primary kidney proximal tubule cells from ischemic stress. Relative kidney cell survival rate after 70 min ischemic stress in vitro induced by transient exposure to metabolic inhibitors in the presence of NPMB polypeptides (Agents 2, 5, 7, 14 that reflect alanine scan polypeptides A173, A187, A179, A176) vs. a non-specific polypeptide (GFP fragment). Survival data normalized to baseline (no stress); *P<0.01 vs. baseline; t P<0.05 vs. stress; data represent 3 separate experiments; error bars represent mean+SD.
Figure 5A:
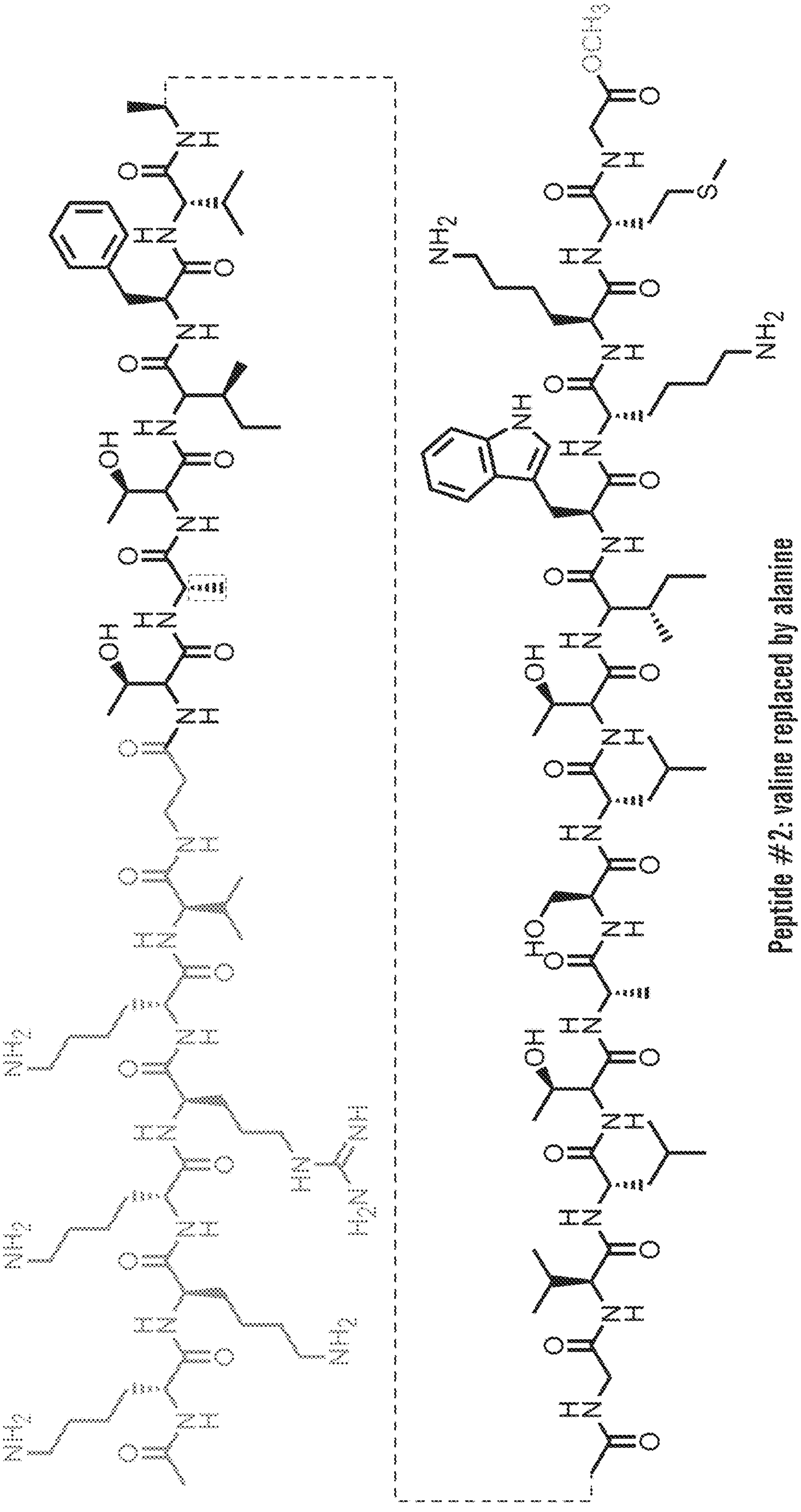
FIGS. 5A-5B demonstrate that four polypeptides with distinct modifications were synthesized that substantially improve the viability of primary murine kidney cells after ischemic stress induced by metabolic inhibitors. Agents 2 and 5 are shown in FIG. 5A, agents 7 and 12 are shown in FIG. 5B. Figure discloses SEQ ID NOS 21, 24, 26, and 31, respectively, in order of appearance.
Figure 5A:
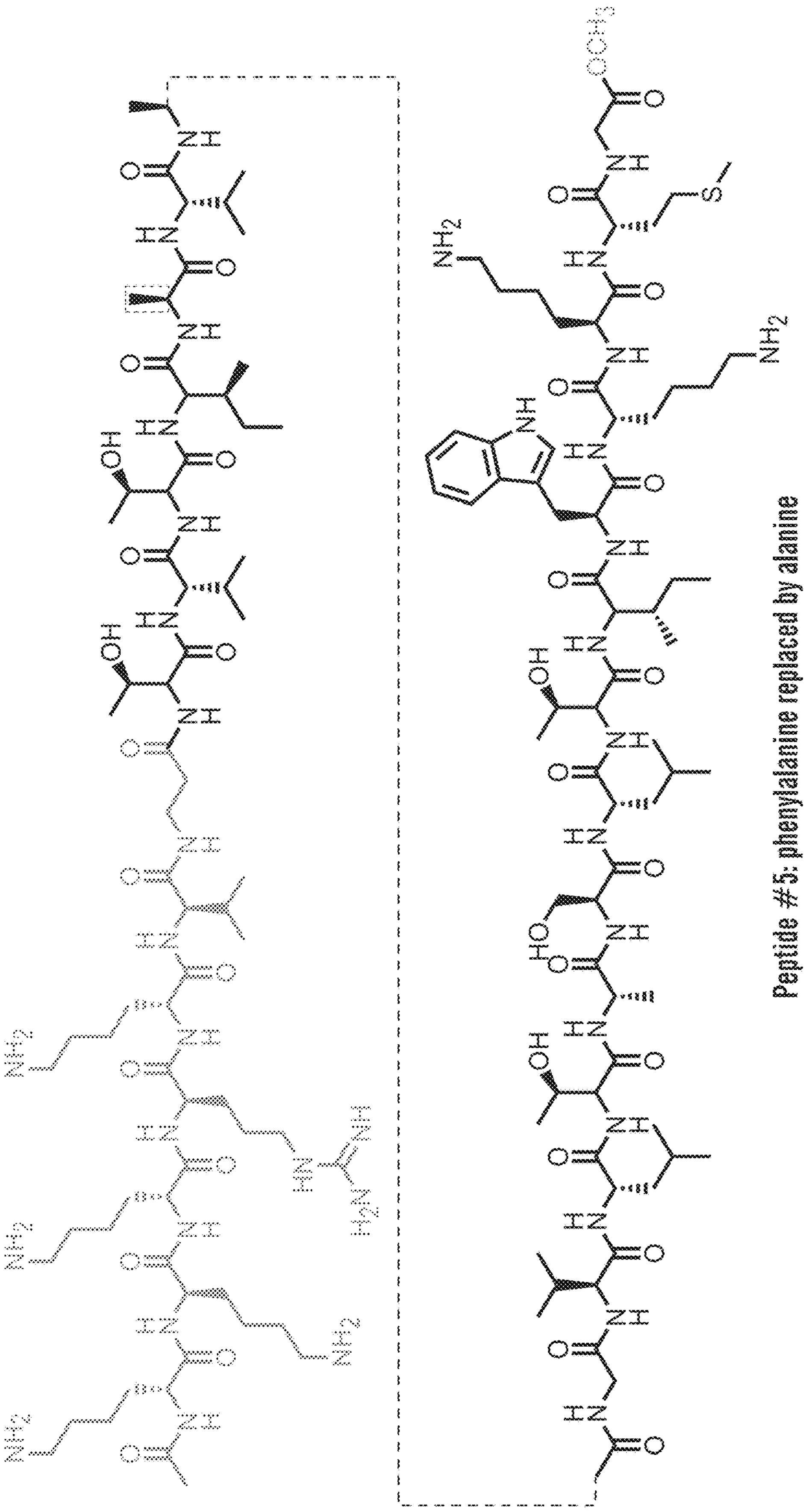
Figure 5A:
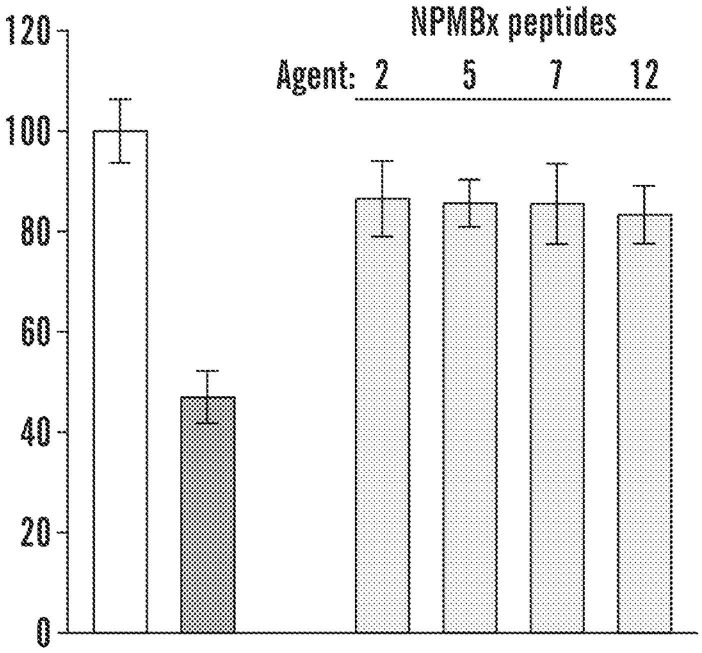
Figure 5B:
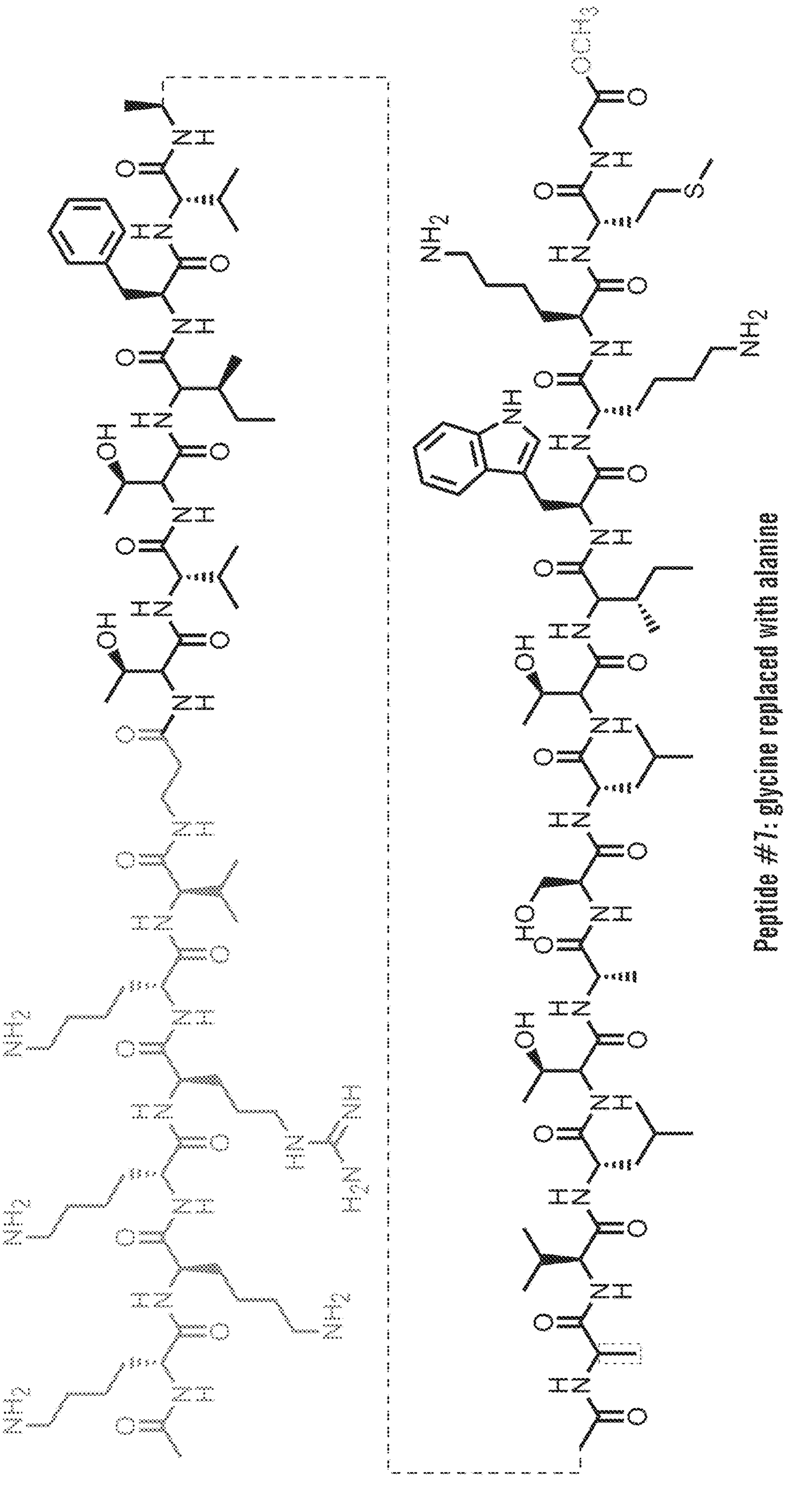
Figure 5B:
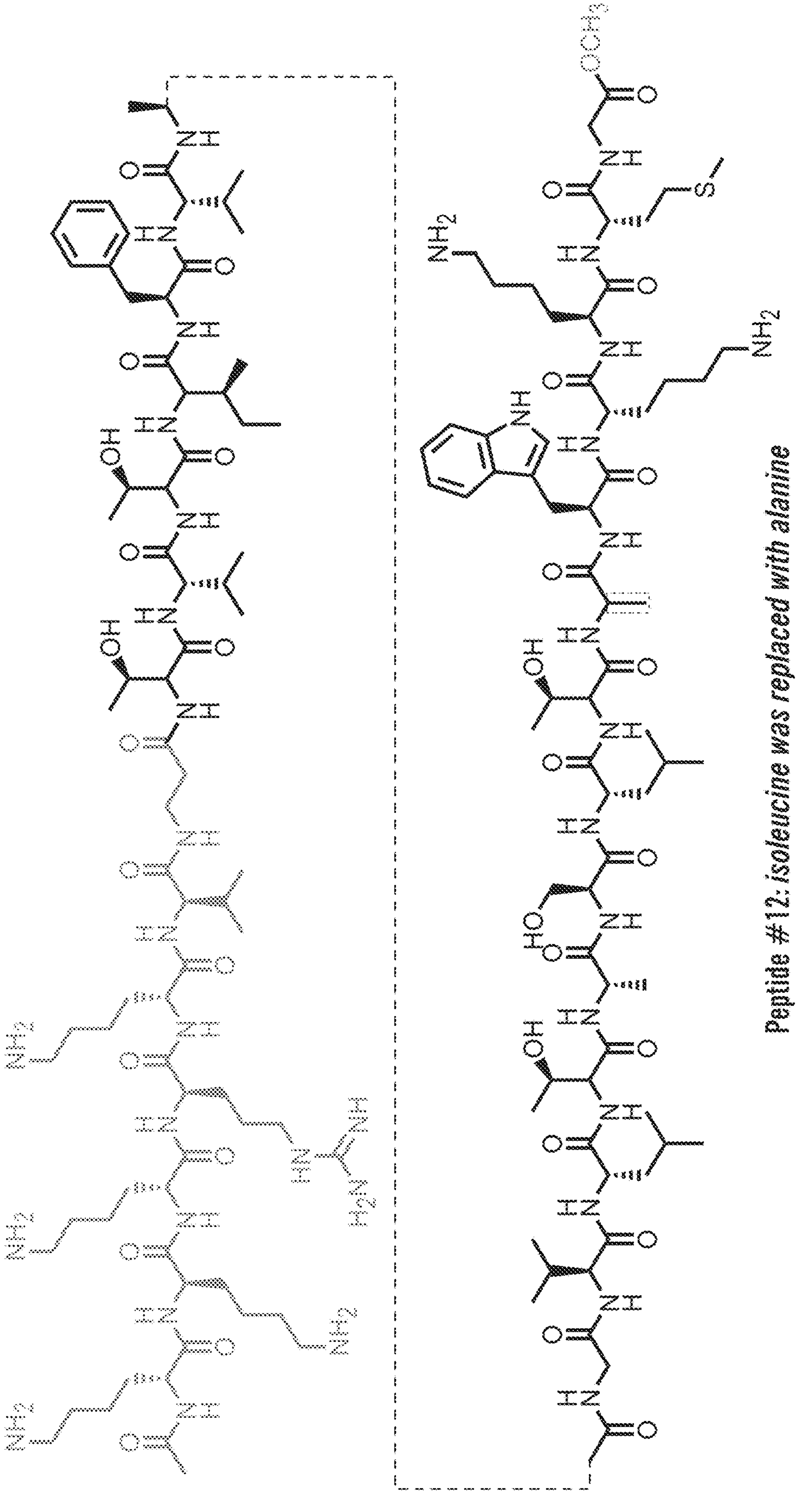
Figure 5B:
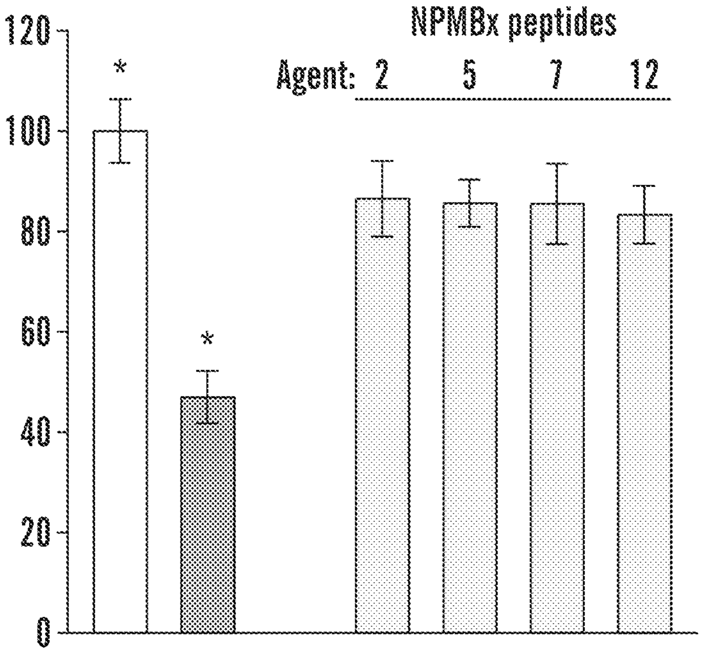

Structure activity relationships of NPMB1 derivatives were determined through alanine scanning. In these studies, 19 polypeptides were produced using methods shown in FIGS. 8-11 and their effect of kidney cell survival after ischemic stress was characterized using the MTT cell survival assay. Based on determination of relative kidney cell survival rate, polypeptides were grouped according to activity as shown in FIG. 2 (orange: 5-40% survival; blue 55-70% survival, or green 80-95% survival).

Modification of both C-terminal and N-terminal ends of NPMB1 was also performed to evaluate their effect on NPMB1 activity. For example, changes to the N-terminus included but are not limited to no modification, addition of an acetyl group, and the addition of the NLS or other targeting sequence.

Peptides of the invention are modified to enhance potency, efficacy and to optimize drug pharmacokinetics by altering the structure of the kidney cell penetrating polypeptides (CPP), the amino and carboxy termini to reduce polypeptide degradation, the NPMB1 binding domain, or the beta linker (FIG. 3-7; 12)

The pharmaceutical compositions of the invention are formulated for parenteral administration (including subcutaneous, intramuscular, intravenous and intradermal), for example isotonic aqueous and non-aqueous sterile injection solutions which may contain anti-oxidants, buffers, and bacteriostats.

Peptides listed in Table 1 were synthesized by addition of the amino acids starting from the C-terminus to the N-terminus on an HMPB-ChemMatrix resin (Biotage) as shown in FIGS. 8-11 and described below. Each amino acid was Nα-Fmoc-protected and the sidechains were protected by acid-labile protecting groups. The first amino acid was coupled in batch and the proceeding amino acids were coupled using Fmoc solid phase synthesis in continuous flow as outlined below.

Peptide Synthesis

Coupling of the C-Terminal Amino Acid in Batch 200 mg of the resin was swollen in dry dichloromethane (DCM) for 10 min. DCM was drained using a vacuum manifold and the resin was incubated with N,N-dimethylformamide for 30 min. 3.33 eq of the C-terminal amino acid end was dissolved in DCM to produce a 0.267 M solution and was cooled to 0° C., then 1.67 eq N,N-diisopropylcarbodiimide (DIC) was added and stirred using a magnetic stir-bar until a white residue is formed. The residue was redissolved in DMF (1:1 volume as with DCM) and was added to the resin followed by addition of 0.1 eq 4-dimethylaminopyridine (DMAP)). The reaction was agitated for 1 h at room temperature, after which the solution was drained and the resin was washed with DMF five times for 1 min per wash). The resin was then subjected to another coupling of the first amino acid to increase amino acid loading. After the second coupling, the resin was washed with DCM twice with 1 min for each wash. 20 eq acetic anhydride in DCM and 20 eq N-methylmorpholine (NMM) also in DCM was added to cap unreacted hydroxyl groups on the linker and was then agitated for 30 min. The resin was drained of the solution and was washed with DCM 5 times and then 2 times with methanol. The resin was then dried using a vacuum manifold.

Peptide Synthesis Using Fmoc Solid Phase Synthesis in Continuous Flow

The resin coupled with the end amino acid was added to a reactor and the reactor was flushed with DMF using an HPLC pump at 20 mL/min and submerged in a 70° C. water bath for 5 minutes. The reactor was flushed with DMF again for 3 min, the Fmoc-group was removed by flowing the reactor with 20% v/v piperidine in DMF for 20 sec, and was washed with DMF for 1 min. The preceding amino acids were dissolved in a 2.5 mL solution of 0.4 M 2-(7-Aza-1Hbenzotriazole-1-yl)-1,1,3,3-tetramethyluronium hexafluorophosphate (HATU) in DMF. Prior to the coupling of each amino acid, the amino acid was activated by addition of 1.56 eq diisopropylethylamine (DIPEA). Amino acids prone to isomerization (e.g., His, Cys, and Trp) were instead activated with 1.1 eq DIPEA. The amino acid was then injected into the reactor using a syringe pump at 8.3 mL/min for 30 sec. The resin was washed with DMF for 1 min, Fmoc was removed using 20% v/v piperidine in DMF, and washed again with DMF for 1 min. From here, the next amino acid was added and the procedure was done reiteratively. N-terminal acetylation was performed by injecting a mixture of 10 mEq acetic anhydride and 10 mEq DIPEA in DMF to the reactor. The resin was washed with DMF for 2 min before removing from the reactor.

Cleavage of the Polypeptide, Sidechain Deprotection and Purification

Cleavage of the polypeptide from the resin and sidechain deprotection was achieved in one step using a a cocktail containing 95% trifluoroacetic acid (TFA), 2.5% triisopropylsilane (TIS), and 2.5% water. 2.5% w/v dithiothreitol (DTT) was added to the solution for polypeptides that contain oxidizable amino acids (Cys, Met). The cocktail solution was added to the resin in a 15 mL polypropylene conical tube and was gently rotated for 3 hr. The resin was filtered using a filtered syringe and the solution was collected in a 15 mL polypropylene conical tube. The solution was concentrated by gently bubbling with nitrogen gas. The polypeptide was then precipitated using diethyl ether. The solution was left at −20° C. overnight and the diethyl ether was aspirated using a syringe. The polypeptide was reconstituted in water, was purified by reverse-phase liquid chromatography, and was dried using a vacuum centrifuge.

Methylation of the C-Terminal Carboxylate

The polypeptide was redissolved in dry methanol and 2 mEq of trimethylsilyl chloride (TMS-Cl) was added. The mixture was shaken overnight and the reaction was monitored using LC-MS. After completion of the reaction, the solution was dried in vacuo, resuspended in water, and the product was quantified by reading the absorbance at 205 nm using a Nanodrop (Thermo Fisher Scientific) or by Bradford Assay.

TABLE 1

List of amino acid sequences of the modified polypeptides. Ac- pertains to an acetyl group, -NH2 pertains to the amide, -OH pertains to the carboxylate, -OMe pertains to the methyl ester, and NLS pertains to the cell penetrating sequence. For clarity, it is noted that the numberic "reference numbers" are not "SEQ ID NOs." The "reference numbers" are sometimes used as polypeptide names in the specification, for example "Agent 5" or "Agent 7." Table discloses SEQ ID NOs: 18-50, respectively, in order of appearance.

| Reference Number | Shortened Nomenclature | Sequence |
|---|---|---|
| N | Negative control: GFP | Ac-PKKKRKV-BA-VTTFSYGVQCFSRYPDHMKQ-OH |
| P | Positive control: Ac-NLS-NPMB1-OH | Ac-PKKKRKV-BA-TVTIFVAGVLTASLTIWKKMG-COOH |
| 1 | Ac-NLS-T172A-OMe | Ac-KKKRKV-BA-AVTIFVAGVLTASLTIWKKMG-OMe |
| 2 | Ac-NLS-V173A-OMe | Ac-KKKRKV-BA-TATIFVAGVLTASLTIWKKMG-OMe |
| 3 | Ac-NLS-T174A-OMe | Ac-KKKRKV-BA-TVAIFVAGVLTASLTIWKKMG-OMe |
| 4 | Ac-NLS-1175A-OMe | Ac-KKKRKV-BA-TVTAFVAGVLTASLTIWKKMG-OMe |
| 5 | Ac-NLS-F176A-OMe | Ac-KKKRKV-BA-TVTIAVAGVLTASLTIWKKMG-OMe |
| 6 | Ac-NLS-V177A-OMe | Ac-KKKRKV-BA-TVTIFÅAGVLTASLTIWKKMG-OMe |
| 7 | Ac-NLS-G179A-OMe | Ac-KKKRKV-BA-TVTIFVAAVLTASLTIWKKMG-OMe |
| 8 | Ac-NLS-V180A-OMe | Ac-KKKRKV-BA-TVTIFVAGALTASLTIWKKMG-OMe |
| 9 | Ac-NLS-L181A-OMe | Ac-KKKRKV-BA-TVTIFVAGVATASLTIWKKMG-OMe |
| 10 | Ac-NLS-T182A-OMe | Ac-KKKRKV-BA-TVTIFVAGVLAASLTIWKKMG-OMe |
| 11 | Åc-NLS-5184A-OMe | Ac-KKKRKV-BA-TVTIFVAGVLTAALTIWKKMG-OMe |
| 12 | Ac-NLSL-L185A-OMe | Ac-KKKRKV-BA-TVTIFVAGVLTASATIWKKMG-OMe |
| 13 | Ac-NLS-T186A-OMe | Ac-KKKRKV-BA-TVTIFVAGVLTASLAIWKKMG-OMe |
| 14 | Ac-NLS-1187A-OMe | Ac-KKKRKV-BA-TVTIFVAGVLTASLTAWKKMG-OMe |
| 15 | Ac-NLS-W188A-OMe | Ac-KKKRKV-BA-TVTIFVAGVLTASLTIAKKMG-OMe |

TABLE 1-continued

List of amino acid sequences of the modified polypeptides. Ac- pertains to an acetyl group, -NH2 pertains to the amide, -OH pertains to the carboxylate, -OMe pertains to the methyl ester, and NLS pertains to the cell penetrating sequence. For clarity, it is noted that the numberic "reference numbers" are not "SEQ ID NOs." The "reference numbers" are sometimes used as polypeptide names in the specification, for example "Agent 5" or "Agent 7." Table discloses SEQ ID NOs: 18-50, respectively, in order of appearance.

| Reference Number | Shortened Nomenclature | Sequence |
|---|---|---|
| 16 | Ac-NLS-K189A-OMe | Ac-KKKRKV-BA-TVTIFVAGVLTASLTIWAKMG-OMe |
| 17 | Ac-NLS-K190A-OMe | Ac-KKKRKV-BA-TVTIFVAGVLTASLTIWKAMG-OMe |
| 18 | Ac-NLS-M191A-OMe | Ac-KKKRKV-BA-TVTIFVAGVLTASLTIWKKAG-OMe |
| 19 | Ac-NLS-G192A-OMe | Ac-KKKRKV-BA-TVTIFVAGVLTASLTIWKKMA-OMe |
| $N_2$ | Negative control: No peptide | |
| $N_3$ | Negative control: GFP | Ac-PKKKRKV-BA-VTTFSYGVQCFSRYPDHMKQ-OH |
| $P_2$ | Positive control: Ac-NLS-NPMB1-OH | Ac-PKKKRKV-BA-TVTIFVAGVLTASLTIWKKMG-COOH |
| $P_3$ | Positive control: Ac-RT-NPMB1-OH | Ac-(KKEEE)3K-BA-TVTIFVAGVLTASLTIWKKMG-COOH |
| 20 | NPMB1-NH2 | TVTIFVAGVLTASLTIWKKMG-NH2 |
| 21 | Ac-NLS-NPMB1-OH | Ac-KKKRKV-BA-TVTIFVAGVLTASLTIWKKMG-OH |
| 22 | NPMB1-OH | TVTIFVAGVLTASLTIWKKMG-OH |
| 23 | Ac-NLS-NPMB1-NH2 | Ac-KKKRKV-BA-TVTIFVAGVLTASLTIWKKMG-NH2 |
| 24 | NPMB1-OMe | TVTIFVAGVLTASLTIWKKMG-OMe |
| 25 | Ac-NPMB1-OH | Ac-TVTIFVAGVL-TASLTIWKKMG-OH |
| 26 | Ac-NPMB1-OMe | Ac-TVTIFVAGVL-TASLTIWKKMG-OMe |
| 27 | Åc-NLS-NPMB1-OMe | Ac-KKKRKV-BA-TVTIFVAGVLTASLTIWKKMG-OMe |
| 28 | Ac-NPMB1-NH2 | Ac-TVTIFVAGVL-TASLTIWKKMG-NH2 |

Example 2

This example uses a different nomenclature system than Example 1. The Example 2 nomenclature system is used in Table 3. The Example 2 peptide naming convention is as follows: NPMB1-(Roman Numeral)-(XXX) where XXX is the ordinal number of the new peptide. Roman numerals VI to IX will be utilized for additional peptides that do not fit the categories listed below.

Roman Numerals denote the following:

I—N-terminal and C-terminal modifications

II—Truncations

III—Alanine scanning

IV—Mutations of natural amino acids

V—Pro-alpha helical amino acids

X—Double mutations

Figure 6:
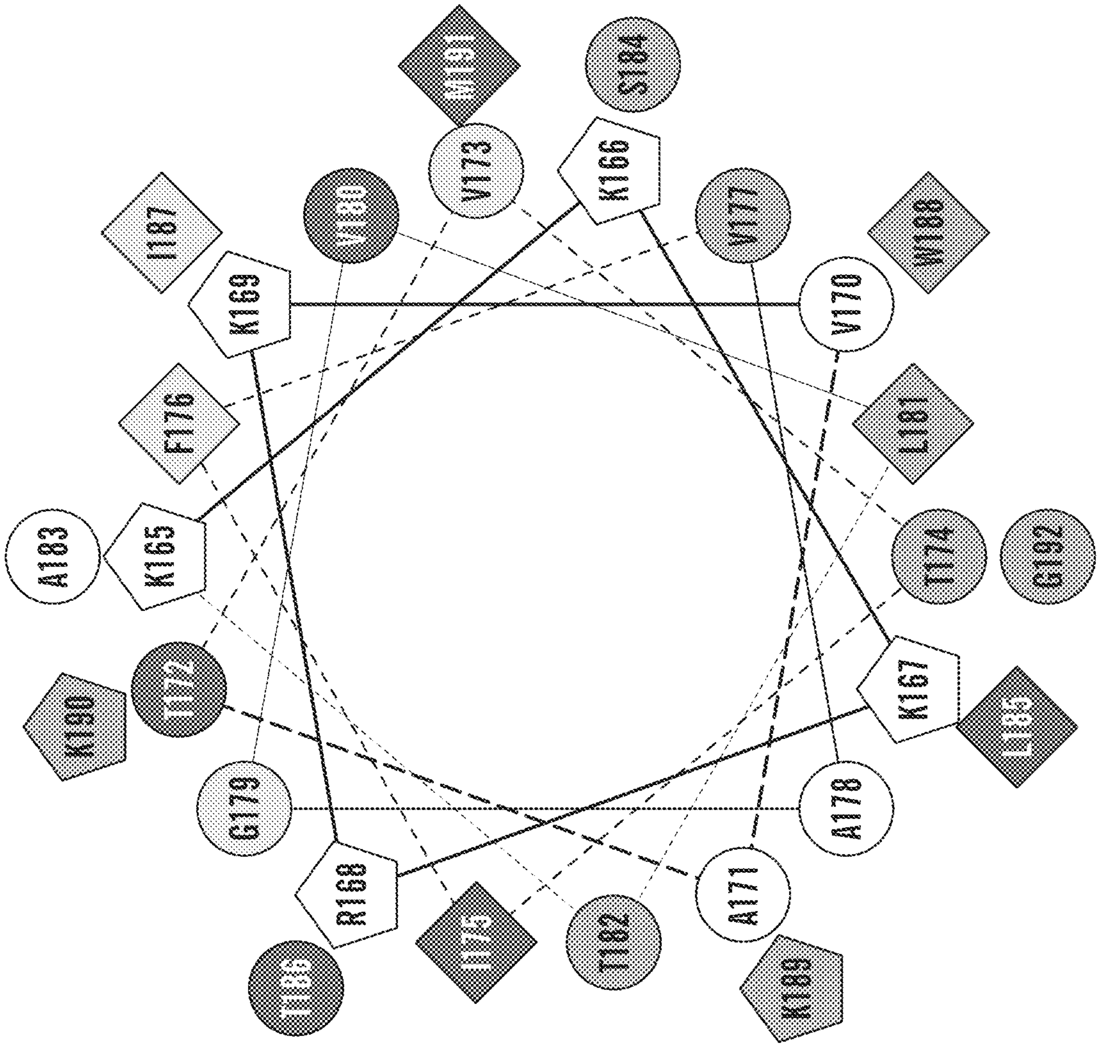
FIG. 6 depicts a 3D Helical Wheel Projection of Human NPMB1; orange residues with the largest effect on cell survival (FIG. 3) cluster in region that reflects the human NPM1 binding domain; K190, located outside this domain might cause steric effects on ligand binding.
Figure 7:
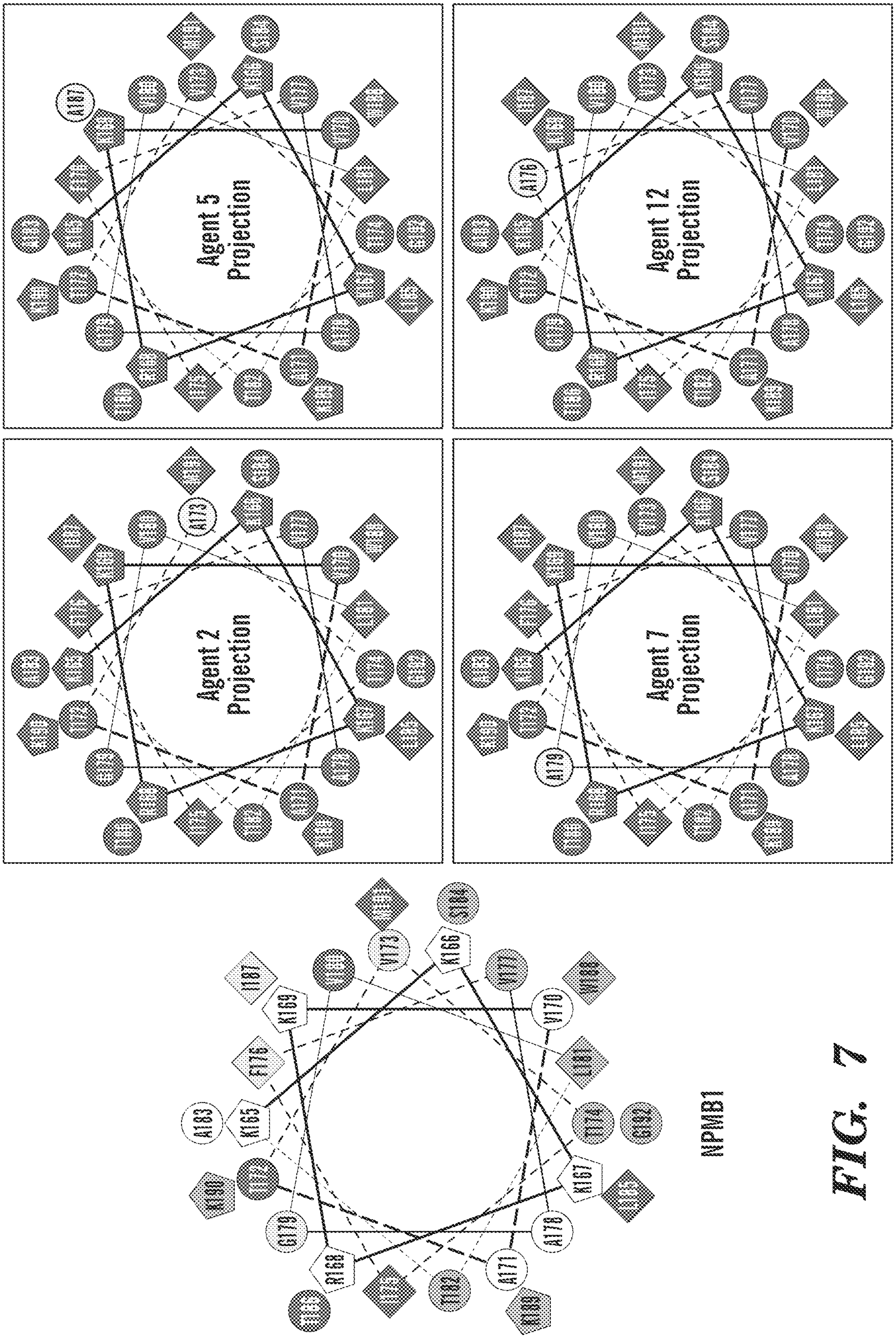
FIG. 7 depicts 3D Helical Wheel Projections of Novel Polypeptides. Agents 2, 5, 7, 12 (FIG. 3) protect against ischemic injury and have unique sequences that differ from NPMB1 but maintain a similar NPM1 binding conformation.
Figure 8:
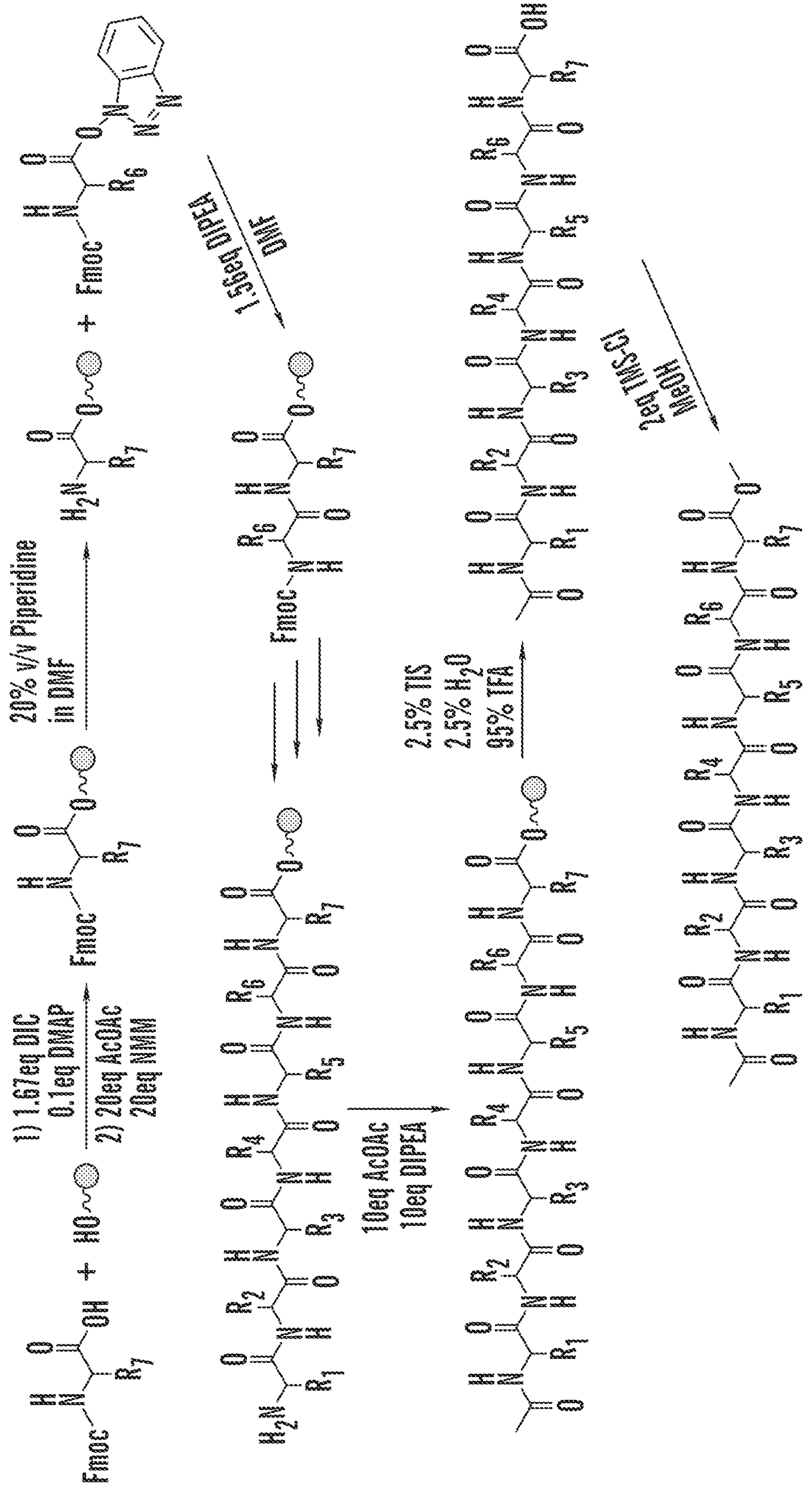
FIG. 8 depicts a polypeptide synthesis route schematic.
Figure 9:
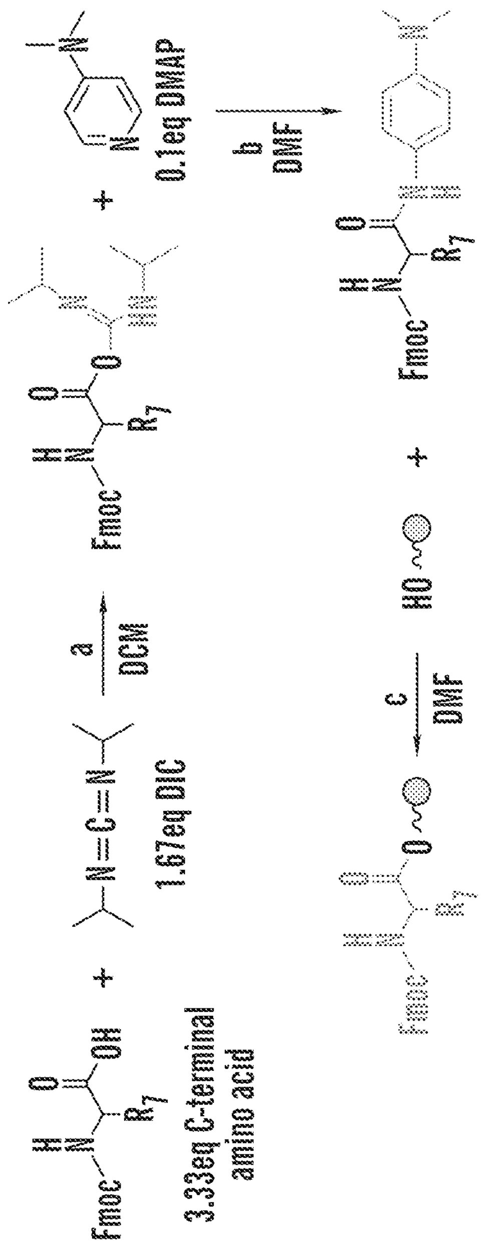
FIG. 9 depicts coupling of the C-terminal amino acid to HMPB-ChemMatrix resin.
Figure 10:
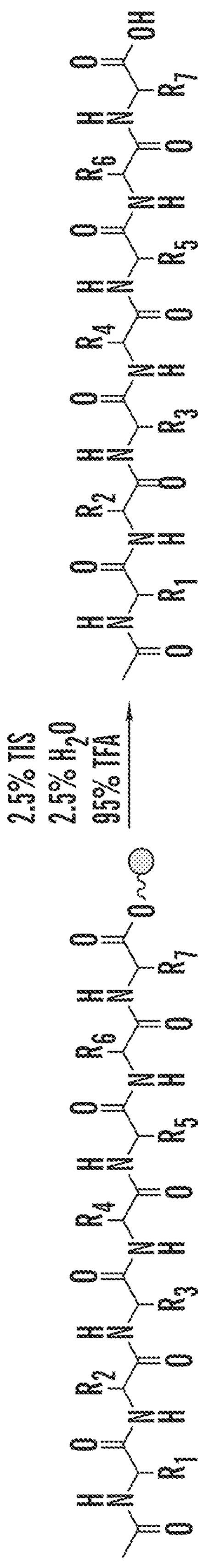
FIG. 10 depicts polypeptide deprotection and cleavage off the resin.
Figure 11:
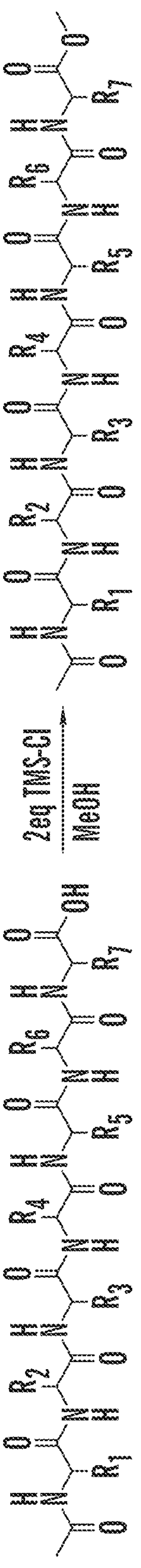
FIG. 11 depicts methylation of the c-terminal carboxylate.
Figure 12:
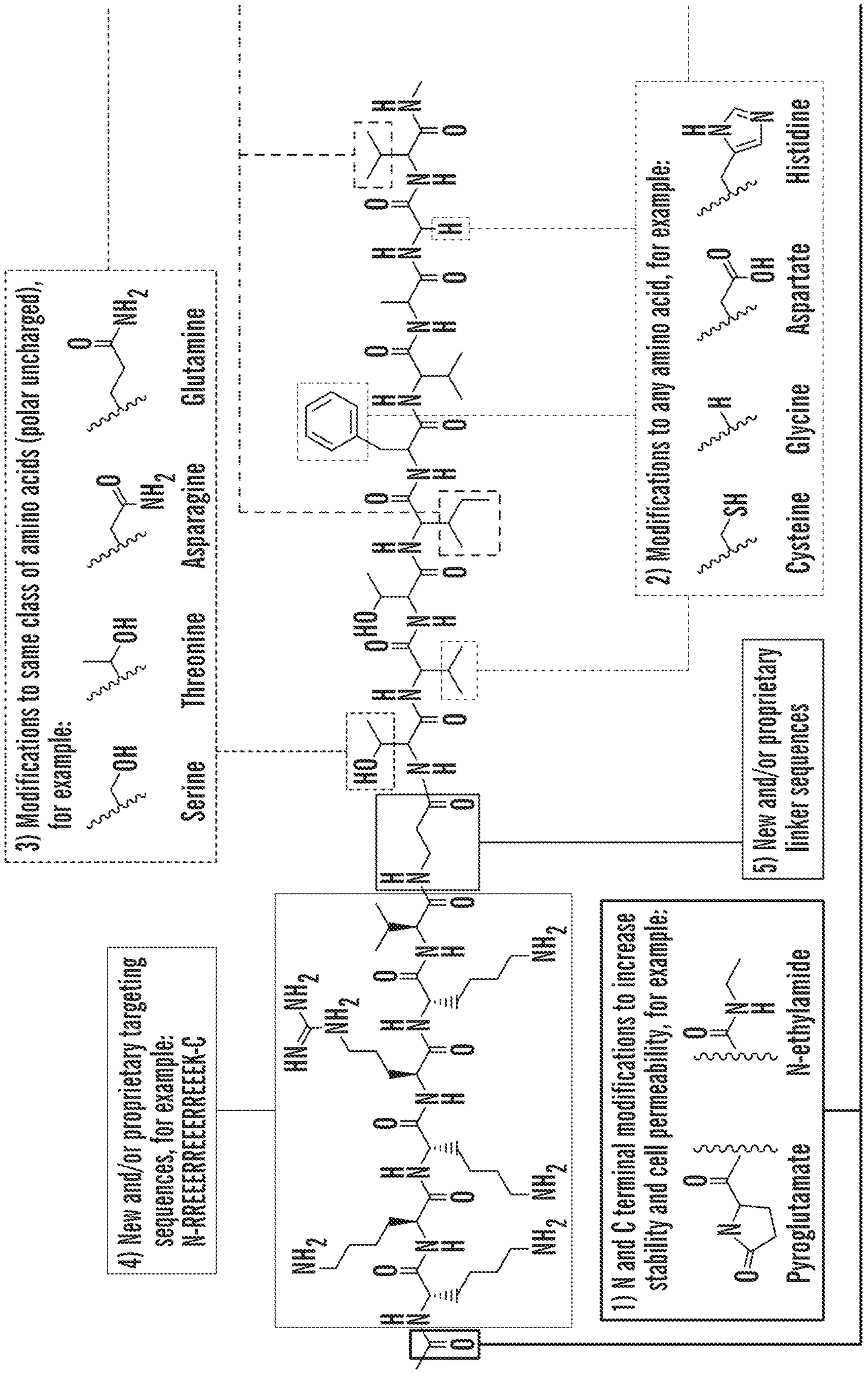
FIG. 12 depicts NPMB1 modifications to enhance potency, efficacy, and optimize drug pharmacokinetics. Described herein is the identification of novel, effective peptide drugs by modifying and optimizing: (1) kidney cell penetrating peptide (CPP); (2) amino and carboxy termini to reduce polypeptide degradation in vivo; (4) the NPMB1 binding domain to increase ligand affinity; (5) the beta linker and eliminating it. Surface plasmon resonance (SPR) testing shows optimizes drug binding affinity between the peptide and human NPM1, its ligand. Figure discloses SEQ ID NOS 17 and 49, respectively, in order of appearance.
Figure 12:
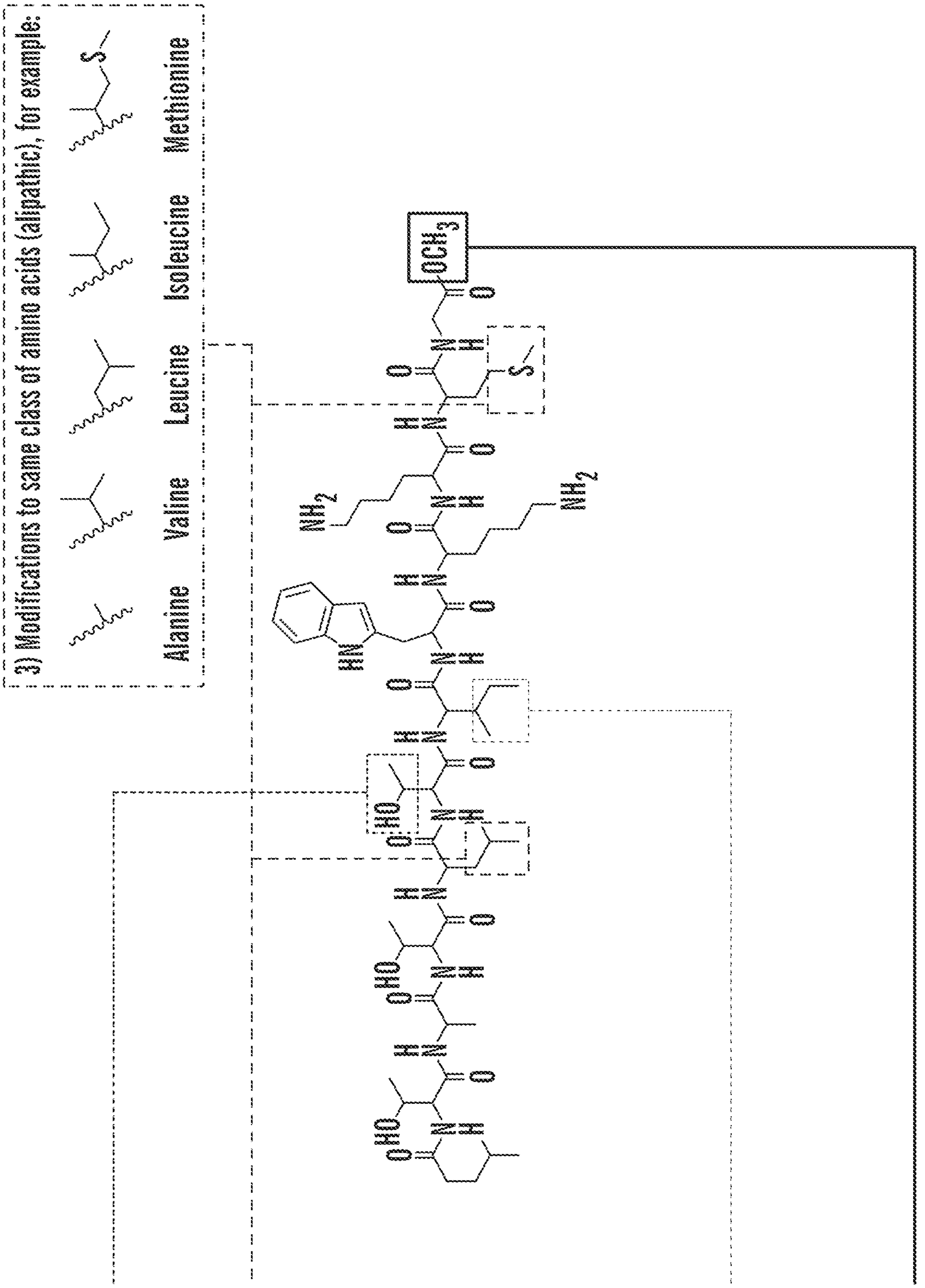

Key residues of the prototype peptide drug (NPMB1) were modified based on the predications from alanine and 3D-helical wheel projection scanning (FIG. 2 and FIGS. 6 and 7). These scans showed marked differences in the post-ischemic survival rates of primary murine proximal tubule epithelial cells (PTEC) after single residue modifications of each non-alanine residue (19 residues were modified in total; FIG. 2).

Alanine scanning identified 9 NPMB1 residues that were critical for cytoprotection and are less amenable to modification (FIG. 2, residues T174, V177, L181, T182, S184, W188, K189, K190, and G192). Only 4 residues (V173, F176, G179 and 1187) exerted minimal effect on cell survival after ischemic stress and modifications are also unlikely to improve drug efficacy. In contrast, 6 residues exerted moderate cytoprotective effects during ischemic stress (residues T172, I175, V180, L185, T186 and M191). The 3D helical wheel projection scan predicted that 5 of 6 peptide residues (except for L185) with intermediate effects on post-ischemic cell survival cluster in a single surface domain (FIGS. 6 and 7). These surface residues are likely regulating the binding affinity Kd) between the therapeutic peptide and NPM1, the human target protein. Since binding affinity (Kd) between the peptide drug and NPMB1 partly predicts its efficacy, a high throughput, quantitative surface plasmon resonance (SPR) assay was developed.

Figure 13A:
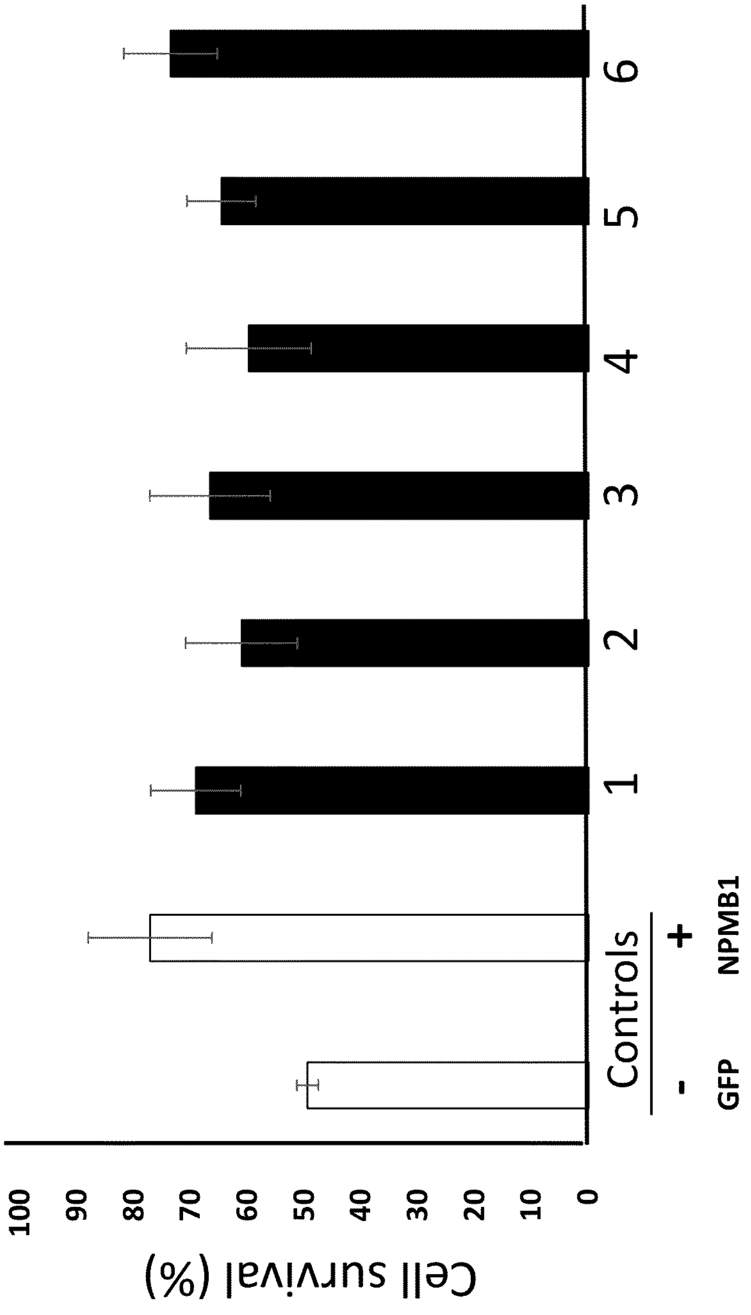

Based on degree of cytoprotection of amino acid substitutions in the alanine scan during ischemic stress, 4 peptides exhibited substantial protection (V173A, F176A, G179A, and I187A) and two peptides from the pro-helical mutations were highly effective in protecting kidney cell survival (T172Q and I175L; FIGS. 6 and 7). Based on these results, a total of 6 novel peptides were selected as candidates to improve kidney cell survival after ischemic stress by at least 20-25% vs. a 21-mer. Size matched peptide based on green fluorescent protein (GFP) was fused to the nuclear localizing sequence ("NLS", a renal targeting cell penetrating sequence or "CPP") with a beta linker sandwiched in between to maintain a favorable peptide conformation for binding NPM1. Peptides were then generated with all possible combinations of these 6 residues modifications totaling 15 distinct peptides). The cytoprotective effects and residue composition of the first 6 peptides with double modifications is shown as compared to a size-matched negative and positive control peptides (FIGS. 13A-13B).

Figure 15:
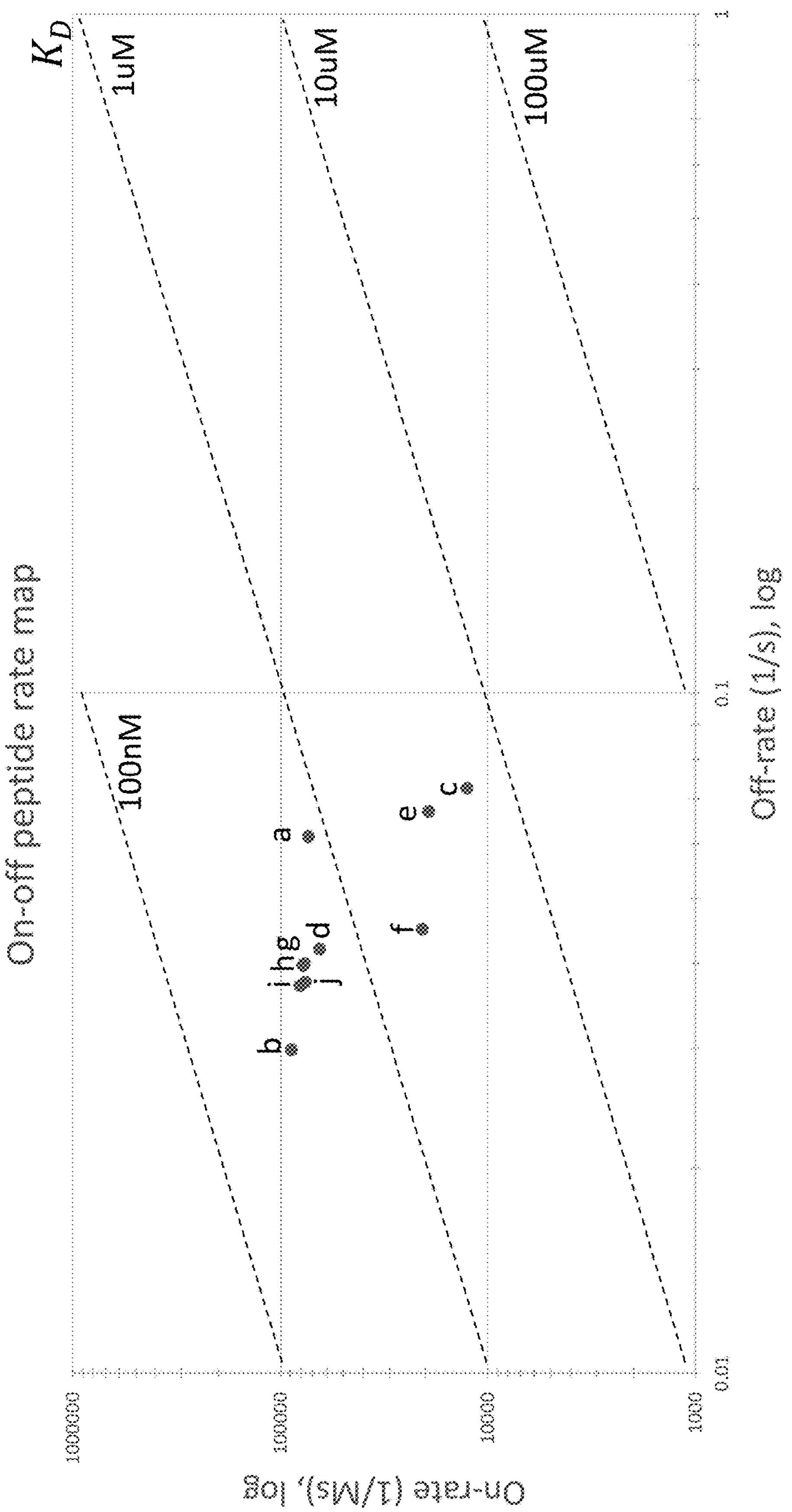
FIG. 15 depicts an on-off rate map. A graph of the off-rate (x-axis) and on-rate (y-axis) of 10 representative peptides from different sets of modified peptides. Diagonal dash-lines represent the equilibrium dissociation constant (KD) estimates the NPM1 binding affinity for each peptide based on the distance to the lines. Calculated KD values are shown in FIG. 14.
Figure 16A:
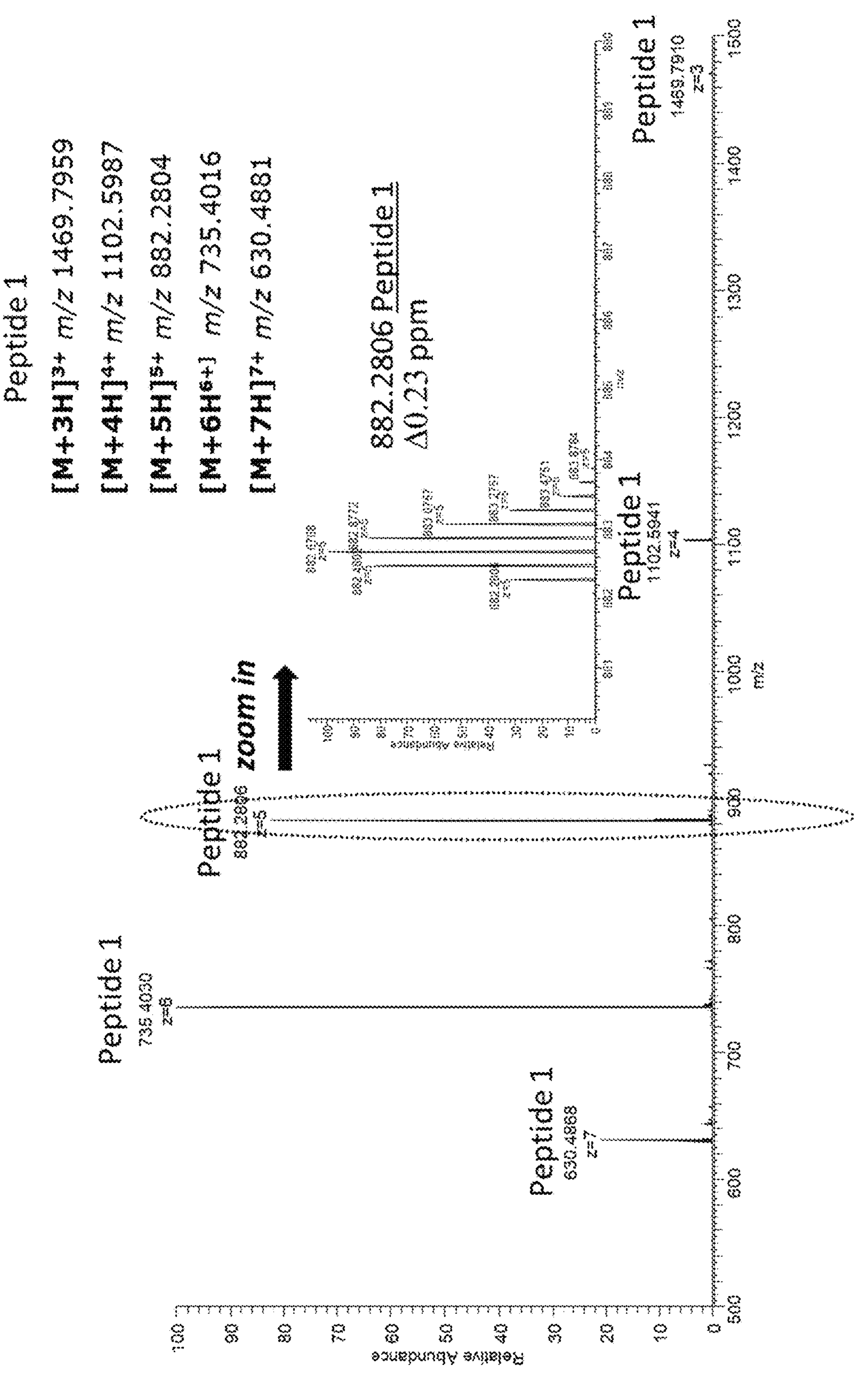
FIG. 16A depicts mass spectrometry of PTEC lysates after incubation with therapeutic peptide. Nano liquid chromatography mass spectrometry spectrum recorded for a <10 kDa size fraction from a PTEC lysate harvested after 1 hour incubation at 37° C. with 100 namomolar NPMB1 peptide. Values for m/z within 1 ppm. Peaks marked p(n+) correspond to the different charge states of the precursor. Inset ("zoom in") shows an expansion of the spectrum in the region corresponding to the [M+5H]5+ charge state of NPMB1 whose monoisotopic peak is found at m/z 882.2806.
Figure 16B:
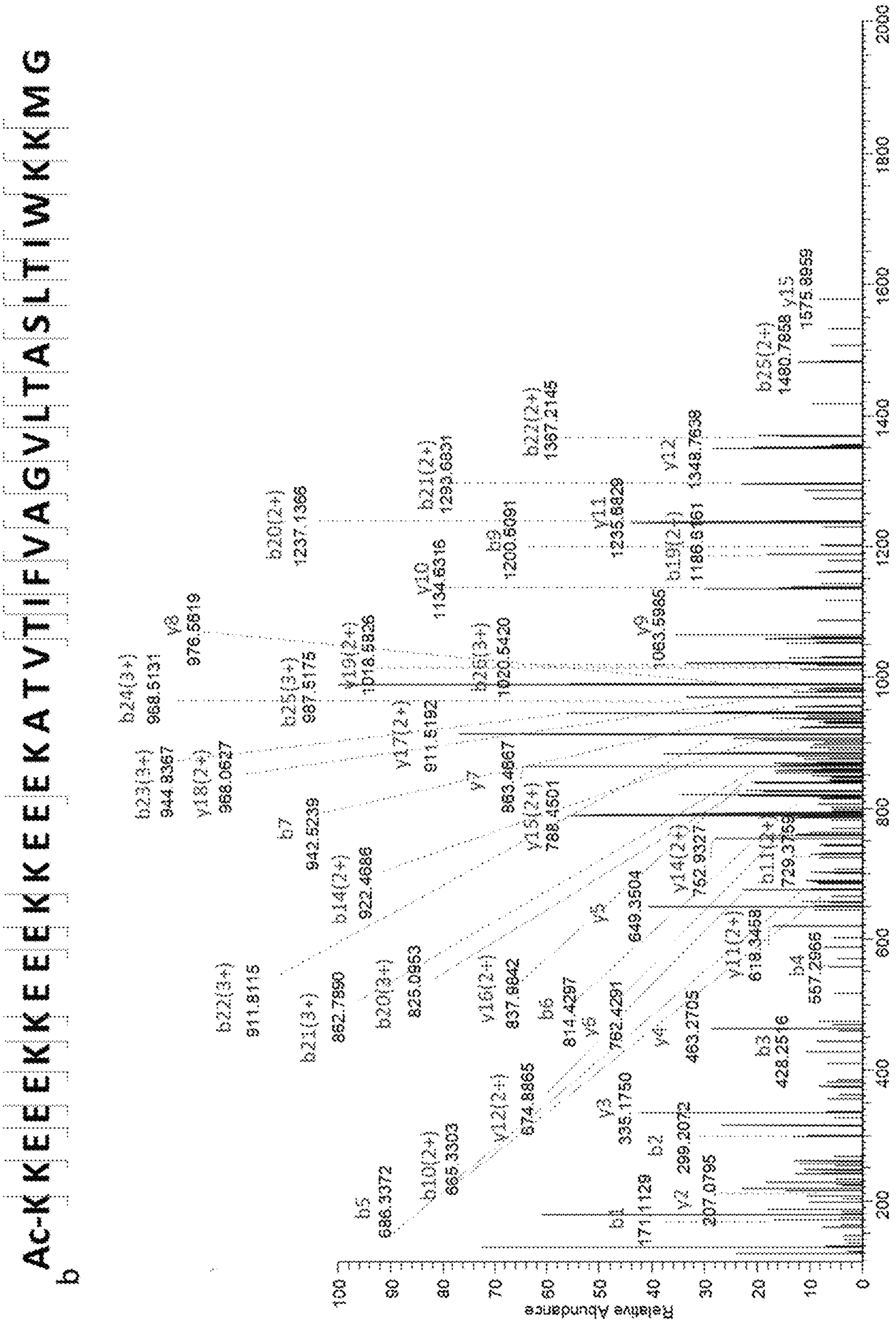
FIG. 16B depicts the HCD MS2 spectrum of the peptide of precursor [M+5H]5+ with sequence ions labeled; b-series product ions contain the N-terminus; y-series product ions contain the C-terminus. Figure discloses SEQ ID NO: 142.

SPR was measured for 10 novel polypeptides with select single or double mutations. Both the measured peptide "on" and "off" rates for binding human NPM1 markedly differed (FIG. 15). As a result, the calculated Kd also showed substantial variability across a 10-fold range between 337 and 5770 nanomolar (FIG. 14). The SPR data show relatively low Kd for two cell penetrating sequences described herein (peptides NPMB1-I-010 and NPMB1-I-011; FIG. 14). Only one of three peptides with pro-alpha helical modifications (NPMB1-V-001) showed a relatively low NPM1 binding affinity. In contrast, 4 of 5 peptides with double modifications (NPMB1-X-002, NPMB1-X-008, NPMB1-X-012, NPMB1-X-013) showed relatively low Kd values, an attractive quality for peptide pharmacophores. Four of 5 peptides with double mutations had low Kd values (except NPMB1-V-003; FIG. 14). For most modified peptides, greater protection against ischemic stress positively correlated with a low Kd. Three peptides (NPMB1-V-001; NPMB1-X-012; NPMB1-X-013) showed cytoprotection in excess of 70% against ischemic stress and exhibited favorable (i.e., low Kd values). Overall, SPR data combined with cell survival data adequately informs the selection of therapeutic peptides based on the quantifiable effects of R group modifications on these parameters. The combination of SPR binding affinity and cell survival data in vitro effectively rank orders therapeutic peptides for in vivo testing in animals.

Importantly, intact peptide is identified by mass spectrometry in primary proximal tubule epithelial cell homogenates after peptide exposure in vitro, documenting drug uptake into the targeted kidney cell type (FIG. 15A-15B). This technique shows that: (1) the instant peptides are detectable in kidney cells; (2) a mass spectrometry-based proteomic approach monitors peptide modifications and (3) permits identification and quantification of the peptides in living samples. Mass spectrometry facilitates peptide optimization based on pharmacokinetics and permits selection of a lead for treating patients with ischemic acute kidney injury (AKI).

Taken together, the instant data identifies the key peptide residues that are critical for peptide efficacy and should be conserved. The instant data also shows that novel, evidence-based modifications of specific peptide drug R groups alter its efficacy in a quantifiable manner based on binding affinity and in vitro cell survival after ischemic stress and that mass spectrometry enables critical PK measurements in cells and tissue.

TABLE 3

An alternative peptide naming system is shown (left-hand column) vs. the Example 1 nomenclature (middle column); peptide sequences are also shown (right-hand column). All 38 peptides in this Table have been tested in vitro and show markedly different degrees of kidney cell protection against ischemic stress (quantified by the MTT assay). Kidney cell survival and surface plasmon resonance (SPR) data for select therapeutic peptides appears in this application.

| Example 2 Nomenclature | Example 1 Nomenclature | Peptide Sequence | SEQ ID NO |
|---|---|---|---|
| NPMB1-I-001 | NPMB1-$NH_2$ | TVTIFVAGVLTASLTIWKKMG-$NH_2$ | 66 |
| NPMB1-I-002 | Ac-NLS-NPMB1-OH | Ac-PKKKRKV-Bala-TVTIFVAGVLTASLTIWKKMG-OH | 67 |

TABLE 3-continued

An alternative peptide naming system is shown (left-hand column) vs. the Example 1 nomenclature (middle column); peptide sequences are also shown (right-hand column). All 38 peptides in this Table have been tested in vitro and show markedly different degrees of kidney cell protection against ischemic stress (quantified by the MTT assay). Kidney cell survival and surface plasmon resonance (SPR) data for select therapeutic peptides appears in this application.

| Example 2 Nomenclature | Example 1 Nomenclature | Peptide Sequence | SEQ ID NO |
|---|---|---|---|
| NPMB1-1-003 | NPMB1-OH | TVTIFVAGVLTASLTIWKKMG-OH | 68 |
| NPMB1-I-004 | Ac-NLS-NPMB1-NH2 | Ac-PKKKRKV-Bala-TVTIFVAGVLTASLTIWKKMG-$NH_2$ | 69 |
| NPMB1-I-005 | NPMB1-OMe | TVTIFVAGVLTASLTIWKKMG-OMe | 70 |
| NPMB1-I-006 | Ac-NPMB1-OH | Ac-TVTIFVAGVLTASLTIWKKMG-OH | 71 |
| NPMB1-I-007 | Ac-NPMB1-OMe | Ac-TVTIFVAGVLTASLTIWKKMG-OMe | 72 |
| NPMB1-I-008 | Ac-NLS-NPMB1-OMe | Ac-PKKKRKV-Bala-TVTIFVAGVLTASLTIWKKMG-OMe | 73 |
| NPMB1-I-009 | Ac-NPMB1-NH2 | Ac-TVTIFVAGVLTASLTIWKKMG-$NH_2$ | 74 |
| NPMB1-I-010 | Ac-$CPP_3$-NPMB1-OH | Ac-KKRRRKKRRRKKRRRK-Bala-TVTIFVAGVLTASLTIWKKMG-OH | 75 |
| NPMB1-I-011 | Ac-$CPP_3$-NPMB1-OH | Ac-RREEERREEERREEEK-Bala-TVTIFVAGVLTASLTIWKKMG-OH | 76 |
| NPMB1-II-001 | Ac-NLS-NPMB1 19mer-OMe | Ac-PKKKRKV-Bala-VTIFVAGVLTASLTIWKKM-OMe | 77 |
| NPMB1-II-002 | Ac-NLS-NPMB1 17mer-OMe | Ac-PKKKRKV-Bala-TIFVAGVLTASLTIWKK-OMe | 78 |
| NPMB1-II-003 | Ac-NLS-NPMB1 15mer-OMe | Ac-PKKKRKV-Bala-IFVAGVLTASLTIWK-OMe | 79 |
| NPMB1-II-004 | Ac-NLS-NPMB1 13mer-OMe | Ac-PKKKRKV-Bala-FVAGVLTASLTIW-OMe | 80 |
| | Ac-NLS-NPMB1 11mer-OMe | Ac-PKKKRKV-Bala-VAGVLTASLTI-OMe | 81 |
| NPMB1-III-001 | Ac-NLS-T172A-OMe | Ac-PKKKRKV-Bala-AVTIFVAGVLTASLTIWKKMG-OMe | 82 |
| NPMB1-III-002 | Ac-NLS-V173A-OMe | Ac-PKKKRKV-Bala-TATIFVAGVLTASLTIWKKMG-OMe | 83 |
| NPMB1-III-003 | Ac-NLS-T174A-OMe | Ac-PKKKRKV-Bala-TVAIFVAGVLTASLTIWKKMG-OMe | 84 |
| NPMB1-III-004 | Ac-NLS-1175A-OMe | Ac-PKKKRKV-Bala-TVTAFVAGVLTASLTIWKKMG-OMe | 85 |
| NPMB1-III-005 | Ac-NLS-F176A-OMe | Ac-PKKKRKV-Bala-TVTIAVAGVLTASLTIWKKMG-OMe | 86 |
| NPMB1-III-006 | Ac-NLS-V177A-OMe | Ac-PKKKRKV-Bala-TVTIFAAGVLTASLTIWKKMG-OMe | 87 |
| NPMB1-III-007 | Ac-NLS-G179A-OMe | Ac-PKKKRKV-Bala-TVTIFVAAVLTASLTIWKKMG-OMe | 88 |
| NPMB1-III-008 | Ac-NLS-V180A-OMe | Ac-PKKKRKV-Bala-TVTIFVAGALTASLTIWKKMG-OMe | 89 |
| NPMB1-III-009 | Ac-NLS-L181A-OMe | Ac-PKKKRKV-Bala-TVTIFVAGVATASLTIWKKMG-OMe | 90 |
| NPMB1-III-010 | Ac-NLS-T182A-OMe | Ac-PKKKRKV-Bala-TVTIFVAGVLAASLTIWKKMG-OMe | 91 |

TABLE 3-continued

An alternative peptide naming system is shown (left-hand column) vs. the Example 1 nomenclature (middle column); peptide sequences are also shown (right-hand column). All 38 peptides in this Table have been tested in vitro and show markedly different degrees of kidney cell protection against ischemic stress (quantified by the MTT assay). Kidney cell survival and surface plasmon resonance (SPR) data for select therapeutic peptides appears in this application.

| Example 2 Nomenclature | Example 1 Nomenclature | Peptide Sequence | SEQ ID NO |
|---|---|---|---|
| NPMB1-III-011 | Ac-NLS-S184A-OMe | Ac-PKKKRKV-Bala-TVTIFVAGVLTAALTIWKKMG-OMe | 92 |
| NPMB1-III-012 | Ac-NLS-L185A-OMe | Ac-PKKKRKV-Bala-TVTIFVAGVLTASATIWKKMG-OMe | 93 |
| NPMB1-III-013 | Ac-NLS-T186A-OMe | Ac-PKKKRKV-Bala-TVTIFVAGVLTASLAIWKKMG-OMe | 94 |
| NPMB1-III-014 | Ac-NLS-1187A-OMe | Ac-PKKKRKV-Bala-TVTIFVAGVLTASLTAWKKMG-OMe | 95 |
| NPMB1-III-015 | Ac-NLS-W188A-OMe | Ac-PKKKRKV-Bala-TVTIFVAGVLTASLTIAKKMG-OMe | 96 |
| NPMB1-III-016 | Ac-NLS-K189A-OMe | Ac-PKKKRKV-Bala-TVTIFVAGVLTASLTIWAKMG-OMe | 97 |
| NPMB1-III-017 | Ac-NLS-K190A-OMe | Ac-PKKKRKV-Bala-TVTIFVAGVLTASLTIWKAMG-OMe | 98 |
| NPMB1-III-018 | Ac-NLS-M191A-OMe | Ac-PKKKRKV-Bala-TVTIFVAGVLTASLTIWKKAG-OMe | 99 |
| NPMB1-III-019 | Ac-NLS-G192A-Ome | Ac-PKKKRKV-Bala-TVTIFVAGVLTASLTIWKKMA-OMe | 100 |
| NPMB1-IV-001 | Ac-NLS-T172S-OMe | Ac-PKKKRKV-Bala-SVTIFVAGVLTASLTIWKKMG-OMe | 101 |
| NPMB1-IV-002 | Ac-NLS-1175V-OMe | Ac-PKKKRKV-Bala-TVTVFVAGVLTASLTIWKKMG-OMe | 102 |
| NPMB1-IV-003 | Ac-NLS-V180L-OMe | Ac-PKKKRKV-Bala-TVTIFVAGLLTASLTIWKKMG-OMe | 103 |
| NPMB1-IV-004 | Ac-NLS-L185V-OMe | Ac-PKKKRKV-Bala-TVTIFVAGVLTASVTIWKKMG-OMe | 104 |
| NPMB1-IV-005 | Ac-NLS-T186S-OMe | Ac-PKKKRKV-Bala-TVTIFVAGVLTASLSIWKKMG-OMe | 105 |
| NPMB1-IV-006 | Ac-NLS-4xAla-Ome | Ac-PKKKRKV-Bala-TATIAVAAVLTASLTAWKKMG-OMe | 106 |
| NPMB1-I-001 | NPMB1-$NH_2$ | TVTIFVAGVLTASLTIWKKMG-$NH_2$ | 107 |
| NPMB1-I-002 | Ac-NLS-NPMB1-OH | Ac-PKKKRKV-Bala-TVTIFVAGVLTASLTIWKKMG-OH | 108 |
| NPMB1-I-003 | NPMB1-OH | TVTIFVAGVLTASLTIWKKMG-OH | 109 |
| NPMB1-I-004 | Ac-NLS-NPMB1-NH2 | Ac-PKKKRKV-Bala-TVTIFVAGVLTASLTIWKKMG-$NH_2$ | 110 |
| NPMB1-I-005 | NPMB1-OMe | TVTIFVAGVLTASLTIWKKMG-OMe | 111 |
| NPMB1-I-006 | Ac-NPMB1-OH | Ac-TVTIFVAGVLTASLTIWKKMG-OH | 112 |
| NPMB1-1-007 | Ac-NPMB1-OMe | Ac-TVTIFVAGVLTASLTIWKKMG-OMe | 113 |
| NPMB1-I-008 | Ac-NLS-NPMB1-OMe | Ac-PKKKRKV-Bala-TVTIFVAGVLTASLTIWKKMG-OMe | 114 |
| NPMB1-I-009 | Ac-NPMB1-NH2 | Ac-TVTIFVAGVLTASLTIWKKMG-$NH_2$ | 115 |
| NPMB1-I-010 | Ac-$CPP_3$-NPMB1-OH | Ac-KKRRRKKRRRKKRRRK-Bala-TVTIFVAGVLTASLTIWKKMG-OH | 116 |

TABLE 3-continued

An alternative peptide naming system is shown (left-hand column) vs. the Example 1 nomenclature (middle column); peptide sequences are also shown (right-hand column). All 38 peptides in this Table have been tested in vitro and show markedly different degrees of kidney cell protection against ischemic stress (quantified by the MTT assay). Kidney cell survival and surface plasmon resonance (SPR) data for select therapeutic peptides appears in this application.

| Example 2 Nomenclature | Example 1 Nomenclature | Peptide Sequence | SEQ ID NO |
|---|---|---|---|
| NPMB1-1-011 | Ac-CPP$_3$-NPMB1-OH | Ac-RREEERREEERREEEK-Bala-TVTIFVAGVLTASLTIWKKMG -OH | 117 |
| NPMB1-II-001 | Ac-NLS-NPMB1 19mer-OMe | Ac-PKKKRKV-Bala-VTIFVAGVLTASLTIWKKM-OMe | 118 |
| NPMB1-II-002 | Ac-NLS-NPMB1 17mer-OMe | Ac-PKKKRKV-Bala-TIFVAGVLTASLTIWKK-OMe | 119 |
| NPMB1-II-003 | Ac-NLS-NPMB1 15mer-OMe | Ac-PKKKRKV-Bala-IFVAGVLTASLTIWK-OMe | 120 |
| NPMB1-II-004 | Ac-NLS-NPMB1 13mer-OMe | Ac-PKKKRKV-Bala-FVAGVLTASLTIW-OMe | 121 |
| | Ac-NLS-NPMB1 11mer-OMe | Ac-PKKKRKV-Bala-VAGVLTASLTI-OMe | 122 |
| NPMB1-V-001 | Ac-NLS-1175L-OMe | Ac-PKKKRKV-Bala-TVTLFVAGVLTASLTIWKKMG-OMe | 123 |
| NPMB1-V-002 | Ac-NLS-4xaH-OMe | Ac-PKKKRKV-Bala-QVTLFVAGLLTASLQIWKKMG-OMe | 124 |
| NPMB1-V-003 | Ac-NLS-T186Q-OMe | Ac-PKKKRKV-Bala-TVTIFVAGVLTASLQIWKKMG-OMe | 125 |
| NPMB1-V-004 | Ac-NLS-T172Q-OMe | Ac-PKKKRKV-Bala-QVTIFVAGVLTASLTIWKKMG-OMe | 126 |
| NPMB1-X-001 | Ac-NLS-T172Q,I187A-OMe | Ac-PKKKRKV-Bala-QVTIFVAGVLTASLTAWKKMG-OMe | 127 |
| NPMB1-X-002 | Ac-NLS-1175L-I187A-OMe | Ac-PKKKRKV-Bala-TVTLFVAGVLTASLTAWKKMG -OMe | 128 |
| NPMB1-X-003 | Ac-NLS-F176A,I187A-OMe | Ac-PKKKRKV-Bala-TVTIAVAGVLTASLTAWKKMG-OMe | 129 |
| NPMB1-X-004 | Ac-NLS-G179A,187A-OMe | Ac-PKKKRKV-Bala-TVTIFVAAVLTASLTAWKKMG-OMe | 130 |
| NPMB1-X-005 | Ac-NLS-I175L,G179A-OMe | Ac-PKKKRKV-Bala-TVTLFVAAVLTASLTIWKKMG-OMe | 131 |
| NPMB1-X-006 | Ac-NLS-T172Q,G179A-OMe | Ac-PKKKRKV-Bala-QVTIFVAAVLTASLTIWKKMG-OMe | 132 |
| NPMB1-X-007 | Ac-NLS-V173A,G179A-OMe | Ac-PKKKRKV-Bala-TATIFVAAVLTASLTIWKKMG-OMe | 133 |
| NPMB1-X-008 | Ac-NLS-F176A,G179A-OMe | Ac-PKKKRKV-Bala-TVTIAVAAVLTASLTIWKKMG-OMe | 134 |
| NPMB1-X-009 | Ac-NLS-T172Q,F176A-OMe | Ac-PKKKRKV-Bala-QVTIAVAGVLTASLTIWKKMG-OMe | 135 |

TABLE 3-continued

An alternative peptide naming system is shown (left-hand column) vs. the Example 1 nomenclature (middle column); peptide sequences are also shown (right-hand column). All 38 peptides in this Table have been tested in vitro and show markedly different degrees of kidney cell protection against ischemic stress (quantified by the MTT assay). Kidney cell survival and surface plasmon resonance (SPR) data for select therapeutic peptides appears in this application.

| Example 2 Nomenclature | Example 1 Nomenclature | Peptide Sequence | SEQ ID NO |
|---|---|---|---|
| NPMB1-X-010 | Ac-NLS-I175L,F176A-OMe | Ac-PKKKRKV-Bala-TVTLAVAGVLTASLTIWKKMG-OMe | 136 |
| NPMB1-X-011 | Ac-NLS-T172Q, V173A-OMe | Ac-PKKKRKV-Bala-QATIFVAGVLTASLTIWKKMG-OMe | 137 |
| NPMB1-X-012 | Ac-NLS-V173A,F176A-OMe | Ac-PKKKRKV-Bala-TATIAVAGVLTASLTIWKKMG-OMe | 138 |
| NPMB1-X-013 | Ac-NLS-V173A,I175L-OMe | Ac-PKKKRKV-Bala-TATLFVAGVLTASLTIWKKMG-OMe | 139 |
| NPMB1-X-014 | Ac-NLS-T172Q,1175L-OMe | Ac-PKKKRKV-Bala-QVTLFVAGVLTASLTIWKKMG-OMe | 140 |
| NPMB1-X-015 | Ac-NLS-V173A-I187A-OMe | Ac-PKKKRKV-Bala-TATIFVAGVLTASLTAWKKMG-OMe | 141 |

What is claimed herein:

1. A polypeptide comprising at least one nucleophosmin-binding domain, each nucleophosmin-binding domain comprising the sequence of SEQ ID NO: 5 ($TX_4X_5X_6X_7X_8X_9X_{10}$ $TX_{12}S$ $X_{14}X_{15}X_{16}WKKX_{20}G$), wherein $X_5$ is alanine, $X_{12}$ is alanine, $X_{14}$ is leucine; and wherein the polypeptide does not comprise SEQ ID NO: 1.

2. The polypeptide of claim 1, comprising the sequence of SEQ ID NO: 2, 3, 4, 7, 14, 54, 55, 57, 59, 60, or 64.

3. The polypeptide of claim 1, wherein an X comprised by one of SEQ ID Nos: 2-5, 7, 54, or 55, other than $X_5$, $X_{12}$, or $X_{14}$, is a non-natural amino acid.

4. The polypeptide of claim 1, wherein an X comprised by one of SEQ ID Nos: 2-5, 7, 54, or 55, other than $X_5$, $X_{12}$, or $X_{14}$, is alanine.

5. The polypeptide of claim 1, further comprising at least one N-terminus modification and/or at least one C-terminus modification.

6. The polypeptide of claim 5, wherein the at least one N-terminus modification and/or at least one C-terminus modification is selected from acetylation, methyl esterification, amidation, carboxylation, N-ethylamidation, and addition of pyroglutamate.

7. The polypeptide of claim 1, comprising at least one C-terminus modification.

8. The polypeptide of claim 7, wherein the at least one C-terminus modification is amidation or methyl esterification.

9. The polypeptide of claim 8, wherein the at least one C-terminus modification is amidation.

10. The polypeptide of claim 8, wherein the at least one C-terminus modification is methyl esterification.

11. The polypeptide of claim 1, wherein the polypeptide further comprises an N-terminal or C-terminal cell penetration motif.

12. The polypeptide of claim 11, wherein the N-terminal or C-terminal cell penetration motif and the at least one nucleophosmin-binding domain are separated by a linker.

13. The polypeptide of claim 12, wherein the linker is an alanine residue.

14. The polypeptide of claim 12, wherein the linker is a beta-alanine residue.

15. The polypeptide of claim 1, wherein the polypeptide further comprises an N-terminal cell penetration motif.

16. The polypeptide of claim 15, wherein the cell penetration motif comprises PKKKRKV (SEQ ID NO: 10), RREEERREEERREEEK (SEQ ID NO: 17), or KKRRRKKRRRKKRRRK (SEQ ID NO: 53).

17. The polypeptide of claim 1, wherein the polypeptide comprises the sequence of one of SEQ ID NOs: 24, 86, 106, 129, 134-136, and 138.

18. The polypeptide of claim 1, wherein the polypeptide comprises the sequence of one of SEQ ID NOs: 134 and 138.

19. The polypeptide of claim 1, wherein the polypeptide comprises the sequence of one of SEQ ID NO: 138.

20. The polypeptide of claim 1, comprising the sequence of SEQ ID NO: 57.

21. A method of treating acute kidney injury due to ischemia in a subject, the method comprising administering the polypeptide of claim 11 to the subject.

22. A method of treating ischemia in a subject, the method comprising administering the polypeptide of claim 11 to the subject.

23. The method of claim 22, wherein the subject is a post-operative cardiac surgery patient.

24. The method of claim 22, wherein the administration occurs before cardiac surgery.

* * * * *